United States Patent
Wang et al.

(10) Patent No.: US 8,227,586 B2
(45) Date of Patent: Jul. 24, 2012

(54) HUMAN POLYOMAVIRUS, DESIGNATED THE WU VIRUS, OBTAINED FROM HUMAN RESPIRATORY SECRETIONS

(75) Inventors: David Wang, St. Louis, MO (US); Guang Wu, St. Louis, MO (US); Anne Gaynor, St. Louis, MO (US); Michael Nissen, Indooroopilly (AU); Theo Sloots, Riverhills (AU)

(73) Assignees: Washington University, St. Louis, MO (US); Queensland Health, Brisbane, Queensland (AU)

( * ) Notice: Subject to any disclaimer, the term of this patent is extended or adjusted under 35 U.S.C. 154(b) by 1200 days.

(21) Appl. No.: 12/029,390

(22) Filed: Feb. 11, 2008

(65) Prior Publication Data

US 2011/0177589 A1    Jul. 21, 2011

Related U.S. Application Data

(60) Provisional application No. 60/900,502, filed on Feb. 9, 2007, provisional application No. 60/919,667, filed on Mar. 22, 2007.

(51) Int. Cl.
*C07H 21/04* (2006.01)
*A61K 39/12* (2006.01)
*C12N 15/00* (2006.01)

(52) U.S. Cl. ............... 536/23.72; 424/204.1; 435/320.1

(58) Field of Classification Search .................. None
See application file for complete search history.

(56) References Cited

PUBLICATIONS

Misawa, K., et al., 2000, A method to identify cDNAs based on localization of green fluorescent protein fusion products, Proc. Natl. Acad. Sci. 97(7):3062-3066.*
Gaynor, A. M., et al., May 2007, Identification of a novel polyomavirus from patients with acute respiratory tract infections, PLoS Pathogens, 3(5):e64-0595-0604.*
Agostini et al., Arch. Virol. (1997) 142:637-655.
Allander et al., J. Virol. (2007) ePub PMID:17287263.
Arden et al., J. Med. Virol. (2006) 78:1232-1240.
Cantalupo et al., J. Virol. (2005) 79:13094-13104.
Choi et al., Clin. Infect. Dis. (2006) 43:585-592.
Gardner et al., Lancet (1971) 1:1253-1257.
Goudsmit et al., J. Med. Virol. (1982) 10:91-99.
Greenlee, Infect. Immun. (1981) 33:297-303.
Hahn et al., Nature (1999) 400:464-468.
Heikkinen and Jarvinen, Lancet (2003) 361:51-59.
Ksiazek et al., N. Engl. J. Med. (2003) 348:1953-1966.
Padgett et al., Lancet (1971) 1:1257-1260.
Pipas, J. Virol. (1992) 66:3979-3985.
Sloots et al., J. Clin. Virol. (2006) 35:99-102.
Stolt et al., J. Gen. Virol. (2003) 84:1499-1504.
Sumino et al., J. Infect. Dis. (2005) 192:1052-1060.
Sundsfjord et al., J. Clin. Microbiol. (1994) 32:1390-1394.
Van Den Hoogen et al., Nat Med. (2001) 7:719-724.
Van Der Hoek et al., Nat. Med. (2004) 10:368-373.
Wang et al., PLoS Biol. (2003) 1:E2.
Woo et al., J. Virol. (2005) 79:884-895.

* cited by examiner

*Primary Examiner* — Jeffrey S. Parkin
(74) *Attorney, Agent, or Firm* — Morrison & Foerster LLP

(57) ABSTRACT

Provided herein is a novel human polyomavirus, its nucleic acid sequence, as well as methods to detect and diagnosis the presence of the polyomavirus.

3 Claims, 8 Drawing Sheets

Figure 1:
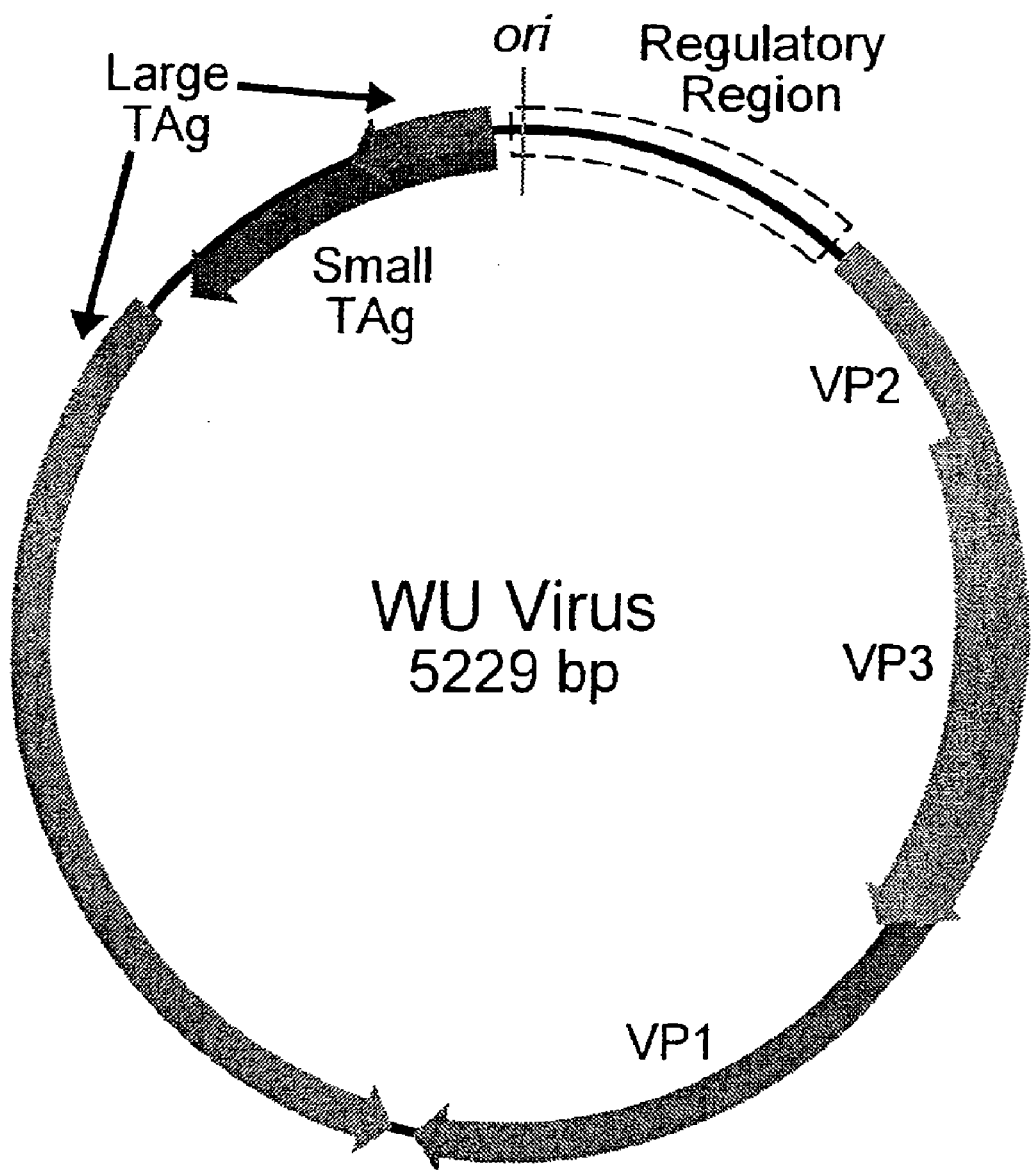

```
>DWAB-aaa05a03.g1
GCACTTATAGCAGTAACACTCTATCCACATTGGAGGTTTTCTAAATATTTTATATTTTTGCTTGTGGCGCT
TGTCTAAAAAGCAGTAAAAACAATTACACAAATAATAAAACCCCTTTAAGCATATGTCCCAGTCTTTTAAA
ATATACTCTTCAAAAACATCACCATAAACTTCTCCAACAAGCCTGTACTTTCTAGGGGGAAAGTTACAGCA
CAATTCTGTGCATTCTACCTGTGAAGAACTCCACACTTCATCTTCTTCTTCATTTAGTTGGTGCACTGTAC
TAACACACTCTTGCAGTTTTAAATATAAAGAATTAAGCTTTTTCATTTTTTCCTCATTTCCCCCTTTGTCA
GG >DWAB-aaa05a04.g1
GCAGCTGTAGCAGTAACACTCTATCCACATTGGAGGTTTTCTAAATATTTTATATTTTTGCTTGTGGCGCT
TGTCTAAAAAGCAGTAAAAACAATTACACAAATAATAAAACCCCTTTAAGCATATGTCCCAGTCTTTTAAA
ATATACTCTTCAAAAACATCACCATAAACTTCTCCAACAAGCCTGTACTTTCTAGGGGGAAAGTTACAGCA
CAATTCTGTGCATTCTACCTGTGAAGAGCTCCACACTTCATCTTCTTCTTCATTTAGTTGGTGCACTGTAC
TAACACACTCTTGCAGTTTTAAATATAAAGAATTAAGCTTTTTCATTTTTTCCTCATTTCCCCCTTTGTCA
GG >DWAB-aaa05h07.g1
TGGCTTATTAAACACCTGCTTATAAAGCAAATTTATAGTATATGGGTTTCTAACCCTTCTTTGTCTAAAGT
GTAGCCTAAAAAATCTGGAAAGCCCTGTATGTACTCTATTTTTGTTAACTCCCAAAAGGTCAGCACAAGTT
ATGTACAATCTACCTTGCAAGCAAAGAATGCCAATGCCATTTTCATCCAACAGTGGAATTGTGCTATTATT
ACTAAATGACACCACTGGTGGAGTTGCAGCCCCTCCAACCATTCTGCCAAAGTATCTGCAGTTATCATTGC
GGCTAGGGTCTGCCACCCATGATTCAATGCTGTACTTTTCATTAGTGACCCTTGCCCTGGGTGTTTCAGAA
CTGGAATAAACATGAGGCACAGTACCATTGGTTTTAGGATTTACAGTATACTGAG >DWAB-aaa06g03.g1
GTTGACACACATTTTTTTGACTTTTACTGTCTGAAAATAGTAAAGCATTTTTTTGATGTTCCATATGAAGT
CTATTATGAGTTGCATCTTCATTACTATTGCATTTTTCACACTCTTCTACCTTAATAGATAGTTGTAAATA
TAATCCAAGTAATAAGTACACATCATCAATTCCTAATTCTAAAGCAAATTCTGACAAAGCCTTCCAATTTA
ATTGATCTTTAAACTCCCCATATAAATCCTCAGCTTTAAAATCATTTTCTTTTAAGCCACCAGGAATATTT
TCTTCACATAAAGTAAATGGATCTCTAGTCATTCTACTATATAAACCATATGCATTATTAACACCTTTACA
AAATAAAAAGCTAATAGTACAGTATCCCTTACAAAAGTTATTAACAGCACTAACTCTATGTCTAAAAGGTG
TTAAAATAAACACAAGTGCAGTATTATAATAAGAATGTCTACTTGCAAAATTACATTTAAACTTACTTAAA
AGTTTTTTATATAGGGTTTCTGCCTTTTCTTTGGTGGTATGTATTACAAATGCAGTTAAAGTTCTATTACT
AAATACAGCTTGAGACACAAATTCTTCCAATTCTTTAGGAAATGATAAAGATGCATCTGTAGCATTGTCCT
TTTTTTTTTT >DWAB-aaa06h01.g1
TTCTAACCCTTCTTTGTCTAAAGTGTAGCCTAAAAAATCTGGAAAGCCCTGTATGTACCCTATTTTTGTTA
ACTCCCAAAAGGTCAGCACAAGTTATGTACAATCTACCTTGCAAGCAAAGAATGCCAATGCCATTTTCATC
CAACAGTGGAATTGTGCTATTATTACTAAATGACACCACTGGTGGAGTTGCAGCCCCTCCAACCATTCTGC
CAAAGTATCTGCAGTTATCATTGCGGCTAGGGTCTGCCACCCATGATTCAATGCTGTACTTTTCATTAGTG
ACCCTTGCCCTGGGTGTTTCAGAACTGGAATAAACATGAGGCACAGTACCATTGGTTTTAGGATTTACAGT
ATACTGAGCAGGCCCCTTGTATTTTTCAGTGGGAGCAAGTCCTAGCACATCCAAGGGCTGTCCTCCAACTG
CCCAAAAATAAAGTTGGGACCAGCAATACCTCCTACACCCCTGTAGTAAGTATGCCAGCATTAAGCACA
GGAAGCACCAAAACTTCTGTTTCCATTCTATACAGCTCCCATATAAGCATGTCACATTCACTAACCTGATT
AGGAATATCAGGGGGAGCAACCTGTGACAAGCTGTAGCACACAGTAGTATCGGCATCAGGAGTAACATTAG
CAGCTTCAGCAGTTTTAAGTGGGCTACTAATAGACCAATAATGTGGGGTAGTCCCCTCTGCATTTCCAATA
ACAGGTTTAACAAACAATTCAA >DWAB-aaa08f04.g1
TCCCCCTGATATTCCTAATCAGGTTAGTGAATGTGACATGCTTATATGGGAGCTGTATAGAATGGAAACAG
AAGTTTTGGTGCTTCCTGTGCTTAATGCTGGCATACTTACTACAGGGGGTGTAGGAGGTATTGCTGGTCCC
```

FIGURE 4-1

```
CAACTTTATTTTTGGGCAGTTGGAGGACAGCCCTTGGATGTGCTAGGACTTGCTCCCACTGAAAAATACAA
GGGGCCTGCTCAGTATACTGTAAATCCTAAAACCAATGGTACTGTGCCTCATGTTTATTCCAGTTCTGAAA
CACCCAGGGCAAGGGTCACTAATGAAAAGTACAGCATTGAATCATGGGTGGCAGACCCTAGCCGCAATGAT
AACTGCAGATACTTTGGCAGAATGGTTGGAGGGGCTGCAACTCCACCAGTGGTGTCATTTAGTAATAATAG
CACAATTCCACTGTTGGATGAAAATGGCATTGGCATTCTTTGCTTGCAAGGTAGATTGTACATAACTTGTG
CTGACCTTTT
```

The 6 reads collapse into 3 contigs listed below:
>ContigA(05a03.05a04)
```
GCACTTATAGCAGTAACACTCTATCCACATTGGAGGTTTTCTAAATATTTTATATTTTTG
CTTGTGGCGCTTGTCTAAAAAGCAGTAAAAACAATTACACAAATAATAAAACCCCTTTAA
GCATATGTCCCAGTCTTTTAAAATATACTCTTCAAAAACATCACCATAAACTTCTCCAAC
AAGCCTGTACTTTCTAGGGGGAAAGTTACAGCACAATTCTGTGCATTCTACCTGTGAAGA
ACTCCACACTTCATCTTCTTCATTTAGTTGGTGCACTGTACTAACACACTCTTGCAG
TTTTAAATATAAAGAATTAAGCTTTTTCATTTTTTCCTCATTTCCCCCTTTGTCAGG
```

>ContigB (06g03)
```
GTTGACACACATTTTTTTGACTTTTACTGTCTGAAAATAGTAAAGCATTTTTTTGATGTTC
CATATGAAGTCTATTATGAGTTGCATCTTCATTACTATTGCATTTTTCACACTCTTCTACC
TTAATAGATAGTTGTAAATATAATCCAAGTAATAAGTACACATCATCAATTCCTAATTCTA
AAGCAAATTCTGACAAAGCCTTCCAATTTAATTGATCTTTAAACTCCCCATATAAATCCTC
AGCTTTAAAATCATTTTCTTTTAAGCCACCAGGAATATTTTCTTCACATAAAGTAAATGGA
TCTCTAGTCATTCTACTATATAAACCATATGCATTATTAACACCTTTACAAAATAAAAAGC
TAATAGTACAGTATCCCTTACAAAAGTTATTAACAGCACTAACTCTATGTCTAAAAGGTGT
TAAAATAAACACAAGTGCAGTATTATAATAAGAATGTCTACTTGCAAAATTACATTTAAAC
TTACTTAAAAGTTTTTTATATAGGGTTTCTGCCTTTTCTTTGGTGGTATGTATTACAAATG
CAGTTAAAGTTCTATTACTAAATACAGCTTGAGACACAAATTCTTCCAATTCTTTAGGAAA
TGATAAAGATGCATCTGTAGCATTGTCCTTTTTTTTTTT
```

>ContigC(06h01.08f04.05h07)
```
TGGCTTATTAAACACCTGCTTATAAAGCAAATTTATAGTATATGGGTTTCTAACCCTTCT
TTGTCTAAAGTGTAGCCTAAAAAATCTGGAAAGCCCTGTATGTACCCTATTTTTGTTAAC
TCCCAAAAGGTCAGCACAAGTTATGTACAATCTACCTTGCAAGCAAAGAATGCCAATGCC
ATTTTCATCCAACAGTGGAATTGTGCTATTATTACTAAATGACACCACTGGTGGAGTTGC
AGCCCCTCCAACCATTCTGCCAAAGTATCTGCAGTTATCATTGCGGCTAGGGTCTGCCAC
CCATGATTCAATGCTGTACTTTTCATTAGTGACCCTTGCCCTGGGTGTTTCAGAACTGGA
ATAAACATGAGGCACAGTACCATTGGTTTTAGGATTTACAGTATACTGAGCAGGCCCCTT
GTATTTTTCAGTGGGAGCAAGTCCTAGCACATCCAAGGGCTGTCCTCCAACTGCCCAAAA
ATAAAGTTGGGGACCAGCAATACCTCCTACACCCCTGTAGTAAGTATGCCAGCATTAAG
CACAGGAAGCACCAAAACTTCTGTTTCCATTCTATACAGCTCCCATATAAGCATGTCACA
TTCACTAACCTGATTAGGAATATCAGGGGGAGCAACCTGTGACAAGCTGTAGCACACAGT
AGTATCGGCATCAGGAGTAACATTAGCAGCTTCAGCAGTTTTAAGTGGGCTACTAATAGA
CCAATAATGTGGGGTAGTCCCCTCTGCATTTCCAATAACAGGTTTAACAAACAATTCAA
```

FIGURE 4-2

SV40: 5' GCTCAGAGAGGCAGAGAGGCGGCCCTCGGCCTCTGCATAAATAAAAAAAATTAGTCAG
CGAGTCTCCGTCTCCGCCGAGCCCGGAGACGTATTTATTTTTTTAATCAGTC

WU: 5' AAGTTGAGGCTTTTTAGGCCTCTCAGGCCCTCCTTATTATAATAAAAAAAGCTAA 36
TTCAACTCCGAAAAATCCGGAGTCCGGAGGAATATATTATTTTTTTTCGATT
  |                |
  5213             5229 1
                   Nucleotide
                   position

FIGURE 5

Consensus Splice Donor and Acceptor Sites

```
Large T Donor
Baboon      TAGCTCTGAG GTTGGTTCTG
SV40        TGCAACTGAG GTATTTGCTT
JC          TAGTTCAGAG GTTGGTTGTG
BK          TAGCTCAGAG GTATGTGCTG
WU          CTCTTCACAG GTAGAATGCA Acceptor
Baboon      GTTTTTACAG GTGCCAACCT
SV40        TGTATTTTAG ATTCCAACCT
JC          TTTTTTTTAG GTGCCAACCT
BK          TTTTTTATAG GTGCCAACCT
WU          TTTATTATAG ATACCCACAT
```

```
Small T Donor
Baboon      AAACTCTAAG GTAACTAAGT
SV40        AAGCTCTAAG GTAAATATAA
JC          AAGCTTTAAG GTAAACCACT
BK          AAGCTTTAAG GTAACTAACT
WU          GCTTAACCAG GTAAGCATGT Acceptor
Baboon      GTTTTTACAG GTGCCAACCT
SV40        TGTATTTTAG ATTCCAACCT
JC          TTTTTTTTAG GTGCCAACCT
BK          TTTTTTATAG GTGCCAACCT
WU          TTTATTATAG ATACCCACAT
```

Putative Small T Antigen Forms

Non-Spliced Form: 194 AA — Start ATG ... Thr ACC ... Arg AGG Stop TAA

Spliced Form: 217 AA — Start ATG ... Thr ACC ... Arg AG|gtaagc ......... ttatag|A TAC CCA ... AAC TAA
                                                                                    Tyr Pro   Asn Stop 70 bp Intron Nucleotide Position: 5157, 4577, 4573, 4506, 4434

FIGURE 6

HUMAN POLYOMAVIRUS, DESIGNATED THE WU VIRUS, OBTAINED FROM HUMAN RESPIRATORY SECRETIONS

CROSS-REFERENCE TO RELATED APPLICATIONS

This application claims benefit of Provisional Application Ser. Nos. 60/900,502, filed 9 Feb. 2007, and 60/919,667, filed 22 Mar. 2007. The contents of these documents are incorporated herein by reference.

STATEMENT OF RIGHTS TO INVENTIONS MADE UNDER FEDERALLY SPONSORED RESEARCH

This invention is supported by Grant No. U54 AI057160 of the National Institutes of Health. The United States government may have certain rights in this invention.

REFERENCE TO SEQUENCE LISTING SUBMITTED VIA EFS-WEB

This application is being filed electronically via the USPTO EFS-WEB server, as authorized and set forth in MPEP §1730 II.B.2(a)(A), and this electronic filing includes an electronically submitted sequence (SEQ ID) listing. The entire content of this sequence listing is herein incorporated by reference for all purposes. The sequence listing is identified on the electronically filed .txt file as follows:

| File Name | Date of Creation | Size (bytes) |
| --- | --- | --- |
| 295002007200Seqlist.txt | Feb. 8, 2008 | 108,558 bytes |

TECHNICAL FIELD

This invention relates to virology and infectious disease. More particularly, the invention relates to a new human polyomavirus.

BACKGROUND ART

Viral infections of the respiratory tract are responsible for significant mortality and morbidity worldwide [1]. Despite extensive studies in the past decades that have identified a number of etiologic agents, including rhinoviruses, coronaviruses, influenza viruses, parainfluenzaviruses, respiratory syncytial virus and adenoviruses, approximately 30% of all cases cannot be accounted for by these agents suggesting that additional respiratory pathogens are likely to exist [2]. In fact, since 2001, six previously undescribed viruses have been identified by analysis of clinical specimens from the human respiratory tract: human metapneumovirus [3], SARS coronavirus [4], coronavirus NL63 [5], coronavirus HKU1 [6] and human bocavirus [7], and KI virus [35]. In some instances, new molecular methods such as VIDISCA [5], pan-viral DNA microarrays [8], and high throughput sequencing [7, 35], have played key roles in the identification of these agents. The advent of these new technologies has greatly stimulated efforts to identify novel viruses in the respiratory tract and in other human disease states.

Viruses in the family Polyomaviridae possess double stranded DNA genomes and infect a variety of avian, rodent and primate species. To date, two polyomaviruses, BK virus and JC virus, have been unambiguously described as human pathogens. BK and JC viruses are ubiquitous worldwide, and in adult populations seroprevalence rates approaching 75% and 100%, respectively have been reported [9]. Although human polyomaviruses have been suggested to utilize a respiratory route of transmission, detection of BK and JC polyomavirus nucleic acids in the respiratory tract has rarely been reported [10,11]. Infection with these two viruses is predominantly asymptomatic, although in the context of immunosuppression a number of syndromes have been clearly linked to these viruses. JC virus causes primary multifocal leukoencephalopathy while BK virus has been associated with a variety of renal disorders, most importantly tubular nephritis, which can lead to renal transplant failure and hemorrhagic cystitis in hematopoietic stem cell transplant recipients [12]. These viruses are believed to persist in a latent phase primarily in the kidney and can periodically undergo reactivation. Excretion of BK and JC viruses in urine has been reported in up to 20% of the general population [13][14]. Besides JC and BK virus, in the late 1950s, ~100 million people in the United States and many more worldwide may have been exposed to SV40, a polyomavirus that naturally infects rhesus monkeys, via contaminated polio vaccines, leading to widespread debate about whether or not SV40 is capable of sustained infection and replication cycles in humans [15].

Much of the interest in polyomaviruses and SV40 in particular derive from the transforming properties carried by the early transcriptional region of the viral genome that encodes for the small and large T antigens. T antigen is capable of binding both p53 and Rb proteins and interfering with their tumor suppressor functions. The early region alone is sufficient to transform established primary rodent cell lines [16] and in concert with telomerase and ras transforms primary human cells [17]. This has lead to controversy over whether any human tumors are associated with SV40 infection [18].

Identification of viruses associated with respiratory infections facilitates more accurate diagnosis and treatment and paves the way for new therapeutic options.

DISCLOSURE OF THE INVENTION

Provided here is a novel human polyomavirus, the WU virus, initially detected by high throughput sequencing of respiratory secretions from a patient suffering acute respiratory disease of unknown etiology. The virus was detected in the respiratory secretions from an additional 43 patients in two continents and the complete genomes of multiple isolates were sequenced.

Thus, in one aspect, provided herein is the WU virus that is phylogenetically related to known polyomaviruses. In a specific embodiment, the WU virus comprises, or alternatively consisting of, an isolated or recombinant nucleotide sequence of WU Virus (SEQ ID NO:1), WU-Strain_S1 (SEQ ID NO:2), WU-Strain_S2 (SEQ ID NO:3), WU-Strain_S3 (SEQ ID NO:4), WU-Strain_S4 (SEQ ID NO:5), or WU-Strain_S5 (SEQ ID NO:6), a complement thereof, or a portion thereof. In another embodiment, provided herein are isolated or recombinant nucleic acid molecules which hybridize under stringent conditions, as defined herein, to a nucleic acid molecule having the sequence of WU Virus (SEQ ID NO:1), WU-Strain_S1 (SEQ ID NO:2), WU-Strain_S2 (SEQ ID NO:3), WU-Strain_S3 (SEQ ID NO:4), WU-Strain_S4 (SEQ ID NO:5), or WU-Strain_S5 (SEQ ID NO:6), a complement thereof, or a portion thereof. Further provided herein are isolated polypeptides or proteins that are encoded by a nucleic acid molecule comprising, consisting essentially of or consisting of, he nucleotide sequence of WU Virus (SEQ ID NO:1), WU-Strain_S1 (SEQ ID NO:2), WU-Strain_S2 (SEQ ID NO:3), WU-Strain_S3 (SEQ ID NO:4), WU-Strain_S4 (SEQ ID NO:5), or WU-Strain_S5 (SEQ ID NO:6), a complement thereof, or a portion thereof. Such proteins include the small T antigen (STAg) (spliced and non-spliced forms), the large T antigen (LTAg), VP1, VP2, or VP3 of the WU virus.

In another aspect, provided herein are methods to the use of the sequence information of the isolated virus for diagnostic and therapeutic methods. In one embodiment, provided herein is the nucleotide sequence of WU Virus (SEQ ID NO:1), WU-Strain_S1 (SEQ ID NO:2), WU-Strain__S2 (SEQ ID NO:3), WU-Strain_S3 (SEQ ID NO:4), WU-Strain_S4 (SEQ ID NO:5), or WU-Strain_S5 (SEQ ID NO:6), a complement thereof, or a portion thereof in detection and diagnostic assays. Also provided are nucleic acid molecules which are suitable for use as primers and/or probes consisting of or comprising a portion of the nucleotide sequence of WU Virus (SEQ ID NO:1), WU-Strain_S1 (SEQ ID NO:2), WU-Strain_S2 (SEQ ID NO:3), WU-Strain_S3 (SEQ ID NO:4), WU-Strain_S4 (SEQ ID NO:5), or WU-Strain_S5 (SEQ ID NO:6), or a complement thereof. Further provided are chimeric or recombinant viruses or viral proteins encoded by the nucleotide sequences disclosed herein.

In yet another aspect, provided herein are antibodies that specifically bind a polypeptide encoded by the nucleotide sequence of WU Virus (SEQ ID NO:1), WU-Strain_S1 (SEQ ID NO:2), WU-Strain_S2 (SEQ ID NO:3), WU-Strain_S3 (SEQ ID NO:4), WU-Strain_S4 (SEQ ID NO:5), or WU-Strain_S5 (SEQ ID NO:6), a complement thereof, or a portion thereof. Further provided are antibodies that specifically bind to a polypeptide of the VP1 (SEQ ID NO:51), VP2 (SEQ ID NO:52), VP3 (SEQ ID NO:53), large T antigen (SEQ ID NO:54), non-spliced small T antigen (SEQ ID NO:55), and spliced small T antigen (SEQ ID NO:57). Such antibodies include, but are not limited to polyclonal, monoclonal, bi-specific, multi-specific, human, humanized, chimeric, single chain antibodies, diabodies, nanobodies, single domain antibodies (e.g., camel antibodies), Fab, $F(ab')_2$, Fvs, intrabodies and fragments containing either a $V_L$ or $V_H$ domain or even a complementary determining region (CDR) that specifically binds to a polypeptide of the WU virus disclosed herein.

In another aspect, provided herein are pharmaceutical compositions comprising recombinant and/or chimeric forms of WU virus, subunits, or individual proteins of the virus.

BRIEF DESCRIPTION OF THE DRAWINGS

FIG. 1 shows a schematic of WU virus genome organization.

FIG. 2 illustrates the phylogenetic analysis of WU Virus. Amino acid based phylogenetic trees were generated using the Neighbor Joining method with 1000 bootstrap replicates. Significant bootstrap values are shown. A) Small T Antigen; B) Large T Antigen; C) VP1; D) VP2.

FIG. 3 shows the strain variation of WU virus. A 250 bp fragment of the VP2 gene was aligned using ClustalX. WU indicates the original case, and strain designations correspond to patients as listed in Table 4.

FIG. 4 (SEQ ID NOS:103-111) shows the initial shotgun sequencing reads with homology to polyomaviruses.

FIG. 5 shows a comparison of SV40 (SEQ ID NO:112) and WU Virus (SEQ ID NO:113) replication origin region. The consensus TAg binding motif is GAGGC. The known primate polyomaviruses SV40, JC, BK and baboon polyomavirus all have 4 copies of the copies of the binding site oriented as shown above for SV40 (NC__001669). The first nucleotide of the 3rd copy of the consensus TAg binding site is defined as nucleotide 1 for WU and SV40. Differences between SV40 and WU Virus are: 1) one of the TAg binding sites in WU virus appears to be a non-canonical TAGGC; 2) the second and third consensus TAg binding sites in WU virus overlap; 3) the nucleotide spacing between the TAg binding sites in WU virus varies from the prototype SV40 as shown. Shown in blue is the polyA/T tract that is commonly found to the late side of the origin in polyomaviruses.

FIG. 6 (SEQ ID NOS:114-133) shows the predicted splice sites for Large and Small T Antigen. A consensus Large T donor site was detected. Splicing to the consensus downstream acceptor would generate a Large T antigen of 648 amino acids. For Small T Antigen, an unspliced open reading frame of 194 amino acids was identified. A predicted slice donor site was also detected that would result in excision of a 70 nucleotide intron and production of a 217 amino acid open reading frame.

FIG. 7 depicts the locations of original shotgun reads. Locations of all sequencing primers are mapped to the complete genome. Primers used for amplification are shown in lighter type.

MODES OF CARRYING OUT THE INVENTION

In one aspect, provided herein is an isolated human polyomavirus comprising, consisting essentially of, or consisting of the nucleotide sequence of WU Virus (SEQ ID NO:1), WU-Strain_S1 (SEQ ID NO:2), WU-Strain_S2 (SEQ ID NO:3), WU-Strain_S3 (SEQ ID NO:4), WU-Strain_S4 (SEQ ID NO:5), or WU-Strain_S5 (SEQ ID NO:6), a complement thereof, or a portion thereof (as shown in the Table 1. The nucleic acid sequence of the WU human polyomavirus can be isolated, purified, and/or recombinant. An isolated and/or purified nucleic acid molecule is one which is separated from other nucleic acid molecules which are present in the natural source of the nucleic acid molecule. It can be substantially free of other cellular material, or culture medium when produced by recombinant techniques, or substantially free of chemical precursors or other chemicals when chemically synthesized.

TABLE 1

| |
|---|
| >WUVirus |
| gcctcaggcctccttattataataaaaaaaagctaagcatgattgacagtgtgggctaaaccaaaagcac |
| aagaacaaagcttttagccaattagcagccacaaggtggagcaaaagtattaagtttcactgttatgtgc |
| aggaatgtgcagctgtgacctttttaaagtttccgggcacggcgccaacttcctgggcctggtgccatacc |
| aacacagctgctgagcttccggaatacaatactggtgccctttgtaagtgttttacaggtaagtaaggcc |
| tacaacagggcttatttgtactataagttaatgggggccctttgtagtccagcggaaagtgaagggtggc |
| ttaacagagacgtccttgggttcaaacctaagggtgccataagcaacattacattaatgttgtgacatct |
| ccagtcgggggtattggcctataggaaaccctagggctctataagcagcatacatatgttgtgacatctc |
| cgttgagtctgggggtattggtgctaccgtctcgaacctagccgacagccgttggatataaagggtcacc |
| atttttatttcagatgggcatattgcttgctgtgcctgaaataattgctgcatctgtagctggaggagca |
| gaggcactatcaattgctggatctggagctgcaatagcaactggtgaaggtttagctgctcttggtgggc |
| ttacagagtcagcagcactattaggggaaactgttgaaatatctgaagcagctgctactgtactaacaaa |

TABLE 1-continued

```
agtacctgagcttgtaactgtaacacaaggtgtaacagcagctgtacaaggggtgcaggtcttgtaggt
ggtatatatacagctttagcagcagatcgccctggggacctgcctgcgagtaccccaacaggaagtccaa
gtggactacatcccccgcaggatacaatcccccaaggaggtggacttaatatccagtccatccacaagcc
cctccacgcccctacccaggaatggcactggcacctatccctgaatacaacttggaaactggaattcca
gggtcccggactgggtattcaacttcattgcatcccacctgcccgagttgcctagcctgcaggacgtgt
tcaatagaattgcctatggaatctggacatcatattacaatacggggagaacagtagttaatagagcagt
tagtgaagaattacaaagactactaggagatttagaatatggatttagaactgcacttgccaccattggg
gaatctgacccagtaaatgctatagttgaacaagtaagaagctttgttagtggaggaagagaaagagaac
tgttacaaatagctgcaggtcaacctgtagacatttctgaaggtgtatcaagaggcacagctactatttc
aaatgctgtagaagctgtaagagatgcaactcaaagactatcacaagcaacctacaactttgtttatgat
gcttctacccttccaagggatggctttaatgcacttagtgatggagttcacagactaggccagtggattt
caatgcctgggctacaggggtactcccattatgcagccctgactggatttatatgtacttgaaga
gctaaacagtgacatttctaaaattcctacacagggaattaaaagaaaactacaacaaaatggcctgcac
agcaaagccagcctgcacagcaaaaccaggaaggtcaccaagaagtcaacccacaagagtgcaaagcctt
ccaaaacaagtcagaaaaggagggggtagacgtgctggccgccgtaccactgtcagaagaaacagagttta
aagttgaattgtttgttaaacctgttattggaaatgcagaggggactaccccacattattggtctattag
tagcccacttaaaactgctgaagctgctaatgttactcctgatactactgtgtgctacagcttg
tcacaggttgctcccctgatattcctaatcaggttagtgaatgtgacatgcttatatggggagctgtata
gaatggaaacagaagttttggtgcttcctgtgcttaatgctggcatacttactacaggggtgtaggagg
tattgctggtccccaactttatttttgggcagttggaggacagccctggatgtgctaggacttgctccc
actgaaaaatacaaggggcctgctcagtatactgtaaatcctaaaaccaatggtactgtgcctgtttt
attccagttctgaaacaccagggcaaggtcactaatgaaaagtacagcattgaatcatgggtggcaga
ccctagccgcaatgataactgcagatactttggcagaatggttggaggggctgcaactccaccagtggtg
tcatttagtaataatagcacaattccactgttggatgaaaatggcattggcattcttgcttgcaaggta
gattgtacataacttgtgctgaccttttgggagttaacaaaaatagagtacatacaggggcttttccagatt
ttttaggctacactttagacaaagaagggttagaaacccatatactataaatttgctttataagcaggtg
tttaataagccagctgatgacattagtgggcaactgcaggttacagaggttactatgactgaagaaacag
ggcccttgcctcccacagtagagggaaatgttggtgtacccacaaccagtaatttgtctcatttgcctgc
aactgtaactttacaagccacaggcccaatactaaacacacaaggaataatgtaataaatgcagtttatta
ataaagcaattttaagcattgtgtttttcaagtatgttgcatccatttgttacattcatttgcatgtcag
caaattcagtaaggcctatatatttgtctaacagttcttccaatacacaactttagcttgtatacatgg
gtgaaaatcactaacaggcctgcaccatattaacataattaaaatacacattccactttgtaaaactctt
tttaccattagttctggagttttatccagacttttcttttaagtgtcttttgggtgtaaaaagtacagttt
tatgaaatctaggagccaaagtagcagggactaaatattcattcattgttacaatacctggaggaaaaat
ttgtgacctttttatttaaatgttttttttctaaattaacttaacacttccatctaaatagtctcttaaa
ttatctaagttactcattccatttccagatggtaacagtttattatctcctacttgacctttacatctt
```

WU_Full_Genomes

```
caaatactactgtaaattgatctattgcaactcctaactcaaagtttaatctatcagctggaatattaat
atttaaggcctttcctccacaaaggtcaagtaaagcagcagcaacagttgttttaccactgtttataggc
cccttaaaaacccaataccttttttaggtacattttcaactaataattttaggtacctgtatacaagct
catctattttaccatttaggcctaaataccaggctacaccagccatatataataaaacatcttgctcacc
tttaatagttttatccatttttgtccagtatttttttcaaatcttctagctaataaatcttctctggacata
tttaaactatctaccccttctttttgcaataaccacatcaatagcctgttgacacacatttttttgacttt
tactgtctgaaaatagtaaagcattttttgatgttccatatgaagtctattatgagttgcatcttcatt
actattgcattttttcacactcttctaccttaatagatagttgtaaatataatccaagtaataagtacaca
tcatcaattcctaattctaaagcaaattctgacaaagccttccaatttaattgatcttaaactccccat
ataaatcctcagctttaaaatcattttcttttaagccaccaggaatattttcttcacataaagtaaatgg
atctctagtcattctactatataaaccatatgcattattaacacctttacaaaataaaagctaatagta
cagtatcccttacaaaagttattaacagcactaactctatgtctaaaaggtgttaaaataaacacaagtg
cagtattataatagaatgtctacttgcaaaattacatttaaactttacttaaaagttttttatataggggt
ttctgccttttctttggtggtatgtattacaaatgcagttaaagttctattactaaatacagcttgagac
acaaattcttccaattcttaggaaatgataaagatgcatctgtagcattgtccttttttttttaggtg
gtgttgcctgtgaacattgtggttcctcatcatcttctctagtacgctttgtagggggtttctccaggaga
tttaggcatttcctcattacatcttagttcttcttcccagtaggaattaaactgagaccaccagtaatcc
cagtctggggtaccatatgtgggtatctataataaaaaaaaattattaatttacttataaaacataaaag
taccctataataaaaacatgcttacctggttaagccaacccttgcatggttgtaagaaatataatctt
tttccagtaaaaaatgtttctgcactaatttcaaagccaaaccactctctatagcacctgtagcagtaa
cactctatccacattggaggttttctaaatattttatattttgcttgtggcgcttgtctaaaaagcagt
aaaaacaattacacaaataataaaaaccccttaagcatatgtcccagtctttaaaatatactcttcaaa
aacatcaccataaacttctccaacaagcctgtactttctagggggaaagttacagcacaattctgtgcat
tctacctgtgaagagctccacacttcatcttcttcttcatttagttggtgactgtactaacacactctt
gcagttttaaatataaagaattaagctttttcattttttcctcatttccccctttgtcaggatgaaattc
tttgcatttgctaaggtattttgttctcattagtggtaaatttccccagcaggtcatatcaagacccagc
agctgcataagttctttgcttcatttctggacaaagttttatccattttgccttctttagcctcaaggc
gcctcagcaaggccctctgcttttagttcagaaagttgaggcttttag
```

>WU-Strain_S1
```
gcctcaggcctccttattataataaaaaaagctaagcatgattgacagtgtgggctaaaccaaaagcac
aagaacaaagcttttagccaattagcagccacaaggtggagcaaagtattaagtttcactgttatgtgc
aggaatgtgcagctgtgacctttaaagtttccgggcacggcgccaacttcctgggcctggtgccatacc
aacacagctgctgagcttccggaatacaatactggtgcccttttgtaagtgttttacaggtaagtaaggcc
tacaacagggcttatttgtactataagttaatgggggccctttgtagtccagcggaaagtgaagggtggc
ttaacagagacgtccttgggttcaaacctaaagggtgccataagcaacattacttaatgttgtgacatct
ccagtcgggggtattggcctataggaaaccctagggctctataagcagcatacatatgttgtgacatctc
cgttgagtctgggggtattggtgctaccgtctcgaacctagccgacagccgttggatataaagggtcacc
attttttatttcagatgggcatattgcttgctgtgcctgaaataattgctgcatctgtagctggaggagca
gaggcactatcaattgctggatctggagctgcaatagcaactggtgaaggtttagctgctcttggtgggc
ttacagagtcagcagcactattaggggaaactgttgaaatatctgaagcagctgctactgtactaacaaa
```

TABLE 1-continued

```
agtacctgagcttgtaactgtaacacaaggtgtaacagcagctgtacaaggggggtgcaggtcttgtaggt
ggtatatatacagctttagcagcagatcgccctggggacctgcctgcgagtaccccaacaggaagtccaa
gtggactacatcccccccgcaggatacaatcccccaaggaggtggacttaatatccagtccatccacaagcc
cctccacgcccccctacccaggaatggcactggcacctatccctgaatacaacttggaaactggaattcca
ggggtcccggactgggtattcaacttcattgcatcccacctgcccgagttgcctagcctgcaggacgtgt
tcaatagaattgcctatggaatctggacatcatattacaatacggggagaacagtagttaatagagcagt
tagtgaagaattacaaagactactaggagatttagaatatggatttagaactgcacttgccaccattggg
```

WU_Full_Genomes

```
gaatctgacccagtaaatgctatagttgaacaagtaagaagctttgttagtggaggaagacaaagagaac
tgttacaaatagctgcaggtcaacctgtagacatttctgaaggtgtatcaagaggcacagctactatttc
aaatgctgtagaagctgtaagagatgcaactcaaagactatcacaagcaacctacaactttgtttatgat
gcttctacccttccaagggatggctttaatgcacttagtgatggagttcacaggctaggccagtggattt
caatgcctgggggctacagggggtactccccattatgcagcccctgactggatttatatgtacttgaaga
gctaaacagtgacatttctaaaattcctacacaggaattaaaagaaaactacaacaaaatggcctgcac
agcaaagccagcctgcacagcaaaaccaggaaggtcaccaagaaggtcaacccacaagagtgcaaagcctt
ccaaaacaagtcagaaaaggaggggtagacgtgctggccgccgtaccactgtcagaagaaacagagttta
aagttgaattgtttgttaaacctgttattggaaatgcagaggggactaccccacattattggtctattag
tagcccacttaaaactgctgaagctgctaatgttactcctgatgctgatactactgtgtgctacagcttg
tcacaggttgctcccccctgatattcctaatcaggttagtgaatgtgacatgcttatatgggagctgtata
gaatggaaacagaagttttggtgcttcctgtgcttaatgctggcatacttactacagggggtgtaggagg
tattgctggtcctcaacttatttttgggcagttggaggacagcccttggatgtgctaggacttgctccc
actgaaaaatacaagggggcctgctcagtatactgtaaatcctaaaaccaatggtactgtgcctcatgttt
attccagttctgaaacacccagggcaagggtcactaatgaaaagtacagcattgaatcatgggtggcaga
ccctagccgcaatgataactgcagatactttggcagaatggttggaggggctgcaactccaccagtggtg
tcatttagtaataatagcacaattccactgttggatgaaaatggcattggcattcttgcttgcaaggta
gattgtacataacttgtgctgaccttgggagttaacaaaaatagagtacatacagggctttccagatt
tttaggctacactttagacaaagaaggggttagaaacccatatactataaattttgctttataagcaggtg
tttaataagccagctgatgacattagtgggcaactgcaggttacagaggttactatgactgaagaaacag
ggcccttgcctcccacagtagagggaaatgttggtgtacccacaaccagtaatttgtctcatttgcctgc
aactgtaacttttacaagccacaggcccaatactaaacacacaaggataatgtaataaatgcagtttatta
ataaagcaattttaagcattgtgttttttcaagtatgttgcatccatttgttacattcatttgcatgtcag
caaattcagtaaggcctatatatttgtctaacagttcttccaatacacaacttttaggcttgctatacatgg
gtgaaaatcactaacaggcctgcaccatattaacataagtaaaatacacattccactttgtaaaactctt
tttaccattagttctggagtttttatccagactttcttttaagtgtcttttgggtgtaaaaagtacagttt
tatgaaatctaggagccaaagtagcagggactaaatattcattcattgttacaatacctggaggaaaaat
ttgtgaccttttatttaaatgttttttttctaaattaacttttaacacttccatctaaatagtctcttaaa
ttatctaagttactcattccatttccagatggtaacagtttattatctcctacttgacctttttacatctt
caaatactactgtaaattgatctattgcaactcctaactcaaagtttaatctatcagctggaatattaat
atttaaggccttcctccacaaaggtcaagtaaagcagcagcaacagttgtttaccactgtttatagggc
cccttaaaaaacccaataccttttttaggtacatttttcaactataactttttaggtacctgtatacaagct
catctattttaccatttaggcctaaataccaggctacaccagccatatataataaaaacatcttgctcacc
tttaatagttttatccatttttgtctagtattttttcaaatcttctagctaataaatcttctctggacata
tttaaactatctacccttcttttttgcaataaccacatcaatagcctgttgacacacatttttttgactttt
tactgtctgaaaatagtaaagcattttttttgatgttccatatgaagtctattatgagttgcatctttcatt
actattgcattttttcacactcttctaccttaatagatagttgtaaatataatccaagtaataagtacaca
tcatcaattcctaattctaaagcaaattctgacaaagcctttccaatttaattgatctttaaactccccat
ataaatcctcagctttaaaatcattttcttttaagccaccaggaatattttcttcacataaagtaaatgg
atctctagtcattctactatataaaccatatgcattattaacacctttacaaaataaaagctaatagta
cagtatccctttacaaaagttattaacagcactaactctatgtctaaaaggtgttaaaataaacacaagtg
cagtattataataagaatgtctacttgcaaaattacatttaaacttacttaaaagttttttatatagggt
ttctgccttttctttggtggtatgtattacaaatgcagttaaagttctattactaaatacagcttgagac
acaaattcttccaattcttttaggaaatgataaagatgcatctgtagcattgtcctttttttttttaggtg
gtgttgcctgtgaacattgtggttcctcatcatcttctctagtacgcttttgtaggggtttctccaggaga
tttaggcatttcctcattacatcttagttcttcttcccagtaggaattaaactgagaccaccagtaatcc
cagtctggggtaccatatgtgggtatctataataaaaaaaagttattaatttacttataaaacataaaag
taccccctataataaaaacatgcttacctggttaagccaacccccttgcatggttgtaagaaatataatctt
```

WU_Full_Genomes

```
tttccagtaaaaaaatgtttctgcactaatttcaaagccaaaccactctctatagcacctgtagcagtaa
cactctatccacattggaggttttctaaatattttatattttttgcttgtggcgcttgtctaaaaagcagt
aaaaacaattacacaaataataaaaaccccttttaagcatatgtcccagtctttttaaaatatactcttcaaa
aacatcaccataaacttctccaacaagcctgtactttctagggggaaagttacagcacaattctgtgcat
tctacctgtgaagagctccacacttcatcttcttcttcatttagttggtgcactgtactaacacactctt
gcagttttaaatataaagaattaagcttttcattttttcctcattttcccccctttgtcaggatgaaattc
tttgcatttgctaaggtattttgttctcattagtggtaaatttccccagcaggtcatatcaagacccagc
agctgcataagttcttttgcttcatttctggacaaagtttatccatttttgccttctttagcctcaaggc
gcctcagcaaggccctctgcttttagttcaaaaaggtgaggcttttag
```

>WU-Strain_S2
```
gcctcaggcctccttattataataaaaaaagctaagcatgattgacagtgtgggctaaaccaaaagcac
aagaacaaagcttttagccaattagcagccacaaggtggagcaaaagtattaagtttcactgttatgtgc
aggaatgtgcagctgtgaccttttaaagtttccgggcacggcgccaacttcctggcgcttgtctgccatacc
aacacagctgctgagcttccggaatacaatactggtgcccttctgtaagtgtttacaggtaagtaaggcc
tacaacagggcttatttgtactataagttaatgggggccctttgtagtccagcggaaagtgaagggtggc
ttaacagagacgtccttgggttcaaacctaagggtgccataagcaacattacattaatgttgtgacatct
ccagtcgggggtattggcctataggaaaccctagggctctataagcagcatacatatgttgtgacatctc
cgttgagtctgggggtattggtgctaccgtctcgaacctagccgacagccgttggatataaagggtcacc
```

TABLE 1-continued

```
attttttatttcagatgggcatattgcttgctgtgcctgaaataattgctgcatctgtagctggaggagca
gaggcactatcaattgctggatctggagctgcaatagcaactggtgaaggtttagctgctcttggtgggc
ttacagagtcagcagcactattaggggaaactgttgaaatatctgaagcagctgctactgtactaacaaa
agtacctgagcttgtaactgtaacacaaggtgtaacagcagctgtacaaggggtgcaggtcttgtaggt
ggtatatatacagctttagcagcagatcgccctggggacctgcctgcaagtaccccaacaggaagtccaa
gtggactacatcccccccgcaggatacaatccccaaggaggtggacttaatatccagtccatccacaagcc
cctccacgcccctacccaggaatggcactggcacctatccctgaatacaacttggaaactggaattcca
ggggtccccggactgggtattcaacttcattgcatcccacctgcccgagttgcctagcctgcaggacgtgt
tcaatagaattgcctatggaatctggacatcatattacaatacgggggagaacagtagttaatagagcagt
tagtgaagaattacaaagactactaggagatttagaatatggatttagaactgcacttgccaccattggg
gaatctgacccagtaaatgctatagttgaacaagtaagaagctttgttagtggaggaagacaaagagaac
tgttacaaatagctgcaggtcaacctgtagacatttctgaaggtgtatcaagaggcacagctactatttc
aaatgctgtagaagctgtaagagatgcaactcaaagactatcacaagcaacctacaactttgtttatgat
gcttctaccccttccaagggatggctttaatgcacttagtgatggagttcacaggctaggccagtggattt
caatgcctgggctacaggggtactcccattatgcagccctgactggatttatatgtacttgaaga
gctaaacagtgactttctaaaattcctcacacagggaattaaaagaaaactacaacaaaatggcctgcac
agcaaagccagcctgcacagcaaaaccaggaaggtcaccaagaagtcaacccacaagagtgcaaagcctt
ccaaaacaagtcagaaaaggaggggtagacgtgctggccgccgtaccactgtcagaagaaacagagttta
aagttgaattgtttgttaaacctgttattggaaatgcagaggggactaccccacattattggtctattag
tagcccacttaaaactgctgaagctgctaatgttactcctgatgctgatactactgtgtgctacagcttg
tcacaggttgctccccctgatattcctaatcaggttagtgaatgtgacatgcttatacgggagctgtata
gaatggaaacagaagttttggtgcttcctgtgcttaatgctggcatacttactacaggggtgtaggagg
tattgctggtcctcaacttattttgggcagttggaggacagcccttggatgtgctaggacttgctccc
actgaaaaatacaaggggcctgctcagtatactgtaaatcctaaaaccaatggtactgtgcctcatgttt
attccagttctgaaacacccagggcaagggtcactaatgaaaagtacagcattgaatcatgggtggcaga
ccctagccgcaatgataactgcagatactttggcagaatggttggagggggctgcaactccaccagtggtg
tcatttagtaataatagcacaattccactgttggatgaaaatggcattggcattctttgcttgcaaggta
gattgtacataacttgtgctgacctttttgggagttaacaaaaatagagtacatacagggctttccagatt
ttttaggctacactttagacaaagaagggttagaaacccatatactataaatttgctttataagcaggtg
```

WU_Full_Genomes

```
tttaataagccagctgatgacattagtgggcaactgcaggttacagaggttactatgactgaagaaacag
ggccttgcctcccacagtagagggaaatgttggtgtaccacaaccagtaatttgtctcatttgcctgc
aactgtaactttacaagccacaggcccaatactaaacacacaaggataatgtaaataaatgcagtttatta
ataaagcaattttaagcattgtgttttcaagtatgttgcatccatttgttacattcatttgcatgtcag
caaattcagtaaggcctatatatttgtctaacagttctttccaatacacaactttagcttgtatacatgg
gtgaaaatcactaacaggcctgcaccatattaacataagtaaaatagcatttccactttgtaaaactctt
tttaccattagttctggagttttatccagactttcttttaagtgtcttttgggtgtaaaaagtacagttt
tatgaaatctaggagccaaagtagcagggactaaatattcattcattgttacaatacctggaggaaaaat
ttgtgacctttttatttaaatgttttttttctaaattaactttaacactttcatctaaatagtctcttaaa
ttatctaagttactcattccatttccagatggtaacagtttattatctcctacttgaccttttacatctt
caaatactactgtaaattgatctattgcaactcctaactcaaagtttaatctatcagctggaatattaat
atttaaggcctttcctccacaaaggtcaagtaaagcagcagcaacagttgttttaccactgtttataggc
cccttaaaaacccaatacctttttttaggtacattttcaactataactttttagatacctgtatacaagct
catctattttaccattaggcctaaataccaggctacaccagccatatataataaaacattgctcacc
tttaatagttttatccattttgtccagtattttttcaaatcttctagctaataaatcttctctggacata
tttaaactatctacccttcttttttgcaataaccacatcaatagcctgttgacacacattttttttgacttt
tactgtctgaaaatagtaaagcatttttttttgatgttccatatgaagtctattatgagttgcatcttcatt
actattgcattttttcacactcttctaccttaatagatagttgtaaatataatccaagtaataagtacaca
tcatcaattcctaattctaaagcaaattctgacaaagcctcccaatttaattgatctttaaactccctat
ataaatcctcagctttaaaatcattttctttttaagccaccaggaatattttcttcacataaagtaaatgg
atctctagtcattctactatataaaccatatgcattattaacaccctttacaaaataaaaagctaatagta
cagtatcccttacaaaagttattaacagcactaactutatgtctaaaaggtgttaaaataaacacaagtg
cagtattaataagaatgtctacttgcaaaattacattttaaacttacttaaaagtttttttatatagggt
ttctgcctttttctttggtggtatgtattacaaatgcagttaaagttctattactaaatacagcttgagac
acaaattcttccaattctttaggaaatgataaagatgcatctgtagcattgtcctttttttttttaggtg
gtgttgcctgtgaacattgtggttcctcatcatcttctctagtacgctttgtaggggtttctccaggaga
tttaggcatttcctcattacatcttagttcttcttcccagtaggaattaaactgagaccaccagtaatcc
cagtctgggtaccatatgtgggtatctataataaaaaaaagttattaatttacttataaaacataaaag
taccccctataataaaaacatgcttacctggttaagccaacccettgctggttgtaagaaatataatctt
tttccagtaaaaaaatgttctgcactaatttcaaagccaaaccactctctatagcacctgtagcagtaa
cactctatccacattggaggttttctaaatattttataatttttgcttgtggcgcttgtctaaaaagcagt
aaaaacaattacacaaataataaaaacccctttaagcatatgtcccagtcttttaaaatatactcttcaaa
aacatcaccataaacttctccaacaagcctgtactttctagggggaaagtttacagcacaattctgtgcat
tctacctgtgaagagctccacacttcatcttcttcttcatttagttggtgcactgtactaacacactctt
gcagttttaaatataaagaatttaagcttttttcatttttttcctcatttcccccttttgtcaggatgaaattc
tttgcatttgctaaggtattttgttctcattagtggtaaatttccccagcaggtcatatcaagacccagc
agctgcataagttcttttgcttcatttctggacaaagttttatccattttgccttcttttagcctcaaggc
gcctcagcaaggccctctgcttttagttcaaaaaggtgaggcttttag
```

>WU-Strain_S3
```
gcctcaggcctccttattataataaaaaaagctaagcatgattgacagtgtgggctaaaccaaaagcac
aagaacaaagcttttagccaattagcagccacaaggtgggagcaaaagtattaagtttcactgttatgtgc
aggaatgtgcagctgtgacctttaaagtttccgggcacggcgccaacttcctggcctggtgccatacc
aacacagctgctgagcttccggaatacaatactggtgcctttctgtaagtgttttacaggtaagtaaggcc
tacaacagggccttatttgtactataagttaatgggggccctttgtagtccagcggaaagtgaagggtggc
ttaacagagacgtccttgggttcaaacctaagggtgccataagcaacattacattaatgttgtgacatct
ccagtcgggggtattggcctataggaaaccctaggctctataagcagcatacatatgttgtgacatctc
cgttgagtctgggggtattggtgctaccgtctcgaacctagccgacagccgttggatataaagggtcacc
```

TABLE 1-continued

WU_Full_Genomes

```
attttatttcagatgggcatattgcttgctgtgcctgaaataattgctgcatctgtagctggaggagca
gaggcactatcaattgctggatctggagctgcaatagcaactggtgaaggtttagctgctcttggtgggc
ttacagagtcagcagcactattaggggaaactgttgaaatatctgaagcagctgctactgtactaacaaa
agtacctgagcttgtaactgtaacacaaggtgtaacagcagctgtacaaggggggtgcaggtcttgtaggt
ggtatatatacagctttagcagcagatcgccctggggacctgcctgcgagtaccccaacaggaagtccaa
gtggactacatcccccccgcaggataacaatccccaaggaggtggacttaatatccagtccatccacaagcc
cctccacgcccccctacccaggaatggcactggcacctatccctgaatacaacttggaaactggaattcca
ggggtcccggactgggtattcaacttcattgcatcccacctgcccgagttgcctagcctgcaggacgtgt
tcaatagaattgcctatggaatctggacatcatattacaatacggggagaacagtagttaatagagcagt
tagtgaagaattacaaagactactaggagatttagaatatggatttagaactgcacttgccaccattggg
gaatctgacccagtaaatgctatagttgaacaagtaagaagctttgttagtggaggaagacaaagagaac
tgttacaaatagctgcaggtcaacctgtagacatttctgaaggtgtatcaagaggcacagctactatttc
aaatgctgtagaagctgtaagagatgcaactcaaagactatcacaagcaacctacaactttgtttatgat
gcttctaccctcccaagggatggctttaatgcacttagtgatggagttcacaggctaggccagtggattt
caatgcctgggctacaggggggtactcccattatgcagccctgactggattttatatgtacttgaaga
gctaaacagtgacatttctaaaattcctacacagggaattaaaagaaaactacaacaaaatggcctgcac
agcaaagccagcctgcacagcaaaccaggaaggtcaccaagaagtcaacccacaagagtgcaaagcctt
ccaaaacaagtcagaaaaggaggggtagacgtgctggccgccgtaccactgtcagaagaaacagagttta
aagttgaattgtttgttaaacctgttattggaaatgcagaggggactaccccacattattggtctattag
tagcccacttaaaactgctgaagctgctaatgttactcctgatgctgatactactgtgtgctacagcttg
tcacaggttgctccccctgatattcctaatcaggttagtgaatgtgacatgcttatatgggagctgtata
gaatggaaacagaagttttggtgcttcctgtgctaatgctggcatactactacagggggtgtaggagg
tattgctggtcctcaactttattttgggcagttggaggacagccctggatgtgctaggacttgctccc
actgaaaaatacaaggggcctgctcagtatactgtaaatcctaaaaccaatggtactgtgcctcatgttt
attccagttctgaaacacccagggcaagggtcactaatgaaaagtacagcattgaatcatgggtggcaga
ccctagccgcaatgataactgcagatactttggcagaatggttggaggggctgcaactccaccagtggtg
tcatttagtaataatagcacaattccactgttggatgaaaatggcattggcatcttttgcttgcaaggta
gattgtacataacttgtgctgacctttgggagttaacaaaaatagagtacatacagggctttccagatt
ttttaggctacactttagacaaagaagggttagaaacccatatactataaatttgctttataagcaggtg
tttaataagccagctgatgacattagtgggcaactgcaggttacagaggttactatgactgaagaaacag
ggccttgcctcccacagtagagggaaatgttggtgtaccacacaccagtaatttgtctcatttgcctgc
aactgtaactttacaagccacaggcccaatactaaacacacaaggataatgtaataaatgcagttttta
ataaagcaattttaagcattgtgtttttcaagtatgttgcatccatttgttacattcatttgcatgtcag
caaattcagtaaggcctatatatttgtctaacagttcttccaatacacaactttagcttgtatacatgg
gtgaaaatcactaacaggcctgcaccatattaacataagtaaaatcacattccacttttgtaaaactctt
tttaccattagttctggagttttatccagactttcttttaagtgtcttttgggtgtaaaaagtacagttt
tatgaaatctaggagccaaagtagcagggactaaatattcattcattgttacaataccttggaggaaaat
ttgtgacctttatttaaatgtttttttctaaattaactttaacacctccatctaaatagtctcttaaa
ttatctaagttactcattccattcccagatggtaacagtttattatctcctacttgaccttttacatctt
caaatactactgtaaattgatctattgcaactcctaactcaaagtttaatctatcagctggaatattaat
atttaaggcctttcctccacaaaggtcaagtaaagcagcagcaacagttgttttaccactgtttataggc
cccttaaaaacccaataccttttttaggtacattttcaactataacttttaggtacctgtatacaagct
catctattttaccatttaggcctaaatacaggctacaccagccatatataatataaaaacatcttgctcacc
tttaatagttttatccattttgtccagtattttttcaaatcttctagctaataaatcttctctggacata
tttaaactatctaccctctttttgcaataaccacaccaatagcctgttgacacacattttttgacttt
tattgtctgaaaatagtaaagcattttttgatgttccatatgaagtctattatgagttgcatcttcatt
actattgcattttcacactcttctaccttaatagatagttgtaaatataatccaagtaataagtacaca
tcatcaattcctaattctaaagcaaattctgacaaagccttccaatttaattgatctttaaactccccat
```

WU_FULL_Genomes

```
ataaatcctcagctttaaaatcattttctttaagccaccaggaatattttcttcacataaagtaaatgg
atctctagtcattctactatataaaccatatgcattattaacacctttacaaaataaaaagctaatagta
cagtatcccttacaaaagttattaacagcactaactctatgtctaaaaggtgttaaaataaacacaagtg
cagtattataatagaatgtctacttgcaaaattacatttaaacttacttaaaagttttttatatagggt
ttctgccttttcttggtgtatgtattacaaatgcagttaagttctattactaaatacagcttgagac
acaaattcttccaattcttaggaaatgataaagatgcatctgtagcattgtcctttttttttaggtgg
tgttgcctgtgaacattgtggttcctcatcatcttctctagtacgctttgtaggggtttctccaggagat
ttaggcatttcctcattacatcttagttcttcttcccagtaggaattaaactgagaccaccagtaatccc
agtctggggtaccatatgtgggtatctataataaaaaaaagttattaatttacttataaaacataaaagt
acccctataataaaaacatgcttacctggttaagccaaccccttgcatggttgtaagaaatataatcttt
ttccagtaaaaaatgtttctgcactaatttcaaagccaaaccactctctatagcacctgtagcagtaac
actctatccacattggaggttttctaaatattttatattttgcttgtggcgcttgtctaaaagcagta
aaaacaattacacaaataataaaacccctttaagcatatgtcccagtcttttaaaatatactcttcaaaa
acatcaccataaacttctccaacaagcctgtactttctagggggaaagttacagcacaattctgtgcatt
ctacctgtgaagagctccacacttcatcttcttcttcatttagttggtgcactgtactaacacactcttg
cagttttaaatataaagaattaagtttttttcattttttcctcatttcccccctttgtcaggatgaaattct
ttgcatttgctaaggtattttgttctcattagtggtaaatttccccagcaggtcatatcaagacccagca
gctgcataagttcttttgcttcatttctggacaaagttttatccattttgccttcttttagcctcaaggcg
cctcagcaaggccctctgcttttagttcaaaaaggtgaggcttttag
```

>WU-Strain_S4
```
gcctcaggcctccttattataataaaaaaacctaagcatgattgacagtgtgggctaaaccaaaagcac
aagaacaaagctttagccaattagcagccacaaggtggagcaaaagtattaagtttcactgttatgtgc
aggaatgtgcagctgtgacctttaaagtttccgggcacggcgccaacttcctgggcctggtgccatacc
aacacagctgctgagcttccggaatacaatactggtgcccttgtaagtgtttttacaggtaagtaaggcc
tacaacagggcttatttgtactataagttaatgggggcccttgtagtccagcggaaagtgaagggtggc
```

TABLE 1-continued

```
ttaacagagacgtccttgggttcaaacctaagggtgccataagcaacattacattaatgttgtgacatct
ccagtcgggggtattggcctataggaaaccctagggctctataagcagcatacatatgttgtgacatctc
cgttgagtctgggggtattggtgctaccgtctcgaacctagccgacagccgttggatataaagggtcacc
atttttatttcagatgggcatattgcttgctgtgcctgaaatattgctgcatctgtagctggaggagca
gaggcactatccaattgctggatctggagctgcaatagcaactggtgaaggtttagctgctcttggtgggc
ttacagagtcagcagcactattaggggaaactgttgaaatatctgaagcagctgctactgtactaacaaa
agtacctgagcttgtaactgtaacacaaggtgtaacagcagctgtacaagggggtgcaggtcttgtaggt
ggtatatatacagctttagcagcagatcgccctggggacctgcctgcgagtaccccaacaggaagtccaa
gtggactacatcccccgcaggataatccccaaggaggtggacttaatatccagtccatccacaagcc
cctccacgcccctacccaggaatggcactggcacctatccctgaatacaacttggaaactggaattcca
ggggtcccggactgggtattcaacttcattgcatcccacctgcccgagttgcctagcctgcaggacgtgt
tcaatagaattgcctatggaatctggacatcatattacaatacggggagaacagtagttaatagagcagt
tagtgaagaattacaaagactactaggagatttagaatatggatttagaactgcacttgccaccattggg
gaatctgacccagtaaatgctatagttgaacaagtaagaagctttgttagtggaggaagacaaagagaac
tgttacaaatagctgcaggtcaacctgtagacatttctgaaggtgtatcaagaggcacagctactatttc
aaatgctgtagaagctgtaagagatgcaactcaaagactatcacaagcaacctacaactttgtttatgat
gcttctacccttccaagggatggctttaatgcacttagtgatggagttcacaggctaggccagtggattt
caatgcctgggctacaggggtactcccattatgcagccctgactggatttatatgtacttgaaga
gctaaacagtgacatttctaaaattcctacacagggaattaaaagaaactacaacaaaatggcctgcac
agcaaagccagcctgcacagcaaaaccaggaaggtcaccaagaagtcaacccacaagagtgcaaagcctt
ccaaaacaagtcagaaaaggaggggtagacgtgctggccgccgtaccactgtcagaagaaacagagttta
aagttgaattgtttgttaaacctgttattggaaatgcagaggggactaccccacattattggtctattag
```

WU_Full_Genomes

```
tagcccacttaaaactgctgaagctgctaatgttactcctgatgctgatactactgtgtgctacagcttg
tcacaggttgctcccctgatattcctaaccaggttagcgaatgtgacatgcttatatgggagctgtata
gaatggaaacgaagttttggtgcttcctgtgcttaatgctggcatacttactacagggggtgtaggagg
tattgctggtcctcaactttatttttgggcagttggaggacagcccttggatgtgctaggacttgctccc
actgaaaaatacaaggggcctgctcagtatactgtaaatcctaaaaccaatggtactgtgcctcatgttt
attccagttctgaaacacccagggcaaggtcactaatgaaaagtacagcatcgaatcatgggtggcaga
ccctagccgcaatgataactgcagatactttggcagaatggttggaggggctgcaactccaccagtggtg
tcatttagtaataatagcacaattccactgttggatgaaaatggcattggcattctttgcttgcaaggta
gattgtacataacttgtgctgacctttgggagttaacaaaaatagagtacatacagggcttttccagatt
ttttaggctacattttagacaaagaagggttagaaacccatatactataaatttgctttataagcaggtg
tttaataagccagctgatgacattagtgggcaactgcaggttacagaggttactatgactgaagaaacag
ggcccttgcctcccacagtagagggaaatgttggtgtacccacaaccagtaatttgtctcatttgcctgc
aactgtaactttacaagccacaggcccaatactaaacacacaaggaataatgtaataaatgcagtttatta
ataaagcaattttaagcattgtgttttttcaagtatgttgcatccatttgttacattcatttgcatgtcag
caaattcagtaaggcctatatatttgtctaacagttctttccaatacacaactttagcttgtatacatgg
gtgaaaatcactaacaggcctgcaccatattaacataagtaaaacacacattccactttgtaaaactctt
tttaccattagttctggagttttatccagactttcttttaagtgtcttttgggtgtaaaaagtacagttt
tatgaaatctaggagccaaagtagcagggactaaatattcattcattgttacaatacctggaggaaaaat
ttgtgaccttttatttaaatgtttttttttctaaattaactttaacacttccatctaaatagtctcttaaa
ttatctaagttactcattccatttccagatggtaacagtttattatctcctacttgacctttacatctt
caaatactactgtaaattgatctattgcaactcctaactcaaatttaatctatcagctggaatattaat
atttaaggccttttcctccacaaaggtcaagtaaagcagcagcaacagttgttttaccactgtttataggc
cccttaaaaacccaataccttttttttaggtacatttcaactataacttttaggtacctgtatacaagct
catctattttaccatttaggcctaaataccaggctacaccagccatatataataaaacatcttgctcacc
tttaatagtttttatccattttgtccagtatttttcaaatcttctagctaataaatcttctctgacata
tttaaactatctaccctttcttttgcaataaccacatcaatagcctgttgacacacatttttttgactt
tactgtctgaaaatagtaaagcatttttttgatgttccatatgaagtctattatgagttgcatcttcatt
actattgcatttttcacactcttctaccttaatagatagttgtaaatataatccaagtaataagtacaca
tcatcaattcctaattctaaagcaaattctgacaaagccttccaatttaattgatctttaaactccccat
ataaatcctcagctttaaaatcattttcttttaagccaccaggaatatttcttcacataaagtaaatgg
atctctagtcattctactatataaaccatatgcattattaacacccttacaaaataaaaagctaatagta
cagtatcccttacaaaagttattaacagcactaactctatgtctaaaaggtgttaaaataaaacacaagtg
cagtattataatagaatgtctacttgcaaaattacatttaaacttacttaaaagttttttatataggggt
ttctgcctttcttttggtggtatgtattacaaatgcagttaaagttctattactaaatacagcttgagac
acaaattcttccaattcttaggaaatgataaagatgcatctgtagcattgtcctttttttttttttaggtg
gtgttgcctgtgaacattgtggttcctcatcatcttctctagtacgctttgtaggggtttctccaggaga
tttaggcatttcctcattacatcttagttcttcttcccagtaggaattaaactgagaccaccagtaatcc
cagtctggggtaccatatgtgggtatctataataaaaaaagttattaatttacttataaaacataaaag
taccctataataaaaacatgcttacctggttaagccaaccccttgcatggttgtaagaaatataatctt
ttttccagtaaaaaaatgtttctgcactaatttcaaagccaaaccactctctatagcacctgtagcagtaa
cactctatccacattggaggttttctaaatattttatatttttgcttgtggcgcttgtctaaaaagcagt
aaaaacaattactacaaataataaaccccttttaagcatatgtcccagtctttttaaaatatactcttcaaa
aacatcaccataaacccctccaacaagcctgtacttcctaggggggaaagttacagcacaattctgtgcat
tctacccgcgaagagctccacacttcatcttcttcttcatttagttggtgcactgtactaacacactctt
gcagttttaaatataaagaattaagcttttttcatttttcctcatttccccctttgtcaggatgaaattc
tttgcatttgctaaggtattttgttctcattagtggtaaatttccccagcaggtcatatcaagacccagc
agctgcataagttctttttgcttcatttctggacaaagtttttatccattttgccttctttagcctcaaggc
gcctcagcaagggccctctgcttttagttcaaaaaggtgaggcttttag
```

WU_Full_Genomes

>WU-Strain_S5
```
gccccaggcctccttattataataaaaaaaagctaagcatgattgacagtgtgggctaaaccaaaagcac
aagaacaaagcttttagccaattagcagccacaaggtggagcaaaagtattaagtttcactgttatgtgc
aggaatgtgcagctgtgacctttttaaagtttccggggcacggcgccaacttcctgggcctggtgccatacc
```

TABLE 1-continued

```
aacacagctgctgagcttccggaatacaatactggtgcccctttgtaagtgttttacaggtaagtaaggcc
tacaacagggcttatttgtactataagttaatgggggccctttgtagtccagcggaaagtgaagggtggc
ttaacagagacgtccttgggttcaaacctaagggtgccataagcaacattacattaatgttgtgacatct
ccagtcgggggtattggcctataggaaaccctagggctctataagcagcatacatatgttgtgacatctc
cgttgagtctgggggtattggtgctaccgtctcgaacctagccgacagccgttggatataaagggtcacc
atttttatttcagatgggcatattgcttgctgtgcctgaaataattgctgcatctgtagctggaggagca
gaggcactatcaattgctggatctggagctgcaatagcaactggtgaaggtttagctgctcttggtgggc
ttacagagtcagcagcactattaggggaaactgttgaaatatctgaagcagctgctactgtactaacaaa
agtacctgagcttgtaactgtaacacaaggtgtaacagcagctgtacaaggggtgcaggtcttgtaggt
ggtatatatacagctttagcagcagatcgccctggggacctgcctgcgagtaccccaacaggaagtccaa
gtggactacatcccccgcaggatacaatccccaaggaggtggacttaatatccagtccatccacaagcc
cctccacgcccctacccaggaatggcactggcacctatccctgaatacaacttggaaactggaattcca
gggtcccggactgggtattcaacttcattgcatcccacctgcccgagttgcctagcctgcaggacgtgt
tcaatagaattgcctatggaatctggacatcatattacaatacggggagaacagtagttaatagagcagt
tagtgaagaattacaaagactactaggagatttagaatatggatttagaactgcacttgccaccattggg
gaatctgacccagtaaatgctatagttgaacaagtaagaagctttgttagtggaggaagacaaagagaac
tgttacaaatagctgcaggtcaacctgtagacattctgaaggtgtatcaagaggcacagctactattc
aaatgctgtagaagctgtaagacatgcaactcaaagactatcacaagcaacctacaactttgtttatgat
gcttctacccttccaagggatggctttaatgcacttagtgatggagttcacaggctaggccagtggattt
caatgcctgggctacaggggtactcccattatgcagccctgactggattttatatgtacttgaaga
gctaaacagtgacatttctaaaattcctacacagggaattaaaagaaaactacaacaaaatggcctgcac
agcaaagccagcctgcacagcaaaaccaggaaggtcaccaagaagtcaacccacaagagtgcaaagcctt
ccaaaacaagtcagaaaaggagggtagacgtgctggccgccgtaccactgtcagaagaaacagagttta
aagttgaattgtttgttaaacctgttattggaaatgcagaggggactacccacattattggtctattag
tagccacttaaaactgctgaagctgctaatgttactcctgatgctgatactactgtgtgctacagcttg
tcacaggttgctcccccctgatattcctaatcaggttagtgaatgtgacatgcttatatgggagctgtata
gaatggaaacagaagttttggtgcttcctgtgcttaatgctggcatacttactacaggggtgtaggagg
tattgctggtcctcaactttatttttgggcagttggaggacagccctggatgtgctaggacttgctccc
actgaaaaatacaaggggcctgctcagtatactgtaaatcctaaaaccaatggtactgtgcctcatgttt
attccagttctgaaacacccagggcaagggtcactaatgaaaagtacagcattgaatcatgggtggcaga
ccctagccgcaatgataactgcagatactttggcagaatggttggaggggctgcaactccaccagtggtg
tcatttagtaataatagcacaattccactgttggatgaaaatggcattggcattctttgcttgcaaggta
gattgtacataacttgtgctgaccttttgggagttaacaaaaatagagtacatacagggctttccagatt
ttttaggctacactttagacaaagaagggttagaaacccatatactattactactaaatttgctttataagcaggtg
tttaataagccagctgatgacattagtgggcaactgcaggttacagaggttactatgactgaagaaacag
ggcccttgcctcccacagtagagggaaatgttggtgtacccacaaccagtaatttgtctcatttgcctgc
aactgtaactttacaagccacaggcccaatactaaacacacaaggataatgtaataaatgcagtttatta
ataaagcaattttaagcattgtgttttcaagtatgttgcatccatttgttacattcatttgcatgtcag
caaattcagtaaggcctatatatttgtctaacagttcttttccaatacacaactttagcttgtatacatg
gtgaaaatcactaacaggcctgcaccatattaacataagtaaaatacacattccactttgtaaaactctt
tttaccattagttctggagttttatccagactttcttttaagtgtcttttgggtgtaaaaagtacagttt
tatgaaatctaggagccaaagtagcagggactaaatattcattcattgttacaatacctggaggaaaaat
ttgtgaccttttatttaaatgttttttctaaattaacttaacactttccatctaaatagtctcttaaa
```
WU_Full_Genomes

```
ttatctaagttactcattccatttccagatggtaacagtttattatctcctacttgacctttttacatctt
caaatactactgtaaattgatctattgcaactcctaactcaaagtttaatctatcagctggaatattaat
atttaaggcctttcctccacaaaggtcaagtaaagcagcagcaacagttgttttaccactgtttataggc
cccttaaaaatccaatacctttttttaggtacattttcaactataacttttaggtacctgtatacaagct
catctattttaccatttaggcctaaataccaggctacaccagcatatataataaaacatcttgctcacc
tttaatagtttttatccattttgtccagtattttttcaaatcttctagctaataaaccttctctggacata
tttaaactatctacccttcttttttgcaataaccacatcaatagcctgttgacacacattttttgactt
tactgtctgaaaatagtaaagcattttttttgatgttccatatgaagtctattatgagttgcatcttcatt
actattgcatttttcacactcttctaccttaatagatagttgtaaatataatccaagtaataagtacaca
tcatcaattcctaattctaaagcaaattctgacaaagccttccaatttaactgatctttaaactccccat
ataaatcctcagctttaaaatcattttcttttaagccaccaggaatattttcttcacataaagtaaatgg
atctctagtcattctactatataaaccatatgcattattaacacccttacaaaataaaaagctaatagta
cagtatcccttacaaaagttattaacagcactaactctatgtctaaaaggtgttaaaataaacacaagtg
cagtattataataagaatgtctcagtgtcaaaattacatttaaacttacttaaaagttttttataatagggt
ttctgccttttctttggtggtatgtattacaaatgcagttaaagttctattactaaatacagcttgagac
acaaattcttccaattcttttaggaaatgataaagatgcatctgtagcattgtccttttttttttttaggtg
gtgttgcctgtgaacattgtggttcctcatcatcttctctagtacgctttgtaggggtttctccaggaga
tttaggcattcctcattacatcttagttcttcttcccagtaggaattaaactgagaccaccagtaatcc
cagtctgggtaccatatgtgggtatctataataaaaaaaaagttattaatttacttataaaacataaaag
taccccctataataaaaacatgcttacctggttaagccaaccccttgcatggttgtaagaaatataatctt
tttccagtaaaaaaatgtttctgcactaatttcaaagccaaaccactctctatagcacctgtagcagtaa
cactctatccacattggaggttttctaaatattttatattttttgcttgtggcgcttgtctaaaaagcagt
aaaaacaattacacaaataataaaacccctttaagcatatgtcccagtcttttaaaatatactcttcaaa
aacatcaccataaacttctccaacaagcctgtactttctaggggaaagttacagcacaattctgtgcat
tctacctgtgaagagctccacacttcatcttcttcttcatttagttggtgcactgtactaacacactctt
gcagtttaaatataaagaattaagcttttttcattttttcctcatttcccccttttgtcaggatgaaattc
tttgcatttgctaaggtattttgttctcattagtggtaaatttccccagcaggtcatatcaagacccagc
agctgcataagttcttttgcttcatttctggacaaagttttatccattttgccttctttagcctcaaggc
gcctcagcaaggccctctgcttttagttcaaaaaggtgaggcttttttag
```

A "portion" or "fragment" of the disclosed nucleic acid molecules are those containing at least about 10, 15, 25, 30, 35, 40, 45, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,500, 2,000, 2,500, 3,000, 3,500, 4,000, 4,500, 5,000, or more contiguous nucleic acids in length of the relevant nucleic acid molecule. In one embodiment, the portion or fragment has at least one functional feature of the nucleic acid molecule. Such fragments or portions include those listed in Table 2 as SEQ ID NO: 7-57.

TABLE 2

WU_250bp_VP2Frag_all

```
>WU(1331-1580)
TGTTACAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGACTAGGCCAGTGGATTT
CAATGCCTGGGGCTACAGGGGGTACTCCCCATTATGCAGC

>WU_Strain_B16
TGTTaCAAATAGCTGCAGGTCAACCTGTAGACATTTCTGAAGGTGTATCAAGAGGCACAGCTACTATTTC
AAATGCTGTAGAAGCTGTAAgAGATGCAACTCAAAGACTATCACAAGCAACCTACAACTTTGTTTATGAT
GCTTCTACCcTTcCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_B12
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGACTAGGCCAGTGGATTT
CAATGCCTGGGGCTACAGGGGGTACTCCCCATTATGCAGC >WU_Strain_B3
TGTTaCAAATAGCTGCAGGTCAACCTGTAGACATTTCTCAAGGTGTATCAACAGGCAGAGCTACTATTTC
AAATGCTGTACAAGCTGTAAGAGATGCAACTGAAAGACTATCACAAGCAACCTACAACTTTGTTTATGAT
GCTTCTACCcTTCCAAGGGATGGCTTTAATGCACTTAGTGATGGAGTTCACAGACTAGGCCAGTGGATTT
CAATGCCTGGGGCTACAGGGGGTACTCCCCATTATGCAGC >WU_Strain_B4
TGTTaCAAATAgCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_B13
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_B20
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGACTAGGCCAGTGGATTT
CAATGCCTGGGGCTACAGGGGGTACTCCCCATTATGCAGC >WU_Strain_B14
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCcTTCCAAGGGATGGCTTTAATGCACTTAGTGATGGAGTTCACAGACTAGGCCAGTGGATTT
CAATGCCTGGGGCTACAGGGGGTACTCCCCATTATGCAGC >WU_Strain_B5
TGTTaCAAATaGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_B11
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
```

WU_250bp_VP2Frag_all

```

TABLE 2-continued

>WU_Strain_B26
TGTTaCAAATagCTGCAGGTCAACCTGTAGACATTTCTCAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGACTAGGCCAGTGGATTT
CAATGCCTGGGGCTACAGGGGGTACTCCCCATTATGCAGC >WU_Strain_B30
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTtCACAGGCTAGGCCAGTGGATTT
CAATGCCTGGGGCTACAGGGGGTACTCCCCATTATGCAGC >WU_Strain_B27
TGTTaCAAATaGCTGCAGGTCAACCTGTAGACATTTCTCAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGACTAGGCCAGTGGATTT
CAATGCCTGGGGCTACAGGGGGTACTCCCcATTATGCAGC >WU_Strain_B33
TGTTACAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_B32
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCcTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_B34
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGACTAGGCCAGTGGATTT
CAATGCCTGGGGCTACAGGGGGTACTCCCCATTATGCAGC >WU_Strain_B31
TGTTaCAAATAGCTGCAGGTCAACCTGTAGACATTTCTGAAGGTCTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_B23
WU_250bp_VP2Frag_all TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCcTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_B19
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_B29
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCCATTATGCAgC >WU_Strain_B36
TGTTaCAAATaGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_B6
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_B8
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCcATTATGCAGC TABLE 2-continued

```
>WU_Strain_B7
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGAcTATCACAAGCAACCTACAACTTTGTTTATGAT
GCTTcTACCcTTCCAAGGGATGGCTTTAATGCACTTAGTGATGGAGTTCACAGGCTAGGCCAGTGGATTt
CaatGCCTGGGGCTACAGGGGGTACTCCCCATTATGCAGC >WU_Strain_B18
TgtTacaAATAGCTGCAGGTCAACCTGTAGACATTTCTGAAGGTGTATCAAGAGGCACAGCTACTATTTC
AAATgCtGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_B17
TGTTACAAATAGCTGCAGGTCAACCTGTAGACATTTCTGAAGGTGTATCAAGAGGCACAGCTACTATTTC
AAATGCtGTAGAAGCTGTAAGAGATGCAACTCAAAGACTATCACAAGCAACCTaCAACTTTGTTTATGAT
GCTTCTACCcTTcCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_B1
TGTTACAAATAGCTGCAGGTCAACCTGTAGACATTTCTGAAGGTGTATCAAGAGGCACAGCTACTATTTC
AAATgCtGTAGAAGCTGTAAGAGATGCAACTCAAAGACTATCACAAGCAACCTACAACTTTGTTTATGAT
GCTTCTACCCTtCCAAGGGATGGCTTTAATGCACTTAGTGATGGAGTTCACAGGCTAGGCCAGTGGATTT
```

WU_250bp_VP2Frag_all

```
CAATGCCTGGGGCTACAGGGGGTACTCCCCATTATgcagc

>WU_Strain_B10
TGTTaCAAATACCTGCAGGTCAACCTGTACACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCcTTcCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_B21
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCcTTcCAAGGGATGGCTTTAATGCACTTAGTGATGGAGTTCACAGACTAGGCCAGTGGATTT
CAATGCCTGGGGCTACAGGGGGTACTCCCCATTATGCAGC >WU_Strain_B35
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTAcCcTTcCAAGGGATGGCTTTAATGCACTTAGTGATGGAGTtCACAGGCTAGGCCAGTGGATTT
CAaTGCCTGGGGCTACAGGGGGTACTCCCCATTATGCAGC >WU_Strain_B24
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCcTTCCAAGGGATGGCTTTAATGCACTTAGTGATGGAGTtCACAGGCTAGGCCAGTGGATTT
CAATGCCTGGGGCTACAGGGGGTACTCCCCATTATGCAgC >WU_Strain_B22
TGTTaCAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTtCACAGGCTAGGCCAGTGGATTT
CAATGCCTGGGGCTACAGGGGGTACTCCCCATTATGCAGC >WU_Strain_B37
TGTTaCAAATaGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
caaTGCCTGGGGCTACAGGGGGTACTCCCCATTATGCAGC >WU_Strain_B28
TGTTaCAAATaGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTtCACAGGCTAGGCCAGTGGATTT
CAATGCCTGGGGCTACAGGGGGTACTCCCCATTATGCAGC >WU_Strain_B2
TGTTaCAAATAGCTGCAGGTCAACCTGTAGATGTATCAAGAGGCACAGCTACTATTTCAAATGCTGTACA
AGCTGTAAGAGATGCAACTGAAAGACTATCACAAGCAACCTACAACTTTGTTTATGATGCTTCTACCCTT
CCAAGGGATGGCTTTAATGCACTTAGTGATGGAGTTCACAGACTAGGCCAGTGGATTTCAATGCCTGGGG
CTACAGGGGGTACTCCCCATTATGCAGC >WU_Strain_B9
TGTTACAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC
```

TABLE 2-continued

>WU_Strain_S1
TGTTACAAATAGCTGCAGGTCAACCTGTAGACATTTCTGAAGGTGTATCAAGAGGCACAGCTACTATTTC WU_250bp_VP2Frag_all

AAATGCTGTAGAAGCTGTAAGAGATGCAACTCAAAGACTATCACAACCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC

>WU_Strain_S2
TGTTACAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_S3
TGTTACAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGCTACAGGGGGTACTCCCCATTATGCAGC >WU_Strain_S4
TGTTACAAATAGCTGCAGGTCAACCTGTAGACATTTCTGAAGGTGTATCAAGAGGCACAGCTACTATTTC
AAATGCTGTAGAAGCTGTAAGAGATGCAACTCAAAGACTATCACAAGCAACCTACAACTTTGTTTATGAT
GCTTCTACCCTTCCAAGGGATGGCTTTAATGCACTTAGTGATGGAGTTCACAGGCTAGGCCAGTGGATTT
CAATGCCTGGGGCTACAGGGGGTACTCCCCATTATGCAGC >WU_Strain_S5
TGTTACAAATAGCTGCAGGTCAACCTGTAGACATTTCTGAAGGTGTATCAAGAGGCACAGCTACTATTTC
AAATGCTGTAGAAGCTGTAAGACATGCAACTCAAAGACTATCACAAGCAACCTACAACTTTGTTTATGAT
GCTTCTACCCTTCCAAGGGATGGCTTTAATGCACTTAGTGATGGAGTTCACAGACTAGCCCAGTGGATTT
CAATGCCTGGGGCTACAGGGGGTACTCCCCATTATGCAGC >WU_Strain_S6
tgttacaaatagctgcaggtcaacctgtagacatttctgaaggtgtatcaagaggcacagctactatttc
aaatgctgtagaagctgtaagagatgcaactcaaagactatcacaagcaacctacaactttgtttatgat
gcttctacccttccaagggatggctttaatgcacttagtgatggagttcacaggctaggccagtggattt
caatgcctggggctacagggggtactccccattatgcagc >WUVirus [protein - VP1]
MACTAKPACTAKPGRSPRSQPTRVQSLPKQVRKGGVDVLAAVPLSEETEFKVELFVKPVI
GNAEGTTFHYWSISSPLKTAEAANVTPDADTTVCYSLSQVAPPDIPNQVSECDMLIWELY
RNETEVLPVLNAGILTTGGVGGIAGPQLYFWAVGGQPLDVLGLAPTEKYKGPAQYTVN
PKTNGTVPHVYSSSETPRARVTNEKYSIESWVADPSRNDNCRYFGAMVGGAATPPVVSFS
NNSTIPLLDENGEGILCLQGRLYITCADLIGVNKNRVHTGLSRFFRLHFRQRRVRNPYTI
NLLYKQVTNKFADDISGQLQVTEVTMTEETGPLPPTVEGNVGVPTTSNSLSHLPATVTLQA
TGPLLNTQG >WUVirus [protein - VP2]
MGILLAVPEILAASVAGGAEALSIAGSGAAIATGEGLAALGGLTESAALLGETVEISEAA
ATVLTKVPELVTVTQGVTAAVQGGAGLVGGIYTALAADRFGDLPASTPTGSPSGEHPPAG
YNPQGGGLNIQSIHKPLHAPYPGMALAPIPEYNLETGIPGVPDWVFNFIASHLPELPSLQ
DVFNRIAYGIWTSYYNTGRTVVNRAVSEELQRLLGDLEYGFRTALATIGESDPVNAIVEQ
VRSFVSGGRERELLQIAAGQPVDISEGVSRGTATISNAVEAVRDATQRLSQATYNTVYDA
STLPRDGINALSDGVHRLGQWISMPGATGGTPHYAAPDWILYVLEELNSDISKIPTQGIK
RKLQQNGLHSKASLHSKTRKVTKKSTHKSAKPSKTSQKRRGRRAGRRTTVRRNRV >WUVirus [protein - VF3]
MALAPIPEYNLETGIPGVPDWVFNFIASHLPELPSLQDVFNRIAYGIWTSYYNTGRTVVN
RAVSEELQRLLGDLEYGFRTALATIGESDPVNAIVEQVRSFVSGGRERELLQIAAGQPVD
ISEGVSRGTATISNAVEAVRDATQRLSQATYNFVYDASTLPRDGENALSDGVHRLGQWIS
MPGATGGTPHYAAFDWILYVLEELNSDISKIPTQGIKAKLQQNGLHSKASLSKTRKVTK
KSTHKSAKPSKTSQKRRGRRAGRRTTVRRNRV >WUVirus [protein = Large T Antigen]
MDKTLSRNEAKELMQLLGLDMTCWGNLPLMRTKYLLSKCKEFHPDKGGNEEKNKKLNSLYLKLQECVSTVE
QLNEEEDEVWSSSQIPTYGTPDWDYWWSQFNSYWEEELRCNEEHPKSPGETPKRTREODEEPQCSQATP
PKKKKDNATDASLSFPKELEEFVSQAVFSNRTLTAFVIHTFKEKAETLYKKLLSKFKCNFASRHSYYNTA
LVFILTPFRHRVSAVNNFCKGYCTISFLFCKGVNNAYGLYSRMTRDPFTLCEENIPGGLKENDFKAEDLY
GEFKDQLNWKALSEFALELGIDDVYLLLGLYLQLSIKVEECEKCNSNEDATHNALHMEHQKNALLFSDSK
SQKNVCQQAIDVVIAKRRVDSLNHSREDLLARRFEKILDKNDKTIKGEQDVLLYMAGVAWYLGLNGKIGE
LVYRYLKVIVENVPKKRYWVFKGPINSGKTTVAAALLDLCGGKALNINIPADRLNFELGVAIDQFTVVFE
DVKGQVGDNKLLPSGNGNSNLDNLRDYLDGSVKVNLEKKHLNERSQIFPPIVTMNEYLVPATLAPRFHK
YVLFTPKRHLKESLDKTPELMVKRVLQSGMCILFMLIWCRPVSDFHPCIQAKVVTWKELLDKYIGLTEFA
DMQMNVTNGCNILREKHNA

TABLE 2-continued

```
>WUVirus [protein = Small T Antigen]
MDKTLSRNEAKELMQLLGLDMTCWGNLPLMRTKYLSKCKEFHPQMGGWEEKMKKINSLYL
KLQECVSTVHQLNEEEDEVWSSSQVECTELLCCNFPPRKYRLVGEVYGDVFEEYILKQWDI
CLKGFYYLCNCFYCFLDKAHKQKYKIFRKPPHWIECYCYRCYEWFGFEISAETFFYWKK
IIFLTTMQGUGLTR
```

Small T Antigen-Splicing

```
>Small T Antigen-Spliced
atggataaaactttgtccagaaatgaagcaaaagaacttatgcagctgctgggtcttgatatgacctgct
ggggaaatttaccactaatgagaacaaaataccttagcaaatgcaaagaatttcatcctgacaaaggggg
aaatgaggaaaaaatgaaaaagcttaattctttatatttaaaactgcaagactgttgtagtacagtgcac
caactaaatgaagaagaagatgaagtgtggagctcttcacaggtagaatgcagagaattgtgctgtaact
ttcccctagaaagtacaggcttgttggagaagtttatggtgatgttttgaagagtatattttaaaaga
ctgggacatatgcttaaagggttttattatttgtgtaattgttttactgcttttagacaagcgccac
aagcaaaaatataaaatatttagaaaacctccaatgtggatagagtgttactgctacaggtgctatagag
agtggtttggctttgaaattagtgcagaaacattttttttactggaaaaagattatatttcttacaactat
gcaaggggttggcttaaccagatacccacatatggtaccccagactgggattactggtggtctcagttta
attcctactgggaagaagaactaa >Small T Antigen-Spliced
MDKTLSRNEAKELNQLLGLDHTCKGNLPLMRTKYLSKCKEFEHPDKGGNEEKNKKLNSLYLKLQECVSTVH
QLNEEEDEVWSSSQVECTELCCNFPPRKYRLVGEVYGDVFEEYILKDWDICLKGFYYLCNCFYCFLDKRH
KQKYKIFRKPPMKIECYCYRCYREWFGFEI
SAETFFYWKKIIFLTTMQGVGLTRYPHWPQTGITGGLSLIPPGKKN
```

A complement of the disclosed nucleic acid sequence can be the exact complement or one that hybridizes to the disclosed nucleic acid sequence under stringent conditions. The term "under stringent condition" refers to hybridization and washing conditions under which nucleotide sequences having at least 70%, at least 75%, at least 80%, at least 85%, at least 90%, or at least 95% identity to each other remain hybridized to each other. In one example, stringent hybridization conditions are hybridization in 6× sodium chloride/sodium citrate (SSC), 0.5% SDS at about 68° C. followed by one or more washes (e.g., about 5 to 30 min each) in 2×SSC, 0.5% SDS at room temperature. In another example, stringent hybridization conditions are hybridization in 6×SSC at about 45° C. followed by one or more washes (e.g., about 5 to 30 min each) in 0.1×SSC, 0.1% SDS at about 45-65° C.

Further provided herein are isolated, recombinant and/or chimeric variants of the human polyomavirus, a complement, or a portion thereof. Such variants include those that hybridize to one of the WU viral sequences or a portion thereof under moderate or high stringency conditions. Such variants include those with nucleotide substitutions, insertions and deletions and, in some embodiments, can account for about 5% of the viral genome sequence, about 2% of the viral genome, or less. A recombinant virus is one derived from a natural variant of WU virus. A natural variant of WU virus has a sequence that is different from the genomic sequence of WU virus as provided herein, due to one or more naturally occurred mutations, including, but not limited to, point mutations, rearrangements, insertions, deletions, and the like, to the genomic sequence that may or may not result in a phenotypic change. A chimeric WU virus is a recombinant WU virus which further comprises a heterologous nucleotide sequence. For example, a chimeric virus may be encoded by a nucleotide sequence in which heterologous nucleotide sequences have been added to the genome or in which endogenous or native nucleotide sequences have been replaced with heterologous nucleotide sequences.

Further provided herein is a viral vector that is derived from the genome of the WU virus or contains one or more portions of the WU genome. In one embodiment, the vector is one that contains a nucleic acid sequence that encodes at least a part of one viral protein or regulatory region(s) of the WU virus. In a specific embodiment, the vector comprises the WU virus replication origin shown in FIG. 5 (SEQ ID NO:113).

Provided herein is a host cell comprising a nucleic acid or a vector derived from or containing portions of the WU virus. Plasmid or viral vectors containing the polymerase components of WU virus may be generated in prokaryotic cells for the expression of the components in relevant cell types (bacteria, insect cells, eukaryotic cells). Plasmid or viral vectors containing full-length or partial copies of the WU viral genome will be generated in prokaryotic cells for the expression of viral nucleic acids in vitro or in vivo. The latter vectors may contain other viral sequences for the generation of chimeric viruses or chimeric virus proteins, may lack parts of the viral genome for the generation of replication defective virus, and may contain mutations, deletions or insertions for the generation of attenuated viruses. In addition, eukaryotic cells, transiently or stably expressing one or more full-length or partial WU viral proteins can be used. Such cells can be made by transfection (proteins or nucleic acid vectors), infection (viral vectors) or transduction (viral vectors) and may be useful for complementation of mentioned wild type, attenuated, replication-defective or chimeric viruses.

In another aspect, provided herein are primers and probes useful for the amplification and detection of the human polyomavirus WU and its variants. The isolated nucleic acids of WU Virus (SEQ ID NO:1), WU-Strain_S1 (SEQ ID NO:2), WU-Strain_S2 (SEQ ID NO:3), WU-Strain_S3 (SEQ ID NO:4), WU-Strain_S4 (SEQ ID NO:5), or WU-Strain_S5 (SEQ ID NO:6), sequences substantially identical thereto, complementary sequences, or a portion comprising at least 10, 15, 20, 25, 30, 35, 40, 50, 75, 100, 150, 200, 300, 400, or 500 consecutive bases of one of the foregoing sequences, may also be used as probes or primers to determine whether a biological sample, such as respiratory secretions, contain a virus having encoded a nucleic acid sequence disclosed herein or a variant thereof. In one embodiment, the primer or probe comprises an oligonucleotide comprising at least about 10 to 50 consecutive bases of the sequence. Exemplary amplification primers include, but are not limited to AG0044, AG0045, AG0048, AG0049, and those disclosed in Table 5.

The nucleic acid provided herein can be isolated or recovered from a biological sample by providing an amplification primer sequence pair for amplifying a nucleic acid encoding a WU virus, wherein the primer pair is capable of amplifying the nucleotide sequence of WU Virus (SEQ ID NO:1), WU-Strain_S1 (SEQ ID NO:2), WU-Strain_S2 (SEQ ID NO:3), WU-Strain_S3 (SEQ ID NO:4), WU-Strain_S4 (SEQ ID NO:5), or WU-Strain_S5 (SEQ ID NO:6), a complement, or a subsequence thereof; isolating the nucleic acid from the biological sample or treating the biological sample such that nucleic acid in the sample is accessible for hybridization to the amplification primer pair; combining the isolated or treated nucleic acid with the amplification primer pair; and amplifying nucleic acid, thereby isolating or recovering a nucleic acid encoding a WU virus from a biological sample. The WU virus also can be isolated or recovered from a biological sample by providing a polynucleotide probe comprising a sequence of the WU virus provided herein, or a subsequence thereof; isolating the nucleic acid from the biological sample or treating the biological sample such that nucleic acid in the sample is accessible for hybridization to a polynucleotide probe; combining the isolated nucleic acid or the treated biological sample with the polynucleotide probe; and isolating a nucleic acid that specifically hybridizes with the polynucleotide probe, thereby isolating or recovering a nucleic acid encoding a WU virus from a biological sample. A biological sample includes, but is not limited to cells, saliva, sputum, nasopharyngeal aspirates, urine, blood, feces, spinal fluid, tissue biopsy, and the like.

Amplification reactions are useful to quantify the amount of nucleic acid in a sample (such as the amount of message in a respiratory secretion sample), label the nucleic acid (e.g., to apply it to an array or a blot), or detect the nucleic acid. The skilled artisan can select and design suitable oligonucleotide amplification primers. Amplification methods are also well known in the art, and include, e.g., polymerase chain reaction (PCR); ligase chain reaction (LCR); transcription amplification; self-sustained sequence replication; Q Beta replicase amplification; automated Q-beta replicase amplification assay; and other RNA polymerase mediated techniques.

In another aspect, provided herein are isolated polypeptides or proteins that are encoded by a nucleic acid molecule comprising, consisting essentially or consisting of WU Virus (SEQ ID NO:1), WU-Strain_S1 (SEQ ID NO:2), WU-Strain_S2 (SEQ ID NO:3), WU-Strain_S3 (SEQ ID NO:4), WU-Strain_S4 (SEQ ID NO:5), or WU-Strain_S5 (SEQ ID NO:6), or a portion thereof. Such proteins include small T antigen (STAg), large T antigen (LTAg), VP1, VP2, and VP3. Further provided herein is a polypeptide sequence encoding the VP1 (SEQ ID NO:51), VP2 (SEQ ID NO:52), VP3 (SEQ ID NO:53), large T antigen (SEQ ID NO:54), small T antigen (SEQ ID NO:55), or spliced small T antigen (SEQ ID NO:57) of the WU virus as shown in Table 2. Also provided is a nucleotide sequence encoding spliced small T antigen (SEQ ID NO: 56).

Antibodies that specifically bind a polypeptide of the WU virus encoded by the nucleotide sequence of WU Virus (SEQ ID NO:1), WU-Strain_S1 (SEQ ID NO:2), WU-Strain_S2 (SEQ ID NO:3), WU-Strain_S3 (SEQ ID NO:4), WU-Strain_S4 (SEQ ID NO:5), or WU-Strain_S5 (SEQ ID NO:6), or a portion thereof, also are provided. These antibodies include antibodies that specifically bind a polypeptide sequence encoding the VP1 (SEQ ID NO:51), VP2 (SEQ ID NO:52), VP3 (SEQ ID NO:53), large T antigen (SEQ ID NO:54), small T antigen (SEQ ID NO:55), or spliced small T antigen (SEQ ID NO:57) of the WU virus as shown in Table 2. An antibody or an antibody fragment is specific for a polypeptide of the WU virus if it permits one of skill in the art to discern the presence of the virus in a sample. Thus, it is not cross-reactive with non-WU viral antigens. The antibodies include those that specifically bind cells or tissues that are infected by WU virus and/or the virus itself. Such antibodies include, but are not limited to polyclonal, monoclonal, bi-specific, multi-specific, human, humanized, chimeric, single chain antibodies, diabodies, nanobodies, single domain antibodies (e.g., camel antibodies), Fab, F(ab')$_2$, Fvs, intrabodies and fragments containing either a $V_L$ or $V_H$ domain or even a complementary determining region (CDR) that specifically binds to a polypeptide of the WU virus disclosed herein. Any suitable means can be employed to generate antibodies binding to the WU virus, a portion or protein thereof.

Antibodies useful in the detection of WU virus can be labeled with any suitable detectable label and employed in assays such as enzyme linked immunosorbent assays (ELISAs), Western blots, immunoprecipitations and immunofluorescence. In one embodiment, provided herein is a method of detecting in a biological sample an antibody that immunospecifically binds to the WU virus, or any proteins or polypeptides thereof. In another embodiment, the presence of the virus is detected in a biological sample using an antibody that immunospecifically binds to the WU virus-infected cells. In yet another embodiment, provided herein is a method of screening for an antibody that immunospecifically binds and neutralizes WU virus. Such an antibody is useful for a passive immunization or immunotherapy of a subject infected with WU virus.

Furthermore, provided herein are pharmaceutical compositions comprising the virus or portions thereof and a pharmaceutically acceptable carrier. Thus, some compositions can comprises one or more isolated proteins from the WU virus, live WU virus, attenuated WU virus, or inactivated WU virus. Pharmaceutical compositions can include recombinant and chimeric forms of the WU virus, or one or more protein subunits of the virus provided herein. Kits comprising pharmaceutical compositions also are provided.

Methods for detecting the presence, activity or expression of the WU virus in a biological sample include the detection of viral nucleic acid, viral particles, or viral protein production. The increased or decreased activity or expression of the WU virus in a sample relative to a control sample can be determined by contacting the biological sample with an agent which can detect directly or indirectly the presence, activity or expression of the WU virus. In a specific embodiment, the detecting agents are the antibodies or nucleic acid molecules of the present invention.

An exemplary method for detecting the presence or absence of a polypeptide or nucleic acid from the WU in a biological sample involves obtaining a biological sample from a patient and contacting the sample with a compound or an agent capable of detecting an epitope on a protein or nucleic acid (e.g., mRNA, genomic DNA) of the WU virus such that the presence of WU virus is detected in the sample. When detecting WU viral mRNA or genomic DNA, a labeled nucleic acid probe capable of hybridizing to mRNA or genomic DNA encoding a polypeptide may be employed. Such assays include northern hybridizations, southern hybridizations, in situ hybridizations, RT-PCR, and RNase protection. Detecting WU virus also may be accomplished using an antibody that specifically binds a WU viral polypeptide as disclosed herein. Typically, a test sample is obtained from a subject with a respiratory infection, the sample is contacted with a compound or agent capable of detecting WU virus, e.g., a polypeptide or mRNA or genomic DNA encoding a polypeptide, such that the presence of WU virus or the polypeptide or mRNA or genomic DNA encoding the polypeptide is detected in the sample if it is present, and comparing the presence of WU virus or the polypeptide or mRNA or genomic DNA encoding the polypeptide in the test sample to a control sample (e.g., from a healthy patient) lacking the WU virus, or the polypeptide or mRNA or genomic DNA encoding the polypeptide.

Further provided herein are methods provides a method for detecting an antibody, which immunospecifically binds to the WU virus, in a biological sample, for example blood, serum, saliva, respiratory secretions, urine, and the like from a patient likely to be suffering from WU viral infection. In one embodiment, the method comprising contacting the sample with the polypeptides or protein encoded by the nucleotide sequence of WU Virus (SEQ ID NO:1), WU-Strain_S1 (SEQ ID NO:2), WU-Strain_S2 (SEQ ID NO:3), WU-Strain_S3 (SEQ ID NO:4), WU-Strain_S4 (SEQ ID NO:5), or WU-Strain_S5 (SEQ ID NO:6), or a portion thereof, directly immobilized on a substrate and detecting the virus-bound antibody directly or indirectly by a labeled heterologous anti-isotype antibody. In another specific embodiment, the sample is contacted with a host cell comprising a nucleic acid molecule having the sequence of WU Virus (SEQ ID NO:1), WU-Strain_S1 (SEQ ID NO:2), WU-Strain_S2 (SEQ ID NO:3), WU-Strain_S3 (SEQ ID NO:4), WU-Strain_S4 (SEQ ID NO:5), or WU-Strain_S5 (SEQ ID NO:6), or a portion thereof., and expressing the polypeptides encoded thereby, and the bound antibody can be detected by immunofluorescent assay.

Kits for detecting the presence of WU virus or a polypeptide, antibody or nucleic acid provided herein in a test sample. The kit, for example, can comprise a labeled compound or agent capable of detecting WU virus or the polypeptide or a nucleic acid molecule encoding the polypeptide in a test sample and, in certain embodiments, a means for determining the amount of the polypeptide or mRNA in the sample (e.g., an antibody which binds the polypeptide or an oligonucleotide probe which binds to DNA or mRNA encoding the polypeptide). Kits can also include instructions for use.

For antibody-based kits, the kit can comprise, for example: (1) a first antibody (e.g., attached to a solid support) which binds to a polypeptide or epitope of the WU virus; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or to a sequence within the WU viral genome or (2) a pair of primers useful for amplifying a nucleic acid molecule containing an WU viral sequence. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for use.

In yet another aspect, provided herein is a method of diagnosing a polyomavirus infection in a patient comprising the step of testing for the presence or absence of human polyomavirus WU in a sample from a patient to be tested for polyomavirus infection. In some embodiments, the patient tested is one suffering from a respiratory infection. The virus to be detected can be any suitable method. The method of detecting the virus can optionally involve nucleic acid hybridization methods which are selective and specific for the viruses described herein. WU virus-specific primers or probes can also be employed as PCR primers, Reverse Transcriptase primers, probes for Southern or Northern analysis or other nucleic acid hybridization analysis for the detection of WU viral nucleic acids. The detection methods can also involve conventional immunoassays detecting one or more WU proteins such as Western Blots, enzyme linked immunoassays (ELISA) and radioimmunoassays (RIA). Preferred samples include respiratory secretions. The diagnosis for infections mediated by WU virus can include conventional criteria or diagnostic factors in combination with the use of the nucleic acids and related reagents disclosed herein. In some embodiments, the infection likely to be mediated by the WU virus is a respiratory infection. The impact of treatment upon the disease progression can be assessed using these methods at different times.

In yet another aspect, provided herein is a method of screening for anti-viral agents useful in reducing the symptoms of respiratory infections comprising: contacting a cell infected with the human polyomavirus WU with an anti-viral agent; assaying the anti-viral agent activity by determining the effect of the agent upon viral titer in the cell, and identifying the agent as an anti-viral agent if it inhibits viral replication, expression, or activity. The methods can be designed to screen for agents in in vitro assays against cell lines infected with the virus, against cells producing an enzyme from a virus or against a purified viral enzyme. Alternatively, the agents may be screened in in vivo assays where the virus is hosted by a mammal.

In one aspect, the anti-viral agent can prevent or inhibit the binding of the virus or viral proteins to a host cell under a physiological condition, thereby preventing or inhibiting the infection of the host cell by the virus. In another aspect, the anti-viral agent can be one that prevents or inhibits replication of the viral nucleic acid molecules in the host cell under a physiological condition by interacting with the viral nucleic acid molecules or its transcription mechanisms.

A variety of different test inhibitory molecules may be identified using the method as provided herein. Test viral inhibitory molecules can encompass numerous chemical classes. In certain embodiments, they are organic molecules, preferably small organic compounds having a molecular weight of more than 50 and less than about 2,500 daltons. Test viral inhibitory molecules can comprise functional groups necessary for structural interaction with proteins, particularly hydrogen bonding, and may include at least an amine, carbonyl, hydroxyl or carboxyl group, preferably at least two of the functional chemical groups. The test cell viral inhibitory molecules can comprise cyclical carbon or heterocyclic structures and/or aromatic or polyaromatic structures substituted with one or more of the above functional groups. Test viral inhibitory molecules are also include biomolecules like peptides, saccharides, fatty acids, steroids, purines, pyrimidines, derivatives, structural analogs or combinations thereof. Test viral inhibitory molecules of interest also can include peptide and protein agents, such as antibodies or binding fragments or mimetics thereof, e.g., Fv, F(ab')$_2$ and Fab.

Test viral inhibitory molecules also can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The following examples are offered to illustrate but not to limit the invention.

EXAMPLE 1

Identification and Characterization of WU Virus

Provided herein is the identification of a novel human polyomavirus present in respiratory secretions from patients with acute respiratory tract symptoms. The virus was initially detected in a nasopharyngeal aspirate from a three year old child from Australia diagnosed with pneumonia. A random library was generated from nucleic acids extracted from the nasopharyngeal aspirate and analyzed by high throughput DNA sequencing. Multiple DNA fragments were cloned that possessed limited homology to known polyomaviruses. We subsequently sequenced the entire virus genome of 5229 bp, henceforth referred to as WU virus, and found it to have genomic features characteristic of the family Polyomaviridae. The genome was predicted to encode small T Antigen, large T Antigen, and three capsid proteins: VP1, VP2 and VP3. Phylogenetic analysis clearly revealed that the WU virus was highly divergent from all known polyomaviruses. Screening of 2135 patients with acute respiratory tract infections in Brisbane, Australia and St. Louis, United States using WU virus specific PCR primers resulted in the detection of 43 additional specimens that contained WU virus. The presence of multiple instances of the virus in two continents suggests that this virus is widespread in the human population and raises the possibility that the WU virus may be a human pathogen.

Shotgun sequencing of respiratory secretion. A nasopharyngeal aspirate (NPA) from a three year old patient admitted to the pediatric ward of the Royal Children's Hospital in Brisbane, Australia with pneumonia was collected in October 2003. Testing of nucleic acid extracted from the NPA using a panel of 17 PCR assays for known respiratory viruses as described [19] yielded negative results. Total nucleic acid from the NPA was randomly amplified and cloned as described previously [8]. One 384 well plate of clones was sequenced using a universal M13 primer and the resulting sequence reads were analyzed using BLASTx [20]. Six reads, which collapsed into three unique regions, were identified with limited homology to known polyomavirus proteins (sequences available in FIG. 4). The highest scoring BLASTx hits for each of these three contigs possessed 35%, 50% and 34% amino acid identity to JC virus small T antigen, BK virus large T antigen, and SV40 VP1, respectively. Subsequent analysis revealed amino acid identities of 66%, 65% and 69% to KI virus for the three contigs. Furthermore, 3 of the 8 previously unclassified sequence reads were determined to have between 58-84% amino acid identity to KI virus VP1 and VP2 proteins by BLASTx analysis. Based on the limited sequence homology to known viruses, we tentatively assigned the name WU to the unknown polyomavirus.

Complete genome sequencing and genome analysis. The complete genome of WU was sequenced to 3× coverage using cloned fragments of the viral genome generated by a series of PCR primers. Analysis of the DNA sequence revealed genomic features characteristic of polyomaviruses. First the WU genome size of 5229 bp was quite comparable to those of the other primate polyomaviruses BK (5153 bp), JC (5130 bp) and SV40 (5243 bp). In addition, the overall GC content of the WU genome was 39%, which is quite similar to the GC content of BK (39%), JC (40%) and SV40 (40%). The genome organization included an early region coding on one strand for small T antigen (STAg) and large T antigen (LTAg), and a late region coding on the opposite strand for the capsid proteins VP1, VP2 and VP3 (FIG. 1). These two regions were separated by a regulatory region that contained typical polyomavirus features. The regulatory region contained an AT rich region on the late side of the putative replication origin. Three repeats of the consensus pentanucleotide LTAg binding site GAGGC were present as was one copy of a non-consensus LTAg binding site TAGGC. While most polyomaviruses contain four copies of the consensus, baboon polyomavirus (simian agent 12) is a primate polyomavirus that contains only three copies of the canonical binding sequence and one non-consensus binding site [21]. Unusual features in the WU regulatory region included the presence of two partially overlapping TAg binding sites and slightly variant spacing between the TAg binding sites as compared to SV40, BK and JC (FIG. 5).

In the early region, an unspliced open reading frame of 194 amino acids was detected that possibly encodes for the STAg. As the paradigm in other polyomaviruses is that STAg is expressed from a spliced message, analysis of potential splice sites revealed the presence of a putative splice donor sequence just one nucleotide 5' of the initially predicted stop codon. Splicing to a downstream putative splice acceptor site would excise an intron of 70 nucleotides and generate a slightly larger STAg of 217 amino acids (FIG. 6). While the precise carboxyl terminus of the WU STAg has not yet been experimentally verified, sequence analysis revealed the presence of a highly conserved cysteine rich motif $CX_5CX_{7-8}CXCX_2CX_{21-22}CSCX_2CX_3WF$ (SEQ ID NO:148) that was present in both of the predicted isoforms of WU STAg. This motif which is present in all STAgs was perfectly conserved in WU virus with the exception of the initial cysteine residue.

In all polyomaviruses, the initial ~80 amino acids of the N-terminus of the STAg and Large T antigen (LTAg) are identical; the LTAg is generated by alternative splicing of the early mRNA transcript. In WU virus, a conserved splice donor site was identified immediately after amino acid 84 of the early open reading frame. The position of the splice site is similar to that found in SV40, BK and JC virus, which occur after amino acids 82, 81 and 81, respectively. Splicing to a conserved splice acceptor site would generate a predicted protein of 648 amino acids (Table 3). The predicted WU virus LTAg contained conserved features common to T-antigens including: a DnaJ domain in the N terminus with the highly conserved hexapeptide motif HPDKGG (SEQ ID NO:149); the LxCxE motif necessary for binding Rb; a canonical DNA binding domain; a zinc finger region; and conserved motifs GPXXXGKT (SEQ ID NO:150) and GXXXVNLE (SEQ ID NO:151) in the ATPase-p53 binding domain [22].

TABLE 3

Homology of predicted WU proteins.

| Gene | Predicted Size (aa) | % Amino acid identity[a] to: | | | | |
|------|---------------------|------|------|------|------|--------|
| | | KI | JC | BK | SV40 | MuPy[c] |
| Small T | 194[b] | 68 | 40 | 41 | 38 | 23 |
| Large T | 648 | 70 | 48 | 49 | 49 | 32 |
| VP1 | 369 | 65 | 27 | 28 | 28 | 25 |
| VP2 | 415 | 71 | 16 | 17 | 17 | 12 |
| VP3 | 272 | 64 | 15 | 15 | 16 | 11 |

[a]Calculated using BioEdit
[b]The unspliced form was used to calculate % identity
[c]MuPY, Murine polyomavirus Based on comparative sequence analysis of LTAgs, the polyomaviruses are classified into two subclasses: a primate-like group exemplified by SV40 and a mouse polyoma-like group exemplified by murine polyoma virus [22]. Using these criteria, the T antigen of WU appeared to more closely resemble the mouse-polyoma like class of virus than the primate class. First, the mouse polyoma like viruses have insertions of varying length after amino acids 66 and 113 of SV40 as compared to the primate class. In the amino terminal domain of the WU virus LTAg, multiple sequence alignment revealed the presence of a two amino acid and a 10 amino acid insertion at these two loci, respectively. Furthermore, the primate-like class typically contains an extension of the carboxyl terminus termed the host range domain that is absent in the mouse polyoma-like class. By contrast to SV40, BK, JC and baboon polyomavirus, WU virus did not appear to encode a carboxyl terminal extension.

The sequence of the WU virus was aligned with 12 other reference large T antigen sequences. These are SEQ ID NO's: 134-147. This comparison reveals the presence of carboxy terminus extensions in the baboon polyoma BK, JC, and SV40, whereas WU virus does not appear to encode such a region.

In addition to LTAg and STAg, murine and hamster polyomaviruses utilize alternative splicing to generate an intermediate sized protein referred to as middle T antigen. The WU virus early region was scanned for splicing motifs similar to known murine and hamster polyomavirus splice donor and acceptor sequences, but no obvious combination of splice sites was detected that would yield a middle T Antigen sequence in the size range of known middle T antigens. In addition, SV40, JC, BK and baboon polyomavirus all encode a fourth late protein termed the agnoprotein. There was no open reading frame present in WU with any detectable homology to the known agnoproteins. Thus our sequence analysis suggests that neither middle T antigen nor agnoprotein are encoded by WU virus although it is possible that the sequences have diverged beyond our ability to recognize the appropriate splice sites or protein products.

Figure 2:
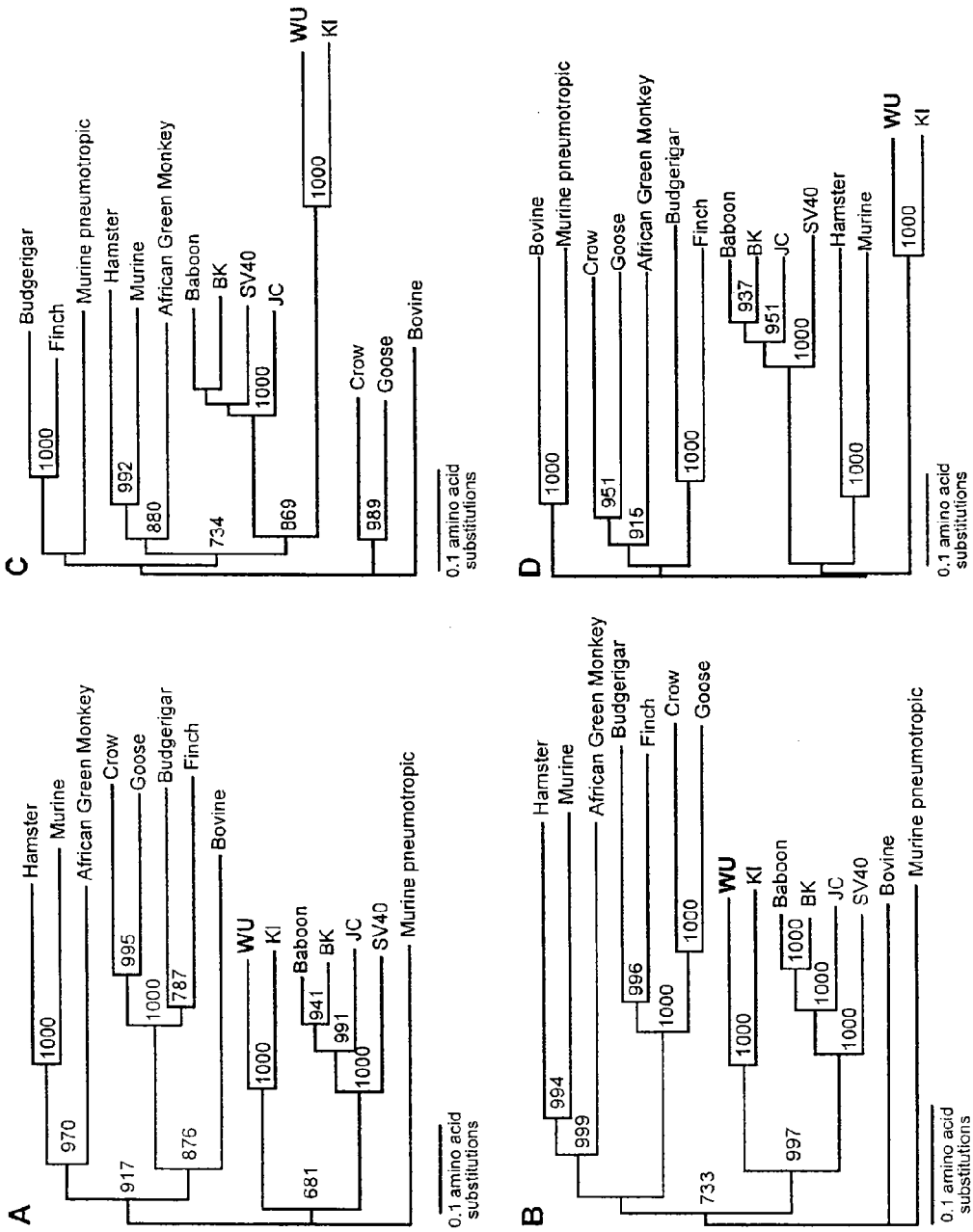

Phylogenetic Analysis. Multiple sequence alignments of the predicted STAg, LTAg, VP1 and VP2 open reading frames revealed that WU virus was clearly a novel virus that is most closely related to KI virus (FIG. 2). Neighbor joining analysis suggested that these two viruses appear to form a new subclass of polyomaviruses. In the early region and VP1 protein, the WU/KI branch was most closely related to the known primate polyomaviruses BK, SV40, JC and baboon polyomavirus (FIG. 2A-C). Finally, the VP2 open reading frame was so divergent that its evolutionary relationship to other polyomaviruses aside from KI could not be reliably established (FIG. 2D). Analysis of the VP3 amino acid sequence, which is completely contained within VP2, gave similar results as VP2.

Prevalence of WU. PCR primers were designed to amplify specifically WU. The initial screen used primers targeting the VP2 region, which possessed less than 20% amino acid homology to JC and BK virus to minimize the possibility of cross reactivity with the known primate polyomaviruses. Empirical testing of the primers on samples known to contain the human polyomaviruses BK and JC confirmed that the primers did not cross react with either of these genomes. Positives in the initial screen for WU virus were sequenced and then further confirmed by a second PCR reaction using primers targeting the 3' end of the WU virus LTAg coding sequence. All 43 positive samples in the initial screen were confirmed using the second pair of PCR primers. A subset of samples that tested negative in the initial screen was also tested with the second PCR primer pair, and none of those samples were positive.

Brisbane, Australia cohort. In order to assess the prevalence of WU polyomavirus, a cohort of 1245 respiratory specimens collected in 2003 in Brisbane was examined. Thirty-seven out of the 1245 (3.0%) samples tested were positive for the virus (Table 4). In this cohort, patients that tested positive ranged in age from 4 months to 53 years. The vast majority of the patients (33/37) were age 3 and under. In 12 patients with clear clinical evidence of respiratory tract infection, WU was the sole virus detected. Strikingly, in 25 of the 37 positive samples, one or more additional respiratory viruses was also detected. The most common coinfections were with rhinovirus (14 cases) and the newly described human bocavirus (10 cases). Furthermore, in one sample, a total of four viruses including WU, bocavirus, rhinovirus and adenovirus were detected, and in 6 other samples, a total of three viruses were detected (Table 4).

St. Louis, United States cohorts. In addition, we examined two cohorts of patients from St. Louis, United States. In one set of upper respiratory specimens collected in 2006, 5 out of 410 were positive for WU virus in the PCR assay. In addition, 480 bronchoalveolar lavage samples from patients (mostly adults) with severe acute respiratory illness were tested yielding one positive. Of the positive samples, all six were co-infected with other viruses (Table 4). The age range of the positive cases varied from 4 months to 51 years.

Figure 3:
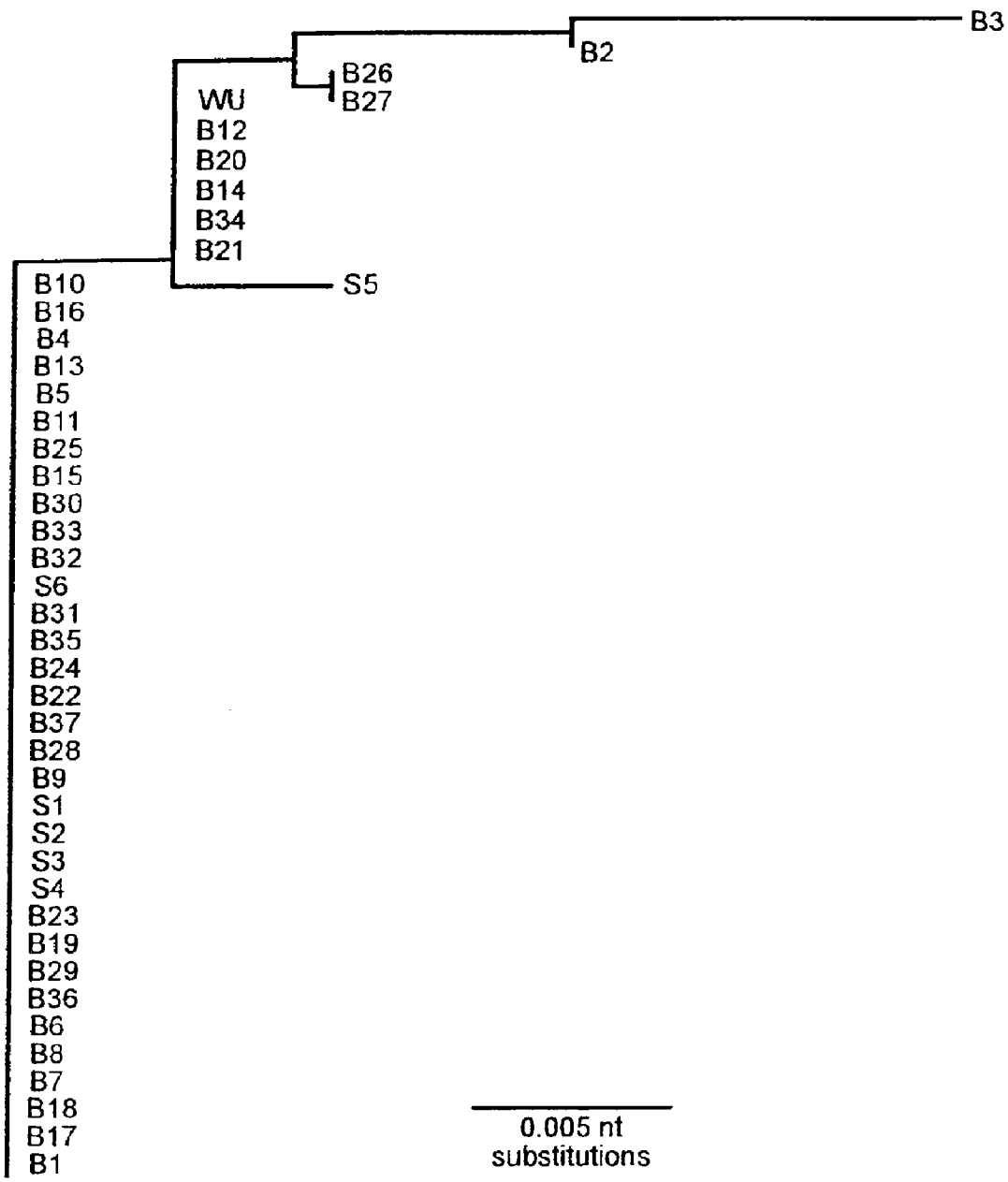
Figure 7:
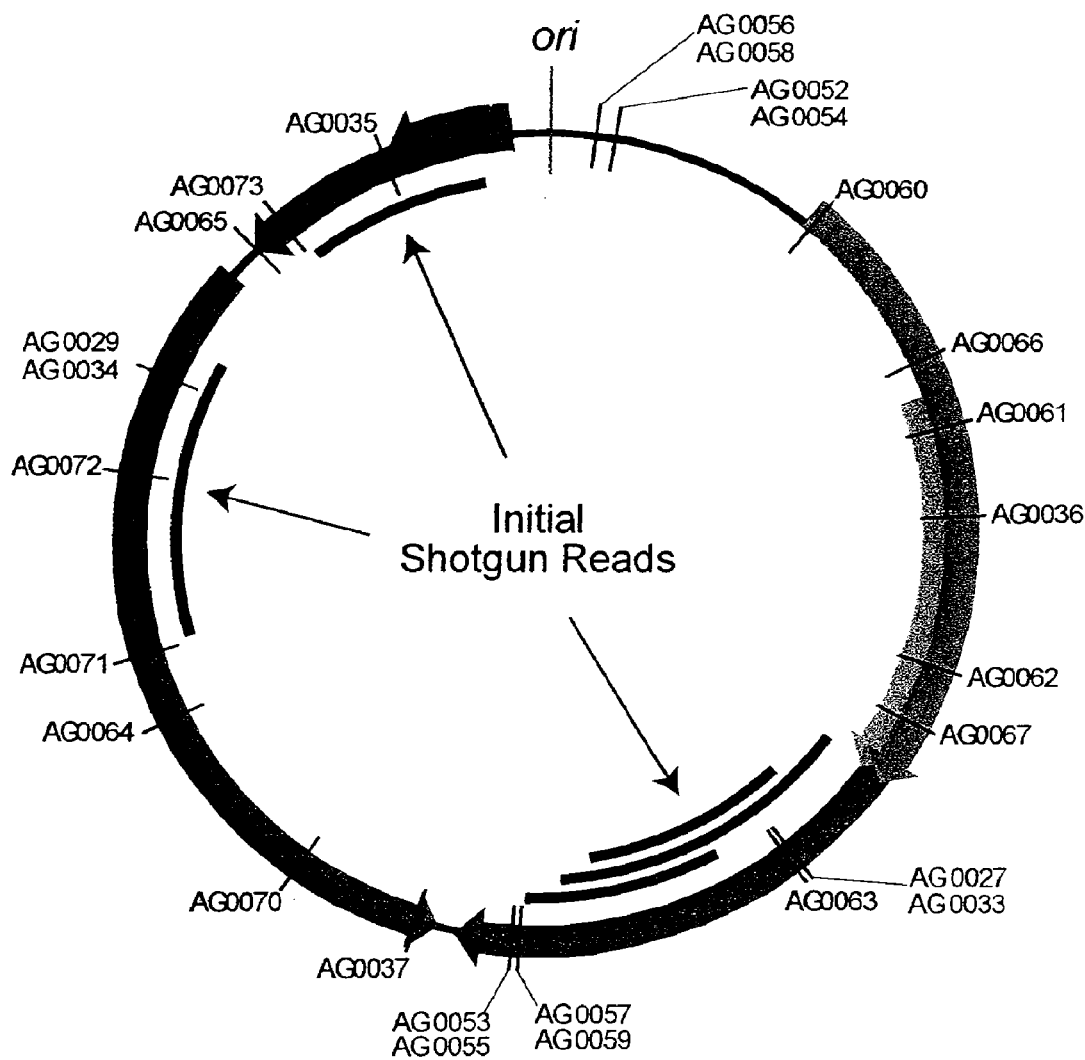

Strain variants. To assess the sequence variation within different isolates, we analyzed the 250 bp region encompassed by the initial screening primers for all 43 cases (FIG. 3). Several divergent strains were detected, including one sample that had 5 mutations (2%) within this region. In another case, a 12 bp deletion was observed. The fact that many isolates were identical in sequence was not surprising, given the relatively short length of the amplicon and the double stranded DNA nature of the genome. In addition, we sequenced the complete genome of 5 additional isolates. Unfortunately, insufficient specimen was available from the two most divergent isolates (based on the 250 bp sequence, B2 and B3) for complete genome sequencing of those strains. All 6 complete genomes were 5229 bp in size, and overall, there was between 0.08-0.23% sequence variation from sample to sample, well above that expected from Taq PCR, ruling out the possibility that the additional positives were artifacts of PCR contamination. Moreover, the majority of the observed mutations were synonymous substitutions or in non-coding regions lending further support to the argument that these were authentic strain variants. For JC virus, the reported intratype sequence variation is of a similar magnitude, ranging between 0.1-0.5% [23].

TABLE 4

Patients Positive for WU Virus

| ID | Age (years) | Sex | Sample Type | Clinical Findings | Viral Co-Infection |
|---|---|---|---|---|---|
| WU* | 3 | M | NPA | Pneumonia | |
| S1 | 51 | M | BAL | Unexplained Respiratory Failure, Ventilated | Herpes Simplex |
| S2 | 3 | M | NPS | Neuroblastoma | Metapneumo |

TABLE 4-continued

Patients Positive for WU Virus

| ID | Age (years) | Sex | Sample Type | Clinical Findings | Viral Co-Infection |
|---|---|---|---|---|---|
| S3 | 0.3 | M | NPS | URTI | Rhino |
| S4 | 2 | M | NPS | Febrile respiratory infection with patchy pulmonary infiltrates | Influenza B |
| S5 | 0.4 | F | NPS | URTI | Adeno |
| S6 | 19 | F | NPS | influenza-like illness, reactive airways disease, pregnant | Influenza B |
| B1 | 53 | M | BAL | LRTI, Wegners granulomatosis | |
| B2 | 0.9 | M | NPA | Bronchiolitis | |
| B3 | 43 | M | BW | HIV, Kaposi's Sarcoma | Epstein Barr |
| B4 | 2 | M | NPA | LRTI, Cystic Fibrosis | |
| B5 | 2 | M | NPA | LRTI, Post Bone Marrow Transplant | Respiratory Syncytial Virus |
| B6 | 1 | F | NPA | Gastroenteritis | Rhino |
| B7 | 0.9 | M | NPA | Bronchiolitis | Rhino |
| B8 | 0.8 | M | NPA | Bronchiolitis | Metapneumo, Rhino |
| B9 | 6 | M | NPA | LRTI, Febrile neutropaenia, ALL | Metapneumo |
| B10 | 1 | M | NPA | URTI, Gastroenteritis | |
| B11 | 2 | M | NPA | Pneumonia | |
| B12 | 2 | F | NPA | URTI | Bocavirus, Entero |
| B13 | 2 | M | NPA | LRTI, Cerebral Palsy | |
| B14 | 1 | M | NPA | URTI | |
| B15 | 2 | F | NPA | URTI | Influenza A |
| B16 | 2 | F | NPA | Bronchiolitis | Rhino |
| B17 | 0.6 | M | NPA | Bronchiolitis | Rhino |
| B18 | 2 | M | NPA | LRTI | Bocavirus |
| B19 | 0.6 | M | NPA | URTI, Gastroenteritis | Rhino |
| B20 | 1 | M | NPA | URTI | Bocavirus |
| B21 | 0.6 | M | NPA | Bronchiolitis | |
| B22 | 0.3 | M | NPA | URTI | Rhino |
| B23 | 0.6 | M | NPA | URTI | Rhino |
| B24 | 1 | F | NPA | URTI, Febrile Convulsion | Adeno, Rhino, Bocavirus |
| B25 | 0.8 | M | NPA | Bronchiolitis | |
| B26 | 3 | F | NPA | URTI | |
| B27 | 6 | F | NPA | URTI, Post Bone Marrow Transplant | |
| B28 | 2 | M | NPA | Infective exacerbation of bronchiectasis | Entero |
| B29 | 1 | F | NPA | LRTI | |
| B30 | 0.3 | M | NPA | URTI | Rhino, Bocavirus |
| B31 | 0.6 | M | NPA | Bronchiolitis | Rhino |
| B32 | 3 | F | NPA | URTI | Bocavirus |
| B33 | 1 | M | NPA | URTI | Rhino, Bocavirus |
| B34 | 0.8 | M | NPA | Bronchiolitis | Bocavirus, Parainfluenza 3 |
| B35 | 2 | F | NPA | LRTI | Rhino, Bocavirus |
| B36 | 0.9 | M | NPA | LRTI, ETT, Ventilated | Bocavirus |
| B37 | 2 | M | NPA | Croup | Rhino |

*Original case.
Abbreviations: NPA, nasopharyngeal aspirate; NPS, nasopharyngeal swab; BAL, bronchoalveolar lavage; BW, bronchial washings; URTI, upper respiratory tract infection; LRTI, lower respiratory tract infection; ALL, acute lymphoblastic leukemia; ETT, endotracheal tube in place Screening of urine. Because BK and JC virus are frequently excreted in urine, we examined urine samples from patient cohorts in both St. Louis and Brisbane for the presence of WU virus by PCR. In the St. Louis cohort, urine from 200 adult patients participating in a study of polyomavirus infections in kidney transplant recipients were tested [24]. For most patients, samples were tested at 3 time points: prior to transplant, 1 month post transplant, and 4 months post transplant, although for some patients the pre-transplant specimen was not available. Zero out of 501 samples tested were positive for the WU polyomavirus. As a control, using previously validated BK primers, we were able to amplify BK virus in a subset of these urine samples, confirming the integrity of the specimens themselves. Similarly, from the Brisbane cohort, none of the 226 urine samples tested were positive for WU virus.

Using a high throughput sequencing strategy to search for novel agents that were present in respiratory tract infections of unknown etiology, the WU virus was identified. The focus of this study was on individual clinical specimens that still lacked a diagnosis after analysis with an extensive panel of diagnostic assays for known respiratory viruses. In one such patient sample, novel sequences with limited homology to known polyomaviruses were detected. Complete genome sequencing and phylogenetic analysis revealed that the new virus clearly had the genomic organization typical of polyomaviruses but was highly divergent from all previously described polyomaviruses. Overall, the predicted amino acid sequences of WU virus proteins were most similar to the newly described KI virus (Table 3). Outside of KI, WU shared only between ~15-49% identity to its closest relatives (Table 3).

Detailed analysis of the viral DNA sequence and genomic organization confirmed the novelty of WU virus. At all loci, WU virus was most similar to KI virus, but the degree of divergence between WU and KI was greater than the divergence between SV40 and BK, indicating that WU and KI are clearly distinct viruses (FIG. 2). Based on the phylogenetic analysis, it appears that WU and KI define a novel branch within the Polyomaviridae family (FIG. 2). Relative to the established polyomaviruses, some analyses suggested that the WU/KI branch might be more closely related to the primate polyomaviruses while other features of the WU genome suggested that it might be more similar to murine polyomavirus. For example, neighbor joining phylogenetic analysis suggested that the predicted STAg, LTAg and VP1 open reading frames of both KI and WU were most closely related to SV40, JC, BK and baboon polyomaviruses. Analysis of the VP2/VP3 region was more equivocal as the proteins were too divergent to reliably assess. The apparent absence of the C-terminal "host range" domain in the LTAg and the agnoprotein open reading frame, both of which are present in the known primate polyomaviruses, suggested that WU virus was more similar to murine polyomavirus than the primate polyomaviruses by these criteria. While the evolutionary history of this virus is not clear at the moment, the totality of the analysis indicates that WU is clearly a unique virus.

WU was detected in 37 out of 1245 (3.0%) patient specimens in Brisbane (excluding the original case) and in 6 out of 890 (0.7%) patient specimens tested in St. Louis. As the positive specimens were all collected from 2003 through 2006, it appears that WU is currently circulating, and its presence in both North America and Australia suggests that the virus is widespread in the human population. The age range of patients that tested positive for WU virus spanned from 4 months to 53 years. The majority (86%) of the cases were found in children three years of age and under. Of the 4 positive specimens from adult patients (Table 4, S1, S6, B1 and B3), three clearly had altered immune status. One patient was HIV positive, one was immunosuppressed due to treatment for Wegener's granulomatosis, and one was pregnant. The fourth adult patient (S1) while not obviously immunosuppressed, also suffered from liver cirrhosis, hypertension, type 2 diabetes, coinfection with herpes simplex virus and required mechanical ventilation. In addition, there were two other positive patients older than 3 years of age: a 6 year old child who had previously been a bone marrow transplant recipient (Table 4, B27) and another 6 year old child diagnosed with acute lymphoblastic leukemia (Table 4, B9). While preliminary, the age distribution of the positive cases in this study combined with the established paradigms for BK and JC virus suggest a model where acute infection with WU virus may occur relatively early in life and result in a latent infection. Immunosuppression or other insults such as viral infection could then lead to reactivation of WU virus in older individuals.

The patients who yielded positive specimens suffered from a wide range of respiratory syndromes including bronchiolitis, croup and pneumonia as well as other clinical maladies (Table 4). Detection of WU virus in these patients is merely the first step in assessing the potential etiologic role of WU virus in acute respiratory tract disease. It is possible that WU is not involved at all in respiratory disease, but rather is simply transmitted by the respiratory route. The human polyomaviruses BK and JC are hypothesized to be transmitted by the respiratory route before taking up residency primarily in the kidneys. Latency in the kidneys of BK and JC is believed to be the reason that both viruses are excreted in the urine of up to 20% of asymptomatic individuals [13] [14]. In this study, using the same PCR assays that were effective in respiratory secretions, we did not detect WU in any of the 727 urine samples we tested. The lack of detection of WU virus in the urine may reflect sensitivity issues, a bias in the cohorts tested, or simply that WU is unlike BK and JC viruses and is not secreted in the urine. Future experiments will aim to determine the tissue tropism of WU and whether any tissue reservoirs for WU virus exist.

In the literature, there is one animal polyomavirus that has been found extensively in lung tissue. Infection of suckling mice with the mouse pneumotropic polyomavirus (MPPV) causes interstitial pneumonia and significant mortality. MPPV also differs from other polyomaviruses in that besides the kidneys, it can also be detected in the lungs, liver, spleen and blood of suckling mice [27]. Thus, there is precedence for an animal polyomavirus causing respiratory disease suggesting that WU virus is similarly pathogenic in humans.

One striking observation from these studies is the relatively high frequency of co-infection detected in the respiratory secretions: 72% overall (100% in the St. Louis cohort and 68% in the Brisbane cohort). Although more extensive studies are necessary to confirm the generality of this observation, this raises several intriguing non-mutually exclusive possibilities to consider: 1) WU may be an opportunistic pathogen; 2) WU infection may predispose or facilitate secondary infection by other respiratory viruses; and 3) WU may be a part of the endogenous viral flora that is reactivated by inflammation or some other aspect of viral infection. Recent studies of the prevalence of the newly identified human bocavirus have also reported higher levels of co-infection than previously described for other viruses found in the respiratory tract with co-infection rates as high as 50% reported [28] [29]. As detection methods improve in sensitivity and more comprehensive efforts are made to examine the diversity of viruses found in the respiratory tract, a greater appreciation for the rates of dual or multi-infection is gradually emerging. For example, the use of extensive panels of PCR assays in this study revealed that one of the positive specimens was quadruply infected; adenovirus, rhinovirus and bocavirus and WU virus were all present. Further investigations that aim to systematically define the spectrum of viruses present in the respiratory tract are clearly warranted so that the possible roles that co-infections may play in disease pathogenesis can be explored.

Extremely high sequence divergence was observed in the capsid proteins VP1 and VP2 of WU virus and KI virus as compared to the other known polyomaviruses. This divergence may reflect a different 'lifestyle' for the WU/KI branch as compared to known polyomaviruses. Our data demonstrating the presence of WU in respiratory secretions and the absence in urine samples, suggest that the mode of transmission or the sites of persistence of WU may be distinct from the other human polyomaviruses. As such, the structure of the virion must be optimized to enable the virus to survive dramatically distinct physiological and environmental conditions. This may partially explain the observed sequence divergence in the capsid proteins.

Another question raised by this study relates to the potential antigenic cross reactivity of the WU capsid proteins. In terms of establishing the seroprevalence of WU itself and determining whether seroconversion accompanies acute infection with WU, it will be essential to conduct these studies with consideration for potential cross reactivity to BK, JC and SV40 antibodies. In addition, it is tantalizing to speculate whether serum antibodies to WU have the potential to cross react to SV40 derived antigens, and if so, whether they may at least partially account for some of the studies that report the presence of SV40 antibodies in the human population that is too young to have suffered exposure from contaminated polio vaccination [30] [31,32].

The genome of a novel polyomavirus has been identified and completely sequenced. This virus appears to be geographically widespread in the human population as evidenced by the detection of 44 distinct cases in two continents. Based on preliminary analysis, WU and KI virus share some strikingly similar properties including their complement of genes, phylogenetic relationship and physical sites of detection in the human body. These data suggest that WU virus and KI virus define a novel branch within the Polyomaviridae family with unexplored biology and pathogenicity. Another implication of these results is that the diversity of viruses in this family may be far greater than currently realized. Further experimentation is now underway to determine the relative pathogenicity of WU virus in humans and to understand the molecular properties of the virus. Since the TAg of WU is predicted to have transforming properties by analogy to other polyomavirus TAgs, one question currently under investigation is whether a subset of human tumors may be associated with WU.

Clinical Specimens—Respiratory Secretions.

Brisbane cohort. 1245 specimens (predominantly nasopharyngeal aspirates) were collected between Jan. 1, 2003 to Dec. 22, 2003 from patients presenting to the Royal Children's Hospital in Brisbane, Australia with symptoms consistent with acute lower respiratory tract infection.

St. Louis cohort #1. A total of 480 BAL specimens were tested. These included samples from a retrospective and a prospective collection. The retrospective specimens were from a sequential collection of BAL specimens submitted routinely to the Virology Laboratory at St. Louis Children's Hospital between December 2002 to August 2003 [33]. For the present study, an effort was made to select specimens from this collection from patients with acute respiratory illness, and to exclude specimens collected as routine post-lung transplant surveillance. The prospective specimens were from an ongoing study of the etiology of severe acute respiratory illness and were collected between October 2005 and October 2006. Both collections included specimens from patients of all ages, although the large majority were from adults.

St. Louis cohort #2. This collection was made up of respiratory specimens, mostly nasopharyngeal swabs, submitted for routine virologic testing to the Virology Laboratory at St. Louis Children's Hospital between September 2005 and June 2006. The majority of these specimens were from children. Of the 410 specimens in this collection, 200 were selected because they had been found to be positive by fluorescent antibody staining or culture for influenzavirus A or B, respiratory syncytialvirus, parainfluenza virus, rhinovirus, or adenovirus.

Clinical Specimens—Urine

Brisbane cohort: 226 urine specimens that were submitted during 2003 to the diagnostic laboratory for routine investigation were collected. These represented a diverse mixture of donors including those from: (i) sexual health clinic (n=50), (ii) pediatric clinic (n=52), (iii) antenatal clinic (n=33), (iv) indigenous health clinic (n=36) and (v) bone marrow transplant patients (n=55).

The St. Louis urine specimens were from a study of polyomaviruses in adult renal transplant recipients [24]. A total of 200 individuals were enrolled in the study between December 2000 and October 2002. From each patient, up to 3 specimens were tested, including a specimen obtained before the transplant and specimens obtained at 1 and 4 months after transplantation.

Diagnostic Testing of Clinical Specimens for Known Respiratory Viruses.

Brisbane cohort. Nucleic acids were extracted from 0.2 ml of each specimen using the High Pure Viral Nucleic Acid kit (Roche Diagnostics, Australia), according to the manufacturer's instructions. PCR assays for 17 known respiratory viruses were performed as described [19].

St. Louis Cohort: All respiratory specimens were tested originally by fluorescent antibody staining using a panel of monoclonal antibodies directed against influenza A and B, respiratory syncytial, parainfluenza 1-3, and adenoviruses (Simulfluor Respiratory Screen, Chemicon International Inc, Temecula Calif.). Specimens that were negative were also cultured using cell culture systems that could detect the same group of viruses plus rhinoviruses, cytomegalovirus, and herpes simplex virus. Total nucleic acid extracts were purified using a Qiagen M48 instrument. Nucleic acid extracts were tested for a panel of respiratory viruses using the Eragen MultiCode-PLx respiratory virus panel (Eragen Biosciences, Inc, Madison Wis.), a multiplex PCR assay that detects the following viruses: influenza A and B, respiratory syncytial virus A and B, parainfluenza 1-4, human meatpneumovirus, adenovirus subgroups B, C, and E, rhinoviruses, and coronaviruses OC43, 229E, and NL63.

Library construction and shotgun sequencing. 200 ul of the nasopharyngeal aspirate sample was treated with DNase I (Fermentas) for 60 min at 37 C. Total nucleic acid was extracted using the Masterpure Complete DNA and RNA Purification Kit (Epicentre Biotechnologies, Madison Wis.). 100 nanograms of total nucleic acid was randomly amplified using the RdAB protocol exactly as described [8]. Amplified nucleic acid was TOPO cloned into pCR4.0 (Invitrogen, Carlsbad, Calif.), transformed into bacteria, and white colonies were picked into 384 well plates. DNA was purified by magnetic bead isolation and sequenced using standard Big Dye terminator (v 3.1) sequencing chemistry. Reaction products were ethanol precipitated, resuspended in 25 ul of water and loaded onto the ABI 3730x1 sequencer. Viral sequences were identified by performing sequence alignments using BLASTx against publicly available Genbank databases.

Complete genome amplification and sequencing. The WU genome derived from the index case was sequenced to 3× coverage using 6 unique pairs of PCR primers for the amplification. Amplicons were cloned into pCR4.0 and sequenced using standard sequencing technology. All primers used for amplification and sequencing are listed in Table 5. Additional complete genomes were sequenced to at least 2× coverage using the same primers listed in Table 5. Completed genome sequences have been deposited into Genbank (Accession#s EF444549-EF444554).

TABLE 5

| Amplification Primers | | | Sequencing Primers | |
|---|---|---|---|---|
| Name | Sequence | Size | Name | Sequence |
| AG0027 | GCCAGCATTAAGCACAGGA (SEQ ID NO: 58) | 3043 bp | M13F | GTAAAACGACGGCCAG (SEQ ID NO: 59) |
| AG0029 | GCTTGAGACACAAATTCTTCCA (SEQ ID NO: 60) | | M13R | CAGGAAACAGCTATGAC (SEQ ID NO: 61) |
| | | | AG0035 | TGCATTCTACCTGTGAAGAGC (SEQ ID NO: 62) |
| | | | AG0036 | GCATTTACTGGGTCAGATTCC (SEQ ID NO: 63) |

TABLE 5-continued

| Amplification Primers | | | Sequencing Primers | |
|---|---|---|---|---|
| Name Sequence | Size | Name | Sequence | |
| AG0033 TCCTGTGCTTAATGCTGGC (SEQ ID NO: 64) <br> AG0034 TGGAAGAATTTGTGTCTCAAGC (SEQ ID NO: 66) | 2229 bp | M13F <br> M13R <br> AG0037 | GTAAAACGACGGCCAG (SEQ ID NO: 65) <br> CAGGAAACAGCTATGAC (SEQ ID NO: 67) <br> TGCATGTCAGCAAATTCAGT (SEQ ID NO: 68) | |
| AG0052 TTATGTGCAGGAATGTGCAG (SEQ ID NO: 69) <br> AG0053 CTCTACTGTGGGAGGCAAGG (SEQ ID NO: 71) | 2552 bp | M13F <br> M13R <br> AG0066 <br> AG0067 | GTAAAACGACGGCCAG (SEQ ID NO: 70) <br> CAGGAAACAGCTATGAC (SEQ ID NO: 72) <br> CAGGATACAATCCCCAAGGA (SEQ ID NO: 73) <br> ACCTTCCTGGTTTTGCTGTG (SEQ ID NO: 74) | |
| AG0054 CTGCACATTCCTGCACATAA (SEQ ID NO: 75) <br> AG0055 CCTTGCCTCCCACAGTAGAG (SEQ ID NO: 77) | 2679 bp | M13F <br> M13R <br> AG0064 <br> AG0065 | GTAAAACGACGGCCAG (SEQ ID NO: 76) <br> CAGGAAACAGCTATGAC (SEQ ID NO: 78) <br> ACCAGGCTACACCAGCCATA (SEQ ID NO: 79) <br> ATGCAAGGGGTTGGCTTAAC (SEQ ID NO: 80) | |
| AG0056 TAGCAGCCACAAGGTGGAGC (SEQ ID NO: 81) <br> AG0057 AAGGGCCCTGTTTCTTCAGT (SEQ ID NO: 83) | 2576 bp | M13F <br> M13R <br> AG0060 <br> AG0061 <br> AG0062 <br> AG0063 | GTAAAACGACGGCCAG (SEQ ID NO: 82) <br> CAGGAAACAGCTATGAC (SEQ ID NO: 84) <br> ATGGGCATATTGCTTGCTGT (SEQ ID NO: 85) <br> TTCATTGCATCCCACCTGCC (SEQ ID NO: 86) <br> ATGCAGCCCCTGACTGGATT (SEQ ID NO: 87) <br> GCTGGCATACTTTACTACAGG (SEQ ID NO: 88) | |
| AG0058 GCTCCACCTTGTGGCTGCTA (SEQ ID NO: 89) <br> AG0059 ACTGAAGAAACAGGGCCCTT (SEQ ID NO: 91) | 2655 bp | M13F <br> M13R <br> AG0070 <br> AG0071 <br> AG0072 <br> AG0073 | GTAAAACGACGGCCAG (SEQ ID NO: 90) <br> CAGGAAACAGCTATGAC (SEQ ID NO: 92) <br> TGTTACAATACCTGGAGGAA (SEQ ID NO: 93) <br> CCACATCAATAGCCTGTTGA (SEQ ID NO: 94) <br> GCTAATAGTACAGTATCCCT (SEQ ID NO: 95) <br> CAAAGCCAAACCACTCTCTA (SEQ ID NO: 96) | |

Phylogenetic analysis. Protein sequences associated with the following reference virus genomes were obtained from Genbank: BK virus (NC__001538); JC virus (NC__001699); Bovine polyomavirus (NC__001442); SV40 (NC__001669); Baboon polyomavirus (simian agent 12) (NC__007611); Finch polyomavirus (NC__007923); Crow polyomavirus (NC__007922); Goose hemorrhagic polyomavirus (NC__004800); African green monkey polyomavirus (NC__004763); Budgerigar fledgling polyomavirus (NC__004764); Murine pneumotropic virus (NC__001505); Hamster polyomavirus (NC__00163); Murine polyomavirus (NC__001515). For WU virus, predicted ORFS were used. For STAg, the predicted ORF of 194 amino acids was used for analysis. Multiple sequence alignment was performed using ClustalX (1.83). Neighbor joining trees were generated using 1000 bootstrap replicates. Maximum parsimony trees were generated using PAUP 4.0 [34].

Nucleic acid prevalence studies. For all PCR assays, standard precautions to avoid end product contamination were taken, including the use of PCR hoods and maintaining separate areas for PCR set up and analysis. For initial screening of WU virus, PCR primers AG0044 5' TGTTACAAATAGCTGCAGGTCAA (SEQ ID NO:97) and AG0045 5' GCTGCATAATGGGGAGTACC (SEQ ID NO:98) were used with Accuprime hot start Taq (Invitrogen) to amplify 1 ul of template using the following program: 40 cycles of 94 C 30 sec; 56 C 30 sec; 72 C 60 sec. For every 88 samples tested, 7 no-template negative controls were interspersed between the actual samples. Products were visualized following electrophoresis on 1% agarose gels. The resulting 250 bp amplicon were sequenced directly in both directions using primer AG0044 and AG0045. These sequences have been deposited in Genbank (Accession#s EF444555-EF444593). Secondary confirmation was performed using Primers AG0048 5'TGTTTTTCAAGTATGTTGCATCC (SEQ ID NO:99) and AG0049 5' CACCCAAAAGACACTTAAAAGAAA (SEQ ID NO:100) that generate a 244 bp amplicon in the 3' end of the LTAg coding region. The same cycling profile of 40 cycles of 94 C 30 sec; 56 C 30 sec; 72 C 60 sec was used. For detection of both BK and JC viruses, primers AG0068 5' AGTCTTTAGGGTCTTCTACC (SEQ ID NO:101) and AG0069 5'GGTGCCAACCTATGGAACAG (SEQ ID NO:102) were used with a profile of 40 cycles of 94 C 30 sec; 56 C 30 sec; 72 C 60 sec.

REFERENCES

1. Mulholland K (2003) Global burden of acute respiratory infections in children: implications for interventions. Pediatr Pulmonol 36: 469-474.
2. Heikkinen T, Jarvinen A (2003) The common cold. Lancet 361: 51-59.
3. van den Hoogen B G, de Jong J C, Groen J, Kuiken T, de Groot R, et al. (2001) A newly discovered human pneumovirus isolated from young children with respiratory tract disease. Nat Med 7: 719-724.
4. Ksiazek T G, Erdman D, Goldsmith C S, Zaki S R, Peret T, et al. (2003) A novel coronavirus associated with severe acute respiratory syndrome. N Engl J Med 348: 1953-1966.
5. van der Hoek L, Pyrc K, Jebbink M F, Vermeulen-Oost W, Berkhout R J, et al. (2004) Identification of a new human coronavirus. Nat Med 10: 368-373.
6. Woo P C, Lau S K, Chu C M, Chan K H, Tsoi H W, et al. (2005) Characterization and complete genome sequence of a novel coronavirus, coronavirus HKU1, from patients with pneumonia. J Virol 79: 884-895.
7. Allander T, Tammi M T, Eriksson M, Bjerkner A, Tiveljung-Lindell A, et al. (2005) Cloning of a human parvovirus by molecular screening of respiratory tract samples. Proc Natl Acad Sci USA 102: 12891-12896.
8. Wang D, Urisman A, Liu Y T, Springer M, Ksiazek T G, et al. (2003) Viral discovery and sequence recovery using DNA microarrays. PLoS Biol 1: E2.
9. Stolt A, Sasnauskas K, Koskela P, Lehtinen M, Dillner J (2003) Seroepidemiology of the human polyomaviruses. J Gen Virol 84: 1499-1504.
10. Goudsmit J, Wertheim-van Dillen P, van Strien A, van der Noordaa J (1982) The role of BK virus in acute respiratory tract disease and the presence of BKV DNA in tonsils. J Med Virol 10: 91-99.
11. Sundsfjord A, Spein A R, Lucht E, Flaegstad T, Seternes O M, et al. (1994) Detection of BK virus DNA in nasopharyngeal aspirates from children with respiratory infections but not in saliva from immunodeficient and immunocompetent adult patients. J Clin Microbiol 32: 1390-1394.
12. Arthur R R, Shah K V, Baust S J, Santos G W, Saral R (1986) Association of BK viruria with hemorrhagic cystitis in recipients of bone marrow transplants. N Engl J Med 315: 230-234.
13. Markowitz R B, Thompson H C, Mueller J F, Cohen J A, Dynan W S (1993) Incidence of BK virus and JC virus viruria in human immunodeficiency virus-infected and -uninfected subjects. J Infect Dis 167: 13-20.
14. Behzad-Behbahani A, Klapper P E, Vallely P J, Cleator G M, Khoo S H (2004) Detection of BK virus and JC virus DNA in urine samples from immunocompromised (HIV-infected) and immunocompetent (HIV-non-infected) patients using polymerase chain reaction and microplate hybridisation. J Clin Virol 29: 224-229.
15. Shah K V (2004) Simian virus 40 and human disease. J Infect Dis 190: 2061-2064.
16. Bikel I, Montano X, Agha M E, Brown M, McCormack M, et al. (1987) SV40 small t antigen enhances the transformation activity of limiting concentrations of SV40 large T antigen. Cell 48: 321-330.
17. Hahn W C, Counter C M, Lundberg A S, Beijersbergen R L, Brooks M W, et al. (1999) Creation of human tumour cells with defined genetic elements. Nature 400: 464-468.
18. Poulin D L, DeCaprio J A (2006) Is there a role for SV40 in human cancer? J Clin Oncol 24: 4356-4365.
19. Arden K E, McErlean P, Nissen M D, Sloots T P, Mackay I M (2006) Frequent detection of human rhinoviruses, paramyxoviruses, coronaviruses, and bocavirus during acute respiratory tract infections. J Med Virol 78: 1232-1240.
20. Altschul S F, Madden T L, Schaffer A A, Zhang J, Zhang Z, et al. (1997) Gapped BLAST and PSI-BLAST: a new generation of protein database search programs. Nucleic Acids Res 25: 3389-3402.
21. Cantalupo P, Doering A, Sullivan C S, Pal A, Peden K W, et al. (2005) Complete nucleotide sequence of polyomavirus SA12. J Virol 79: 13094-13104.
22. Pipas J M (1992) Common and unique features of T antigens encoded by the polyomavirus group. J Virol 66: 3979-3985.
23. Agostini H T, Ryschkewitsch C F, Brubaker G R, Shao J, Stoner G I (1997) Five complete genomes of JC virus type 3 from Africans and African Americans. Arch Virol. pp. 637-655.
24. Brennan D C, Agha I, Bohl D L, Schnitzler M A, Hardinger K L, et al. (2005) Incidence of BK with tacrolimus versus cyclosporine and impact of preemptive immunosuppression reduction. Am J Transplant 5: 582-594.
25. Gardner S D, Field A M, Coleman D V, Hulme B (1971) New human papovavirus (B.K.) isolated from urine after renal transplantation. Lancet 1: 1253-1257.
26. Padgett B L, Walker D L, ZuRhein G M, Eckroade R J, Dessel B H (1971) Cultivation of papova-like virus from human brain with progressive multifocal leucoencephalopathy. Lancet 1: 1257-1260.
27. Greenlee J E (1981) Effect of host age on experimental K virus infection in mice. Infect Immun 33: 297-303.
28. Sloots T P, McErlean P, Speicher D J, Arden K E, Nissen M D, et al. (2006) Evidence of human coronavirus HKU1 and human bocavirus in Australian children. J Clin Virol 35: 99-102.
29. Choi E H, Lee H J, Kim S J, Eun B W, Kim N H, et al. (2006) The association of newly identified respiratory viruses with lower respiratory tract infections in Korean children, 2000-2005. Clin Infect Dis 43: 585-592.
30. Jafar S, Rodriguez-Barradas M, Graham D Y, Butel J S (1998) Serological evidence of SV40 infections in HIV-infected and HIV-negative adults. J Med Virol 54: 276-284.
31. Minor P, Pipkin P, Jarzebek Z, Knowles W (2003) Studies of neutralising antibodies to SV40 in human sera. J Med Virol 70: 490-495.
32. Lundstig A, Eliasson L, Lehtinen M, Sasnauskas K, Koskela P, et al. (2005) Prevalence and stability of human serum antibodies to simian virus 40 VP1 virus-like particles. J Gen Virol 86: 1703-1708.
33. Sumino K C, Agapov E, Pierce R A, Trulock E P, Pfeifer J D, et al. (2005) Detection of severe human metapneumovirus infection by real-time polymerase chain reaction and histopathological assessment. J Infect Dis 192: 1052-1060.
34. Swofford D L (2002) PAUP. Phylogenetic Analysis Using Parsimony (and Other Methods). Sunderland, Mass.: Sinauer Associates.
35. Allander T, Andreasson K, Gupta S, Bjerkner A, Bogdanovic G, et al. (2007) Identification of a third human polyomavirus. J. Virol. ePub PMID: 17287263.

SEQUENCE LISTING

<160> NUMBER OF SEQ ID NOS: 151

<210> SEQ ID NO 1
<211> LENGTH: 5229
<212> TYPE: DNA
<213> ORGANISM: Polyomaviridae WU

<400> SEQUENCE: 1

```
gcctcaggcc tccttattat aataaaaaaa agctaagcat gattgacagt gtgggctaaa        60
ccaaaagcac aagaacaaag cttttagcca attagcagcc acaaggtgga gcaaaagtat       120
taagtttcac tgttatgtgc aggaatgtgc agctgtgacc ttttaaagtt tccgggcacg       180
gcgccaactt cctgggcctg gtgccatacc aacacagctg ctgagcttcc ggaatacaat       240
actggtgccc tttgtaagtg ttttacaggt aagtaaggcc tacaacaggg cttatttgta       300
ctataagtta atgggggccc tttgtagtcc agcggaaagt gaaggtggc ttaacagaga        360 cgtccttggg ttcaaaccta agggtgccat aagcaacatt acattaatgt tgtgacatct       420
ccagtcgggg gtattggcct ataggaaacc ctagggctct ataagcagca tacatatgtt       480
gtgacatctc cgttgagtct gggggtattg gtgctaccgt ctcgaaccta gccgacagcc       540
gttggatata aagggtcacc atttttattt cagatgggca tattgcttgc tgtgcctgaa       600
ataattgctg catctgtagc tggaggagca gaggcactat caattgctgg atctggagct       660
gcaatagcaa ctggtgaagg tttagctgct cttggtgggc ttacagagtc agcagcacta       720
ttaggggaaa ctgttgaaat atctgaagca gctgctactg tactaacaaa agtacctgag       780
cttgtaactg taacacaagg tgtaacagca gctgtacaag ggggtgcagg tcttgtaggt       840
ggtatatata cagctttagc agcagatcgc cctggggacc tgcctgcgag tacccccaaca      900 ggaagtccaa gtggactaca tcccccccgca ggatacaatc cccaaggagg tggacttaat       960
atccagtcca tccacaagcc cctccacgcc cctacccag gaatggcact ggcacctatc       1020
cctgaataca acttggaaac tggaattcca ggggtcccgg actgggtatt caacttcatt      1080
gcatcccacc tgcccgagtt gcctagcctg caggacgtgt tcaatagaat tgcctatgga      1140
atctggacat catattacaa tacggggaga acagtagtta atagagcagt tagtgaagaa      1200
ttacaaagac tactaggaga tttagaatat ggatttagaa ctgcacttgc caccattggg      1260
gaatctgacc cagtaaatgc tatagttgaa caagtaagaa gctttgttag tggaggaaga      1320
gaaagagaac tgttacaaat agctgcaggt caacctgtag acatttctga aggtgtatca      1380
agaggcacag ctactatttc aaatgctgta aagctgtaa agatgcaac tcaaagacta        1440 tcacaagcaa cctacaactt tgtttatgat gcttctaccc ttccaaggga tggctttaat      1500
gcacttagtg atggagttca cagactaggc cagtggattt caatgcctgg ggctacaggg      1560
ggtactcccc attatgcagc ccctgactgg atttatatg tacttgaaga gctaaacagt        1620
gacatttcta aaattcctac acagggaatt aaaagaaaac tacaacaaaa tggcctgcac      1680
agcaaagcca gcctgcacag caaaaccagg aaggtcacca agaagtcaac ccacaagagt      1740
gcaaagcctt ccaaaacaag tcagaaaagg aggggtagac gtgctggccg ccgtaccact      1800
gtcagaagaa acagagttta agttgaatt gtttgttaaa cctgttattg gaatgcaga       1860 ggggactacc ccacattatt ggtctattag tagcccactt aaaactgctg aagctgctaa      1920
tgttactcct gatgctgata ctactgtgtg ctacagcttg tcacaggttg ctcccccctga     1980 tattcctaat caggttagtg aatgtgacat gcttatatgg gagctgtata gaatggaaac      2040
```

```
agaagttttg gtgcttcctg tgcttaatgc tggcatactt actacagggg gtgtaggagg      2100
tattgctggt ccccaacttt attttttgggc agttggagga cagcccttgg atgtgctagg      2160
acttgctccc actgaaaaat acaaggggcc tgctcagtat actgtaaatc ctaaaaccaa      2220
tggtactgtg cctcatgttt attccagttc tgaaacaccc agggcaaggg tcactaatga      2280
aaagtacagc attgaatcat gggtggcaga ccctagccgc aatgataact gcagatactt      2340
tggcagaatg gttggagggg ctgcaactcc accagtggtg tcatttagta ataatagcac      2400
aattccactg ttggatgaaa atggcattgg cattctttgc ttgcaaggta gattgtacat      2460
aacttgtgct gacctttttgg gagttaacaa aaatagagta catacagggc tttccagatt      2520
ttttaggcta cactttagac aaagaagggt tagaaaccca tatactataa atttgcttta      2580
taagcaggtt tttaataagc cagctgatga cattagtggg caactgcagg ttacagaggt      2640
tactatgact gaagaaacag ggcccttgcc tcccacagta gagggaaatg ttggtgtacc      2700
cacaaccagt aatttgtctc atttgcctgc aactgtaact ttacaagcca caggcccaat      2760
actaaacaca caaggataat gtaataaatg cagtttatta ataaagcaat tttaagcatt      2820 gtgttttttca agtatgttgc atccatttgt tacattcatt tgcatgtcag caaattcagt      2880
aaggcctata tatttgtcta acagttcttt ccaatacaca actttagctt gtatacatgg      2940
gtgaaaatca ctaacaggcc tgcaccatat taacataatt aaaatacaca ttccactttg      3000
taaaactctt ttkaccatta gttctggagt tttatccaga cttttctttta agtgtctttt      3060 gggtgtaaaa agtacagttt tatgaaatct aggagccaaa gtagcaggga ctaaatattc      3120
attcattgtt acaatacctg gaggaaaaat ttgtgacctt ttatttaaat gttttttttc      3180
taaattaact ttaacacttc catctaaata gtctcttaaa ttatctaagt tactcattcc      3240
atttccagat ggtaacagtt tattatctcc tacttgacct tttacatctt caaatactac      3300
tgtaaattga tctattgcaa ctcctaactc aaagtttaat ctatcagctg gaatattaat      3360
atttaaggcc tttcctccac aaaggtcaag taaagcagca gcaacagttg ttttaccact      3420
gtttataggc cccttaaaaa cccaatacct ttttttaggt acattttcaa ctataacttt      3480
taggtacctg tatacaagct catctatttt accatttagg cctaaatacc aggctacacc      3540
agccatatat aataaaacat cttgctcacc tttaatagtt ttatccattt tgtccagtat      3600
tttttcaaat cttctagcta ataaatcttc tctggacata tttaaactat ctacccttct      3660
ttttgcaata accacatcaa tagcctgttg acacacattt ttttgacttt tactgtctga      3720
aaatagtaaa gcattttttt gatgttccat atgaagtcta tatgagttg catcttcatt      3780 actattgcat ttttcacact cttctacctt aatagatagt tgtaaatata atccaagtaa      3840
taagtacaca tcatcaattc ctaattctaa agcaaattct gacaaagcct tccaatttaa      3900
ttgatcttta aactccccat ataaatcctc agctttaaaa tcatttttctt ttaagccacc      3960 aggaatattt tcttcacata aagtaaatgg atctctagtc attctactat ataaaccata      4020
tgcattatta acacctttac aaaataaaaa gctaatagta cagtatccct tacaaaagtt      4080
attaacagca ctaactctat gtctaaaagg tgttaaaata aacacaagtg cagtattata      4140
ataagaatgt ctacttgcaa aattacattt aaacttactt aaaagttttt tatatagggt      4200
ttctgccttt tctttggtgg tatgtattac aaatgcagtt aaagttctat tactaaatac      4260
agcttgagac acaaattctt ccaattcttt aggaaatgat aaagatgcat ctgtagcatt      4320
gtcctttttt tttttaggtg gtgttgcctg tgaacattgt ggttcctcat catcttctct      4380
agtacgcttt gtaggggttt ctccaggaga tttaggcatt tcctcattac atcttagttc      4440
```

-continued

```
ttcttcccag taggaattaa actgagacca ccagtaatcc cagtctgggg taccatatgt      4500
gggtatctat aataaaaaaa aattattaat ttacttataa aacataaaag taccccctata     4560 ataaaaacat gcttacctgg ttaagccaac cccttgcatg gttgtaagaa atataatctt      4620
tttccagtaa aaaaatgttt ctgcactaat ttcaaagcca aaccactctc tatagcacct      4680
gtagcagtaa cactctatcc acattggagg ttttctaaat attttatatt tttgcttgtg      4740
gcgcttgtct aaaaagcagt aaaaacaatt acacaaataa taaaacccct ttaagcatat      4800
gtcccagtct tttaaaatat actcttcaaa aacatcacca taaacttctc caacaagcct      4860
gtactttcta gggggaaagt tacagcacaa ttctgtgcat tctacctgtg aagagctcca      4920
cacttcatct tcttcttcat ttagttggtg cactgtacta acacactctt gcagttttaa      4980
atataaagaa ttaagctttt tcattttttc ctcatttccc cctttgtcag gatgaaattc      5040
tttgcatttg ctaaggtatt ttgttctcat tagtggtaaa tttccccagc aggtcatatc      5100
aagacccagc agctgcataa gttcttttgc ttcatttctg gacaaagttt tatccatttt      5160
gccttcttta gcctcaaggc gcctcagcaa ggccctctgc ttttagttca gaaagttgag      5220
gcttttag                                                              5229
```

<210> SEQ ID NO 2
<211> LENGTH: 5230
<212> TYPE: DNA
<213> ORGANISM: Polyomaviridae WU Strain SL

<400> SEQUENCE: 2

```
gcctcaggcc tccttattat aataaaaaaa agctaagcat gattgacagt gtgggctaaa       60
ccaaaagcac aagaacaaag cttttagcca attagcagcc acaaggtgga gcaaaagtat      120
taagtttcac tgttatgtgc aggaatgtgc agctgtgacc ttttaaagtt tccgggcacg      180
gcgccaactt cctgggcctg gtgccatacc aacacagctg ctgagcttcc ggaatacaat      240
actggtgccc tttgtaagtg ttttacaggt aagtaaggcc tacaacaggg cttatttgta      300
ctataagtta atggggcgcc tttgtagtcc agcggaaagt gaagggtggc ttaacagaga      360
cgtccttggg ttcaaaccta agggtgccat aagcaacatt acattaatgt tgtgacatct      420
ccagtcgggg gtattggcct ataggaaacc ctagggctct ataagcagca tacatatgtt      480
gtgacatctc cgttgagtct gggggtattg gtgctaccgt ctcgaaccta gccgacagcc      540
gttggatata aagggtcacc atttttattt cagatgggca tattgcttgc tgtgcctgaa      600
ataattgctg catctgtagc tggaggagca gaggcactat caattgctgg atctggagct      660
gcaatagcaa ctggtgaagg tttagctgct cttggtgggc ttacagagtc agcagcacta      720
ttaggggaaa ctgttgaaat atctgaagca gctgctactg tactaacaaa agtacctgag      780
cttgtaactg taacacaagg tgtaacagca gctgtacaag ggggtgcagg tcttgtaggt      840
ggtatatata cagctttagc agcagatcgc cctggggacc tgcctgcgag taccccaaca      900
ggaagtccaa gtggactaca tcccccccgca ggatacaatc cccaaggagg tggacttaat      960
atccagtcca tccacaagcc cctccacgcc cctacccag gaatggcact ggcacctatc     1020
cctgaataca acttggaaac tggaattcca ggggtcccgg actgggtatt caacttcatt     1080
gcatcccacc tgcccgagtt gcctagcctg caggacgtgt tcaatagaat tgcctatgga     1140
atctggacat catattacaa tacggggaga acagtagtta atagagcagt tagtgaagaa     1200
ttacaaagac tactaggaga tttagaatat ggatttagaa ctgcacttgc caccattggg     1260
gaatctgacc cagtaaatgc tatagttgaa caagtaagaa gctttgttag tggaggaaga     1320
```

```
caaagagaac tgttacaaat agctgcagyt caacctgtag acatttctga aggtgtatca    1380
agaggcacag ctactatttc aaatgctgta gaagctgtaa gagatgcaac tcaaagacta    1440
tcacaagcaa cctacaactt tgtttatgat gcttctaccc ttccaaggga tggctttaat    1500
gcacttagtg atggagttca caggctaggc cagtggattt caatgcctgg ggctacaggg    1560
ggtactcccc attatgcagc ccctgactgg attttatatg tacttgaaga gctaaacagt    1620
gacatttcta aaattcctac acagggaatt aaaagaaaac tacaacaaaa tggcctgcac    1680
agcaaagcca gcctgcacag caaaaccagg aaggtcacca agaagtcaac ccacaagagt    1740
gcaaagcctt ccaaaacaag tcagaaaagg aggggtagac gtgctggccg ccgtaccact    1800
gtcagaagaa acagagttta agttgaatt gtttgttaaa cctgttattg gaaatgcaga    1860
ggggactacc ccacattatt ggtctattag tagcccactt aaaactgctg aagctgctaa    1920
tgttactcct gatgctgata ctactgtgtg ctacagcttg tcacaggttg ctcccctga    1980 tattcctaat caggttagtg aatgtgacat gcttatatgg gagctgtata aatggaaac    2040 agaagttttg gtgcttcctg tgcttaatgc tggcatactt actacagggg gtgtaggagg    2100
tattgctggt cctcaacttt attttttggc agttggagga cagcccttgg atgtgctagg    2160
acttgctccc actgaaaat acaagggccc tgctcagtat actgtaaatc ctaaaaccaa    2220
tggtactgtg cctcatgttt attccagttc tgaaacaccc agggcaaggg tcactaatga    2280
aaagtacagc attgaatcat gggtggcaga ccctagccgc aatgataact gcagatactt    2340
tggcagaatg gttggagggg ctgcaactcc accagtggtg tcatttagta ataatagcac    2400
aattccactg ttggatgaaa atggcattgg cattctttgc ttgcaaggta gattgtacat    2460
aacttgtgct gacctttgg gagttaacaa aaatagagta catacagggc tttccagatt    2520
ttttaggcta cactttagac aaagaagggt tagaaaccca tatactataa atttgctta    2580 taagcaggtg tttaataagc cagctgatga cattagtggg caactgcagg ttacagaggt    2640
tactatgact gaagaaacag ggcccttgcc tcccacagta gagggaaatg ttggtgtacc    2700
cacaaccagt aatttgtctc atttgcctgc aactgtaact ttacaagcca caggcccaat    2760
actaaacaca caaggataat gtaataaatg cagtttatta ataaagcaat tttaagcatt    2820
gtgtttttca agtatgttgc atccatttgt tacattcatt tgcatgtcag caaattcagt    2880
aaggcctata tatttgtcta acagttcttt ccaatacaca actttagctt gtatacatgg    2940
gtgaaaatca ctaacaggcc tgcaccatat taacataagt aaaatacaca ttccactttg    3000
taaaactctt tttaccatta gttctggagt tttatccaga ctttcttta agtgtctttt    3060 gggtgtaaaa agtacagttt tatgaaatct aggagccaaa gtagcaggga ctaaatattc    3120
attcattgtt acaatacctg gaggaaaaat ttgtgacctt ttatttaaat gtttttttc    3180 taaattaact ttaacacttc catctaaata gtctcttaaa ttatctaagt tactcattcc    3240
atttccagat ggtaacagtt tattatctcc tacttgacct tttacatctt caaatactac    3300
tgtaaattga tctattgcaa ctcctaactc aaagtttaat ctatcagctg aatattaat    3360 atttaaggcc tttcctccac aaaggtcaag taaagcagca gcaacagttg ttttaccact    3420
gtttataggc cccttaaaaa cccaatacct ttttttaggt acattttcaa ctataacttt    3480
taggtacctg tatacaagct catctatttt accatttagg cctaaatacc aggctacacc    3540
agccatatat aataaaacat cttgctcacc tttaatagtt ttatccattt tgtctagtat    3600
tttttcaaat cttctagcta ataaatcttc tctggacata tttaaactat ctacccttct    3660
ttttgcaata accacatcaa tagcctgttg acacacattt ttttgacttt tactgtctga    3720
```

-continued

```
aaatagtaaa gcattttttt gatgttccat atgaagtcta ttatgagttg catcttcatt      3780
actattgcat ttttcacact cttctacctt aatagatagt tgtaaatata atccaagtaa      3840
taagtacaca tcatcaattc ctaattctaa agcaaattct gacaaagcct tccaatttaa      3900
ttgatcttta aactccccat ataaatcctc agctttaaaa tcattttctt ttaagccacc      3960
aggaatattt tcttcacata aagtaaatgg atctctagtc attctactat ataaaccata      4020
tgcattatta acacctttac aaaataaaaa gctaatagta cagtatccct tacaaaagtt      4080
attaacagca ctaactctat gtctaaaagg tgttaaaata aacacaagtg cagtattata      4140
ataagaatgt ctacttgcaa aattacattt aaacttactt aaaagttttt tatataggt       4200
ttctgccttt tctttggtgg tatgtattac aaatgcagtt aaagttctat tactaaatac      4260
agcttgagac acaaattctt ccaattcttt aggaaatgat aaagatgcat ctgtagcatt      4320
gtcctttttt ttttaggtg tgttgcctg tgaacattgt ggttcctcat catcttctct        4380
agtacgcttt gtaggggttt ctccaggaga tttaggcatt tcctcattac atcttagttc      4440
ttcttcccag taggaattaa actgagacca ccagtaatcc caagtctggg gtaccatatg      4500
tgggtatcta taataaaaaa aagttattaa tttacttata aaacataaaa gtaccccctat     4560
aataaaaaca tgcttacctg gttaagccaa ccccttycat ggttgtaaga aatataatct      4620
ttttccayta aaaaaatgtt tctgcactaa tttcaaagcc aaaccactct ctatagcacc      4680
tgtagcagta acactctatc cacattggay gttttctaaa tattttatat ttttgcttgt     4740
ggcgcttgtc taaaagcag taaaaacaat tacacaaata ataaaaccc tttaagcata        4800
tgtcccagtc ttttaaaata tactcttcaa aaacatcacc ataaacttct ccaacaagcc      4860
tgtactttct aggggaaag ttacagcaca attctgtgca ttctacctgt gaagagctcc       4920
acacttcatc ttcttcttca tttagttggt gcactgtact aacacactct tgcagtttta     4980
aatataaaga attaagcttt ttcatttttt cctcatttcc ccctttgtca ggatgaaatt      5040
ctttgcattt gctaaggtat tttgttctca ttagtggtaa atttccccag caggtcatat      5100
caagacccag cagctgcata agttcttttg cttcatttct ggacaaagtt ttatccattt      5160
tgccttcttt agcctcaagg cgcctcagca aggccctctg cttttagttc aaaaaggtga      5220
ggcttttag                                                             5230
```

```
<210> SEQ ID NO 3
<211> LENGTH: 5229
<212> TYPE: DNA
<213> ORGANISM: Polyomaviridae WU Strain S2

<400> SEQUENCE: 3
```

```
gcctcaggcc tccttattat aataaaaaaa agctaagcat gattgacagt gtgggctaaa       60
ccaaaagcac aagaacaaag cttttagcca attagcagcc acaaggtgga gcaaaagtat      120
taagtttcac tgttatgtgc aggaatgtgc agctgtgacc ttttaaagtt tccgggcacg      180
gcgccaactt cctgggcctg gtgccatacc aacacagctg ctgagcttcc ggaatacaat      240
actggtgccc tttgtaagtg ttttacaggt aagtaaggcc tacaacaggg cttatttgta      300
ctataagtta atgggggccc tttgtagtcc agcggaaagt gaagggtggc ttaacagaga      360
cgtccttggg ttcaaaccta agggtgccat aagcaacatt acattaatgt tgtgacatct      420
ccagtcgggg gtattggcct ataggaaacc ctagggctct ataagcagca tacatatgtt      480
gtgacatctc cgttgagtct ggggtattg gtgctaccgt ctcgaaccta gccgacagcc       540
gttggatata aagggtcacc attttatttt cagatgggca tattgcttgc tgtgcctgaa      600
```

```
ataattgctg catctgtagc tggaggagca gaggcactat caattgctgg atctggagct    660
gcaatagcaa ctggtgaagg tttagctgct cttggtgggc ttacagagtc agcagcacta    720
ttaggggaaa ctgttgaaat atctgaagca gctgctactg tactaacaaa agtacctgag    780
cttgtaactg taacacaagg tgtaacagca gctgtacaag ggggtgcagg tcttgtaggt    840
ggtatatata cagctttagc agcagatcgc cctggggacc tgcctgcaag taccccaaca    900
ggaagtccaa gtggactaca tccccccgca ggatacaatc cccaaggagg tggacttaat    960
atccagtcca tccacaagcc cctccacgcc ccctacccag gaatggcact ggcacctatc   1020
cctgaataca acttggaaac tggaattcca ggggtcccgg actgggtatt caacttcatt   1080
gcatcccacc tgcccgagtt gcctagcctg caggacgtgt tcaatagaat gcctatggat   1140
atctggacat catattacaa tacggggaga acagtagtta atagagcagt tagtgaagaa   1200
ttacaaagac tactaggaga tttagaatat ggatttagaa ctgcacttgc caccattggg   1260
gaatctgacc cagtaaatgc tatagttgaa caagtaagaa gctttgttag tggaggaaga   1320
caaagagaac tgttacaaat agctgcaggt caacctgtag acatttctga aggtgtatca   1380
agaggcacag ctactatttc aaatgctgta aagctgtaa gagatgcaac tcaaagacta   1440
tcacaagcaa cctacaactt tgtttatgat gcttctaccc ttccaaggga tggctttaat   1500
gcacttagtg atgagttca caggctaggc cagtggattt caatgcctgg ggctacaggg   1560
ggtactcccc attatgcagc ccctgactgg attttatatg tacttgaaga gctaaacagt   1620
gacatttcta aaattcctac acagggaatt aaaagaaaac tacaacaaaa tggcctgcac   1680
agcaaagcca gcctgcacag caaaaccagg aaggtcacca agaagtcaac ccacaagagt   1740
gcaaagcctt ccaaaacaag tcagaaaagg aggggtagac gtgctggccg ccgtaccact   1800
gtcagaagaa acagagttta agttgaatt gtttgttaaa cctgttattg gaaatgcaga   1860
ggggactacc ccacattatt ggtctattag tagcccactt aaaactgctg aagctgctaa   1920
tgttactcct gatgctgata ctactgtgtg ctacagcttg tcacaggttg ctcccctga   1980
tattcctaat caggttagtg aatgtgcat gcttatatgg gagctgtata gaatggaaac   2040
agaagttttg gtgcttcctg tgcttaatgc tggcatactt actacagggg gtgtaggagg   2100
tattgctggt cctcaacttt atttttgggc agttggagga cagcccttgg atgtgctagg   2160
acttgctccc actgaaaaat acaaggggcc tgctcagtat actgtaaatc ctaaaaccaa   2220
tggtactgtg cctcatgttt attccagttc tgaaacaccc agggcaaggg tcactaatga   2280
aaagtacagc attgaatcat gggtggcaga ccctagccgc aatgataact gcagatactt   2340
tggcagaatg gttggagggg ctgcaactcc accagtggtg tcatttagta ataatagcac   2400
aattccactg ttggatgaaa atggcattgg cattctttgc ttgcaaggta gattgtacat   2460
aacttgtgct gacctttggg agttaacaa aaatagagta catacagggc tttccagatt   2520
ttttaggcta cactttagac aaagaagggt tagaaaccca tatactataa atttgcttta   2580
taagcaggtg tttaataagc cagctgatga cattagtggg caactgcagg ttacagaggt   2640
tactatgact gaagaaacag ggcccttgcc tcccacagta gagggaaatg ttggtgtacc   2700
cacaaccagt aatttgtctc atttgcctgc aactgtaact ttacaagcca caggcccaat   2760
actaaacaca caaggataat gtaataaatg cagtttatta ataaagcaat tttaagcatt   2820
gtgtttttca agtatgttgc atccatttgt tacattcatt tgcatgtcag caaattcagt   2880
aaggcctata tatttgtcta acagttcttt ccaatacaca actttagctt gtatacatgg   2940
gtgaaaatca ctaacaggcc tgcaccatat taacataagt aaaatacaca ttccactttg   3000
```

```
taaaactctt tttaccatta gttctggagt tttatccaga ctttcttta agtgtctttt      3060 gggtgtaaaa agtacagttt tatgaaatct aggagccaaa gtagcaggga ctaaatattc      3120
attcattgtt acaatacctg gaggaaaaat tgtgacctt ttatttaaat gttttttttc       3180
taaattaact ttaacacttt catctaaata gtctcttaaa ttatctaagt tactcattcc      3240
atttccagat ggtaacagtt tattatctcc tacttgacct tttacatctt caaatactac     3300
tgtaaattga tctattgcaa ctcctaactc aaagtttaat ctatcagctg gaatattaat     3360
atttaaggcc tttcctccac aaaggtcaag taaagcagca gcaacagttg ttttaccact     3420
gtttataggc cccttaaaaa cccaatacct ttttttaggt acattttcaa ctataacttt     3480
tagatacctg tatacaagct catctatttt accatttagg cctaaatacc aggctacacc     3540
agccatatat aataaaacat cttgctcacc tttaatagtt ttatccattt tgtccagtat     3600
tttttcaaat cttctagcta ataaatcttc tctggacata tttaaactat ctacccttct     3660
ttttgcaata accacatcaa tagcctgttg acacacattt ttttgacttt tactgtctga     3720
aaatagtaaa gcattttttt gatgttccat atgaagtcta ttatgagttg catcttcatt     3780
actattgcat ttttcacact cttctacctt aatagatagt tgtaaatata atccaagtaa     3840
taagtacaca tcatcaattc ctaattctaa agcaaattct gacaaagcct tccaatttaa     3900
ttgatcttta aactccccat ataaatcctc agctttaaaa tcatttttctt ttaagccacc    3960 aggaatattt tcttcacata agtaaatgg atctctagtc attctactat ataaaccata      4020
tgcattatta acacctttac aaaataaaaa gctaatagta cagtatccct tacaaaagtt     4080
attaacagca ctaactctat gtctaaaagg tgttaaaata aacacaagtg cagtattata     4140
ataagaatgt ctacttgcaa aattacattt aaacttactt aaaagttttt tatatagggt     4200
ttctgccttt tctttggtgg tatgtattac aaatgcagtt aaagttctat tactaaatac     4260
agcttgagac acaaattctt ccaattcttt aggaaatgat aaagatgcat ctgtagcatt     4320
gtcctttttt tttttaggtg gtgttgcctg tgaacattgt ggttcctcat catcttctct     4380
agtacgcttt gtaggggttt ctccaggaga tttaggcatt tcctcattac atcttagttc     4440
ttcttcccag taggaattaa actgagacca ccagtaatcc cagtctgggg taccatatgt     4500
gggtatctat aataaaaaaa agttattaat ttacttataa aacataaaag taccctata      4560 ataaaaacat gcttacctgg ttaagccaac cccttgcatg gttgtaagaa atataatctt     4620
tttccagtaa aaaatgtttt ctgcactaat ttcaaagcca aaccactctc tatagcacct    4680
gtagcagtaa cactctatcc acattggagg ttttctaaat attttatatt tttgcttgtg     4740
gcgcttgtct aaaaagcagt aaaaacaatt acacaaataa taaaaccccct ttaagcatat    4800 gtcccagtct tttaaaatat actcttcaaa aacatcacca taaacttctc caacaagcct     4860
gtactttcta gggggaaagt tacagcacaa ttctgtgcat tctacctgtg aagagctcca     4920
cacttcatct tcttcttcat ttagttggtg cactgtacta acacactctt gcagttttaa     4980
atataaagaa ttaagctttt tcattttttc ctcatttccc cctttgtcag gatgaaattc     5040
tttgcatttg ctaaggtatt ttgttctcat tagtggtaaa tttccccagc aggtcatatc     5100
aagacccagc agctgcataa gttcttttgc ttcatttctg gacaaagttt tatccatttt     5160
gccttcttta gcctcaaggc gcctcagcaa ggccctctgc ttttagttca aaaaggtgag    5220
gctttttag                                                             5229
```

<210> SEQ ID NO 4
<211> LENGTH: 5228
<212> TYPE: DNA

<213> ORGANISM: Polyomaviridae WU Strain S3

<400> SEQUENCE: 4

```
gcctc

```
aaagtacagc attgaatcat gggtggcaga ccctagccgc aatgataact gcagatactt   2340
tggcagaatg gttggagggg ctgcaactcc accagtggtg tcatttagta ataatagcac   2400
aattccactg ttggatgaaa atggcattgg cattctttgc ttgcaaggta gattgtacat   2460
aacttgtgct gacctttggg gagttaacaa aaatagagta catacagggc tttccagatt   2520
ttttaggcta cactttagac aaagaagggt tagaaaccca tatactataa atttgcttta   2580
taagcaggtg tttaataagc cagctgatga cattagtggg caactgcagg ttacagaggt   2640
tactatgact gaagaaacag ggcccttgcc tcccacagta gagggaaatg ttggtgtacc   2700
cacaaccagt aatttgtctc atttgcctgc aactgtaact ttacaagcca caggcccaat   2760
actaaacaca caaggataat gtaataaatg cagttttta ataaagcaat tttaagcatt    2820 gtgttttca agtatgttgc atccatttgt tacattcatt tgcatgtcag caaattcagt    2880
aaggcctata tatttgtcta acagttcttt ccaatacaca actttagctt gtatacatgg   2940
gtgaaaatca ctaacaggcc tgcaccatat taacataagt aaaatacaca ttccactttg   3000
taaaactctt tttaccatta gttctggagt tttatccaga cttcttttta agtgtctttt    3060
gggtgtaaaa agtacagttt tatgaaatct aggagccaaa gtagcaggga ctaaatattc   3120
attcattgtt acaataccct gaggaaaaat ttgtgacctt ttattaaat gtttttttc     3180 taaattaact ttaacacttc catctaaata gtctcttaaa ttatctaagt tactcattcc   3240
atttccagat ggtaacagtt tattatctcc tacttgacct tttacatctt caaatactac   3300
tgtaaattga tctattgcaa ctcctaactc aaagtttaat ctatcagctg gaatattaat   3360
atttaaggcc tttcctccac aaaggtcaag taaagcagca gcaacagttg ttttaccact   3420
gtttataggc cccttaaaaa cccaatacct ttttttaggt acattttcaa ctataacttt   3480
taggtacctg tatacaagct catctatttt accatttagg cctaaatacc aggctacacc   3540
agccatatat aataaaacat cttgctcacc tttaatagtt ttatccattt tgtccagtat   3600
tttttcaaat cttctagcta ataaatcttc tctggacata tttaaactat ctacccttct   3660
ttttgcaata accacaccaa tagcctgttg acacacattt ttttgacttt tactgtctga   3720
aaatagtaaa gcattttttt gatgttccat atgaagtcta ttatgagttg catcttcatt   3780
actattgcat ttttcacact cttctacctt aatagatagt tgtaaatata atccaagtaa   3840
taagtacaca tcatcaattc ctaattctaa agcaaattct gacaaagcct tccaatttaa   3900
ttgatcttta aactccccat ataaatcctc agctttaaaa tcattttctt ttaagccacc   3960
aggaatattt tcttcacata aagtaaatgg atctctagtc attctactat ataaaccata   4020
tgcattatta acacctttac aaaataaaaa gctaatagta cagtatccct tacaaaagtt   4080
attaacagca ctaactctat gtctaaaagg tgttaaaata aacacaagtg cagtattata   4140
ataagaatgt ctacttgcaa aattacattt aaacttactt aaaagttttt tatatagggt   4200
ttctgccttt tctttggtgg tatgtattac aaatgcagtt aaagttctat tactaaatac   4260
agcttgagac acaaattctt ccaattcttt aggaaatgat aaagatgcat ctgtagcatt   4320 gtccttttt ttttaggtgg tgttgcctgt gaacattgtg gttcctcatc atcttctcta    4380
gtacgctttg taggggtttc tccaggagat ttaggcattt cctcattaca tcttagttct   4440
tcttcccagt aggaattaaa ctgagaccac cagtaatccc agtctggggt accatatgtg   4500
ggtatctata ataaaaaaaa gttattaatt tactataaa acataaaagt acccctataa     4560
taaaaacatg cttacctggt taagccaacc ccttgcatgg ttgtaagaaa tataatcttt   4620
ttccagtaaa aaaatgtttc tgcactaatt tcaaagccaa accactctct atagcacctg   4680
```

```
tagcagtaac actctatcca cattggaggt tttctaaata ttttatattt ttgcttgtgg      4740
cgcttgtcta aaaagcagta aaaacaatta cacaaataat aaaacccctt taagcatatg      4800
tcccagtctt ttaaaatata ctcttcaaaa acatcaccat aaacttctcc aacaagcctg      4860
tactttctag ggggaaagtt acagcacaat tctgtgcatt ctacctgtga agagctccac      4920
acttcatctt cttcttcatt tagttggtgc actgtactaa cacactcttg cagttttaaa      4980
tataaagaat taagtttttt cattttttcc tcatttcccc ctttgtcagg atgaaattct      5040
ttgcatttgc taaggtattt tgttctcatt agtggtaaat ttccccagca ggtcatatca      5100
agacccagca gctgcataag ttcttttgct tcatttctgg acaaagtttt atccattttg      5160
ccttctttag cctcaaggcg cctcagcaag gccctctgct tttagttcaa aaaggtgagg      5220
cttttttag                                                             5228

<210> SEQ ID NO 5
<211> LENGTH: 5229
<212> TYPE: DNA
<213> ORGANISM: Polyomaviridae WU Strain S4

<400> SEQUENCE: 5
gcctcaggcc tccttattat aataaaaaaa acctaagcat gattgacagt gtgggctaaa        60
ccaaaagcac aagaacaaag cttttagcca attagcagcc acaaggtgga gcaaaagtat       120
taagtttcac tgttatgtgc aggaatgtgc agctgtgacc ttttaaagtt tccgggcacg       180
gcgccaactt cctgggcctg gtgccatacc aacacagctg ctgagcttcc ggaatacaat       240
actggtgccc tttgtaagtg ttttacaggt aagtaaggcc tacaacaggg cttatttgta       300
ctataagtta atgggggccc tttgtagtcc agcggaaagt gaaggtggc ttaacagaga        360 cgtccttggg ttcaaaccta agggtgccat aagcaacatt acattaatgt tgtgacatct       420
ccagtcgggg gtattggcct ataggaaacc ctagggctct ataagcagca tacatatgtt       480
gtgacatctc cgttgagtct gggggtattg gtgctaccgt ctcgaaccta gccgacagcc       540
gttggatata aagggtcacc attttttatt cagatgggca tattgcttgc tgtgcctgaa       600
ataattgctg catctgtagc tggaggagca gaggcactat caattgctgg atctggagct       660
gcaatagcaa ctggtgaagg tttagctgct cttggtgggc ttacagagtc agcagcacta       720
ttaggggaaa ctgttgaaat atctgaagca gctgctactg tactaacaaa agtacctgag       780
cttgtaactg taacacaagg tgtaacagca gctgtacaag ggggtgcagg tcttgtaggt       840
ggtatatata cagctttagc agcagatcgc cctggggacc tgcctgcgag tacccccaaca      900 ggaagtccaa gtggactaca tccccccgca ggatacaatc cccaaggagg tggacttaat       960
atccagtcca tccacaagcc cctccacgcc ccctacccag gaatggcact ggcacctatc      1020
cctgaataca acttggaaac tggaattcca ggggtcccgg actgggtatt caacttcatt      1080
gcatcccacc tgcccgagtt gcctagcctg caggacgtgt tcaatagaat tgcctatgga      1140
atctggacat catattacaa tacggggaga acagtagtta atagagcagt tagtgaagaa      1200
ttacaaagac tactaggaga tttagaatat ggatttagaa ctgcacttgc caccattggg      1260
gaatctgacc cagtaaatgc tatagttgaa caagtaagaa gctttgttag tggaggaaga      1320
caaagagaac tgttacaaat agctgcaggt caacctgtag acatttctga aggtgtatca      1380
agaggcacag ctactatttc aaatgctgta gaagctgtaa gagatgcaac tcaaagacta      1440
tcacaagcaa cctacaactt tgtttatgat gcttctaccc ttccaaggga tggctttaat      1500
gcacttagtg atggagttca caggctaggc cagtggattt caatgcctgg ggctacaggg      1560
```

```
ggtactcccc attatgcagc ccctgactgg attttatatg tacttgaaga gctaaacagt    1620
gacatttcta aaattcctac acagggaatt aaaagaaaac tacaacaaaa tggcctgcac    1680
agcaaagcca gcctgcacag caaaaccagg aaggtcacca agaagtcaac ccacaagagt    1740
gcaaagcctt ccaaaacaag tcagaaaagg aggggtagac gtgctggccg ccgtaccact    1800
gtcagaagaa acagagttta aagttgaatt gtttgttaaa cctgttattg gaaatgcaga    1860
ggggactacc ccacattatt ggtctattag tagcccactt aaaactgctg aagctgctaa    1920
tgttactcct gatgctgata ctactgtgtg ctacagcttg tcacaggttg ctcccccctga   1980 tattcctaat caggttagtg aatgtgacat gcttatatgg gagctgtata aatggaaac    2040 agaagttttg gtgcttcctg tgcttaatgc tggcatactt actacagggg gtgtaggagg    2100
tattgctggt cctcaacttt attttttgggc agttggagga cagcccttgg atgtgctagg   2160
acttgctccc actgaaaaat acaaggggcc tgctcagtat actgtaaatc ctaaaaccaa    2220
tggtactgtg cctcatgttt attccagttc tgaaacaccc agggcaaggg tcactaatga    2280
aaagtacagc atcgaatcat gggtggcaga ccctagccgc aatgataact gcagatactt    2340
tggcagaatg gttggagggg ctgcaactcc accagtggtg tcatttagta ataatagcac    2400
aattccactg ttggatgaaa atggcattgg cattctttgc ttgcaaggta gattgtacat    2460
aacttgtgct gaccttttgg gagttaacaa aaatagagta catacagggc tttccagatt    2520
ttttaggcta cattttagac aaagaagggt tagaaaccca tatactataa atttgcttta    2580
taagcaggtg tttaataagc cagctgatga cattagtggg caactgcagg ttacagaggt    2640
tactatgact gaagaaacag ggcccttgcc tcccacagta gagggaaatg ttggtgtacc    2700
cacaaccagt aatttgtctc atttgcctgc aactgtaact ttacaagcca caggcccaat    2760
actaaacaca caaggataat gtaataaatg cagtttatta ataaagcaat tttaagcatt    2820 gtgttttca agtatgttgc atccattgt tacattcatt tgcatgtcag caaattcagt     2880
aaggcctata tatttgtcta acagttcttt ccaatacaca actttagctt gtatacatgg    2940
gtgaaaatca ctaacaggcc tgcaccatat taacataagt aaaatacaca ttccactttg    3000
taaaactctt tttaccatta gttctggagt tttatccaga ctttctttta agtgtctttt    3060
gggtgtaaaa agtacagttt tatgaaatct aggagccaaa gtagcaggga ctaaatattc    3120
attcattgtt acaatacctg gaggaaaaat ttgtgacctt ttatttaaat gttttttttc    3180
taaattaact ttaacacttc catctaaata gtctcttaaa ttatctaagt tactcattcc    3240
atttccagat ggtaacagtt tattatctcc tacttgacct tttacatctt caaatactac    3300
tgtaaattga tctattgcaa ctcctaactc aaagtttaat ctatcagctg gaatattaat    3360
atttaaggcc tttcctccac aaaggtcaag taaagcagca gcaacagttg ttttaccact    3420
gtttataggc cccttaaaaa cccaataccc tttttttaggt acattttcaa ctataacttt    3480
taggtacctg tatacaagct catctatttt accatttagg cctaaatacc aggctacacc    3540
agccatatat aataaaacat cttgctcacc tttaatagtt ttatccattt tgtccagtat    3600
tttttcaaat cttctagcta ataaatcttc tctggacata tttaaactat ctacccttct    3660
ttttgcaata accacatcaa tagcctgttg acacacattt ttttgacttt tactgtctga    3720
aaatagtaaa gcatttttt gatgttccat atgaagtcta tatgagttg catcttcatt      3780 actattgcat ttttcacact cttctacctt aatagatagt tgtaaatata atccaagtaa    3840
taagtacaca tcatcaattc ctaattctaa agcaaattct gacaaagcct tccaatttaa    3900
ttgatcttta aactccccat ataaatcctc agctttaaaa tcattttctt ttaagccacc    3960
```

```
aggaatattt tcttcacata aagtaaatgg atctctagtc attctactat ataaaccata   4020
tgcattatta acacctttac aaaataaaaa gctaatagta cagtatccct tacaaaagtt   4080
attaacagca ctaactctat gtctaaaagg tgttaaaata aacacaagtg cagtattata   4140
ataagaatgt ctacttgcaa aattacattt aaacttactt aaaagttttt tatatagggt   4200
ttctgccttt tctttggtgg tatgtattac aaatgcagtt aaagttctat tactaaatac   4260
agcttgagac acaaattctt ccaattcttt aggaaatgat aaagatgcat ctgtagcatt   4320 gtccttttt ttttaggtg gtgttgcctg tgaacattgt ggttcctcat catcttctct    4380
agtacgcttt gtaggggttt ctccaggaga tttaggcatt tcctcattac atcttagttc   4440
ttcttcccag taggaattaa actgagacca ccagtaatcc cagtctgggg taccatatgt   4500
gggtatctat aataaaaaaa agttattaat ttacttataa aacataaaag tacccctata   4560
ataaaaacat gcttacctgg ttaagccaac cccttgcatg gttgtaagaa atataatctt   4620
tttccagtaa aaaatgttt ctgcactaat ttcaaagcca aaccactctc tatagcacct    4680
gtagcagtaa cactctatcc acattggagg ttttctaaat attttatatt tttgcttgtg   4740
gcgcttgtct aaaaagcagt aaaaacaatt acacaaataa taaaaccct ttaagcatat    4800 gtcccagtct tttaaaatat actcttcaaa aacatcacca taaacttctc caacaagcct   4860
gtactttcta gggggaaagt tacagcacaa ttctgtgcat tctacctgtg aagagctcca   4920
cacttcatct tcttcttcat ttagttggtg cactgtacta acacactctt gcagttttaa   4980
atataaagaa ttaagctttt tcattttttc ctcatttccc cctttgtcag gatgaaattc   5040
tttgcatttg ctaaggtatt tgttctcat tagtggtaaa tttccccagc aggtcatatc     5100
aagacccagc agctgcataa gttcttttgc ttcatttctg acaaagtttt tatccatttt   5160
gccttcttta gcctcaaggc gcctcagcaa ggccctctgc ttttagttca aaaggtgag    5220 gcttttttag                                                          5229

<210> SEQ ID NO 6
<211> LENGTH: 5229
<212> TYPE: DNA
<213> ORGANISM: Polyomaviridae WU Strain S5

<400> SEQUENCE: 6
gccccaggcc tccttattat aataaaaaaa agctaagcat gattgacagt gtgggctaaa     60
ccaaaagcac aagaacaaag cttttagcca attagcagcc acaaggtgga gcaaaagtat    120
taagtttcac tgttatgtgc aggaatgtgc agctgtgacc ttttaaagtt tccgggcacg    180
gcgccaactt cctgggcctg gtgccatacc aacacagctg ctgagcttcc ggaatacaat    240
actggtgccc tttgtaagtg ttttacaggt aagtaaggcc tacaacaggg cttatttgta    300
ctataagtta atgggggccc tttgtagtcc agcggaaagt gaagggtggc ttaacagaga    360
cgtccttggg ttcaaaccta agggtgccat aagcaacatt acattaatgt tgtgacatct    420
ccagtcgggg gtattggcct ataggaaacc ctagggctct ataagcagca tacatatgtt    480
gtgacatctc cgttgagtct gggggtattg gtgctaccgt ctcgaaccta gccgacagcc    540
gttggatata aagggtcacc atttttattt cagatgggca tattgcttgc tgtgcctgaa    600
ataattgctg catctgtagc tggaggagca gaggcactat caattgctgg atctggagct    660
gcaatagcaa ctggtgaagg tttagctgct cttggtgggc ttacagagtc agcagcacta    720
ttaggggaaa ctgttgaaat atctgaagca gctgctactg tactaacaaa agtacctgag    780
cttgtaactg taacacaagg tgtaacagca gctgtacaag ggggtgcagg tcttgtaggt    840
```

```
ggtatatata cagctttagc agcagatcgc cctggggacc tgcctgcgag taccccaaca    900
ggaagtccaa gtggactaca tcccccccgca ggatacaatc cccaaggagg tggacttaat    960
atccagtcca tccacaagcc cctccacgcc ccctacccag gaatggcact ggcacctatc   1020
cctgaataca acttggaaac tggaattcca ggggtcccgg actgggtatt caacttcatt   1080
gcatcccacc tgcccgagtt gcctagcctg caggacgtgt tcaatagaat tgcctatgga   1140
atctggacat catattacaa tacggggaga acagtagtta atagagcagt tagtgaagaa   1200
ttacaaagac tactaggaga tttagaatat ggatttagaa ctgcacttgc caccattggg   1260
gaatctgacc cagtaaatgc tatagttgaa caagtaagaa gctttgttag tggaggaaga   1320
caaagagaac tgttacaaat agctgcaggt caacctgtag acatttctga aggtgtatca   1380
agaggcacag ctactatttc aaatgctgta gaagctgtaa gacatgcaac tcaaagacta   1440
tcacaagcaa cctacaactt tgtttatgat gcttctaccc ttccaaggga tggctttaat   1500
gcacttagtg atggagttca caggctaggc cagtggattt caatgcctgg ggctacaggg   1560
ggtactcccc attatgcagc ccctgactgg attttatatg tacttgaaga gctaaacagt   1620
gacatttcta aaattcctac acagggaatt aaaagaaaac tacaacaaaa tggcctgcac   1680
agcaaagcca gcctgcacag caaaaccagg aaggtcacca agaagtcaac ccacaagagt   1740
gcaaagcctt ccaaaacaag tcagaaaagg aggggtagac gtgctggccg ccgtaccact   1800
gtcagaagaa acagagttta agttgaatt gtttgttaaa cctgttattg gaaatgcaga   1860
ggggactacc ccacattatt ggtctattag tagcccactt aaaactgctg aagctgctaa   1920
tgttactcct gatgctgata ctactgtgtg ctacagcttg tcacaggttg ctcccccctga  1980
tattcctaat caggttagtg aatgtgacat gcttatatgg gagctgtata gaatggaaac   2040
agaagttttg gtgcttcctg tgcttaatgc tggcatactt actacagggg gtgtaggagg   2100
tattgctggt cctcaactttt attttgggc agttggagga cagcccttgg atgtgctagg   2160
acttgctccc actgaaaaat acaaggggcc tgctcagtat actgtaaatc ctaaaaccaa   2220
tggtactgtg cctcatgttt attccagttc tgaaacaccc agggcaaggg tcactaatga   2280
aaagtacagc attgaatcat gggtggcaga ccctagccgc aatgataact gcagatactt   2340
tggcagaatg gttggagggg ctgcaactcc accagtggtg tcatttagta ataatagcac   2400
aattccactg ttggatgaaa atggcattgg cattctttgc ttgcaaggta gattgtacat   2460
aacttgtgct gacctttttgg gagttaacaa aaatagagta catacagggc tttccagatt   2520
ttttaggcta cactttagac aaagaagggt tagaaaccca tatactataa atttgcttta   2580
taagcaggtg tttaataagc cagctgatga cattagtggg caactgcagg ttacagaggt   2640
tactatgact gaagaaacag ggcccttgcc tcccacagta gagggaaatg ttggtgtacc   2700
cacaaccagt aatttgtctc atttgcctgc aactgtaact ttacaagcca caggcccaat   2760
actaaacaca caaggataat gtaataaatg cagtttatta ataaagcaat ttaagcatt   2820
gtgtttttca agtatgttgc atccattttgt tacattcatt tgcatgtcag caaattcagt   2880
aaggcctata tatttgtcta acagttcttt ccaatacaca actttagctt gtatacatgg   2940
gtgaaaatca ctaacaggcc tgcaccatat taacataagt aaaatacaca ttccactttg   3000
taaaactctt tttaccatta gttctggagt tttatccaga ctttcttta agtgtctttt   3060
gggtgtaaaa agtacagttt tatgaaatct aggagccaaa gtagcaggga ctaaatattc   3120
attcattgtt acaatacctg gaggaaaaat ttgtgacctt ttattaaat gtttttttc    3180
taaattaact ttaacacttc catctaaata gtctcttaaa ttatctaagt tactcattcc   3240
```

```
atttccagat ggtaacagtt tattatctcc tacttgacct tttacatctt caaatactac    3300
tgtaaattga tctattgcaa ctcctaactc aaagtttaat ctatcagctg gaatattaat    3360
atttaaggcc tttcctccac aaaggtcaag taaagcagca gcaacagttg ttttaccact    3420
gtttataggc cccttaaaaa tccaatacct ttttttaggt acattttcaa ctataacttt    3480
taggtacctg tatacaagct catctatttt accatttagg cctaaatacc aggctacacc    3540
agccatatat aataaaacat cttgctcacc tttaatagtt ttatccattt tgtccagtat    3600 ttttcaaat cttctagcta ataaaccttc tctggacata tttaaactat ctacccttct    3660
ttttgcaata accacatcaa tagcctgttg acacacattt ttttgacttt tactgtctga    3720
aaatagtaaa gcattttttt gatgttccat atgaagtcta ttatgagttg catcttcatt    3780
actattgcat ttttcacact cttctacctt aatagatagt tgtaaatata atccaagtaa    3840
taagtacaca tcatcaattc ctaattctaa agcaaattct gacaaagcct tccaatttaa    3900
ctgatcttta aactcccccat ataaatcctc agctttaaaa tcattttctt ttaagccacc   3960
aggaatattt tcttcacata aagtaaatgg atctctagtc attctactat ataaaccata    4020
tgcattatta acacctttac aaaataaaaa gctaatagta cagtatccct tacaaaagtt    4080
attaacagca ctaactctat gtctaaaagg tgttaaaata aacacaagtg cagtattata    4140
ataagaatgt ctacttgcaa aattacattt aaacttactt aaaagttttt tatatagggt    4200
ttctgccttt tctttggtgg tatgtattac aaatgcagtt aaagttctat tactaaatac    4260
agcttgagac acaaattctt ccaattcttt aggaaatgat aaagatgcat ctgtagcatt    4320 gtccttttt tttttaggtg gtgttgcctg tgaacattgt ggttcctcat catcttctct    4380
agtacgcttt gtaggggttt ctccaggaga tttaggcatt tcctcattac atcttagttc    4440
ttcttcccag taggaattaa actgagacca ccagtaatcc cagtctgggg taccatatgt    4500
gggtatctat aataaaaaaa agttattaat ttacttataa aacataaaag taccccctata    4560 ataaaaacat gcttacctgg ttaagccaac cccttgcatg gttgtaagaa atataatctt    4620
tttccagtaa aaaaatgttt ctgcactaat ttcaaagcca aaccactctc tatagcacct    4680
gtagcagtaa cactctatcc acattggagg ttttctaaat attttatatt tttgcttgtg    4740
gcgcttgtct aaaaagcagt aaaaacaatt acacaaataa taaaaccccct ttaagcatat    4800 gtcccagtct tttaaaatat actcttcaaa aacatcacca taaacttctc caacaagcct    4860
gtactttcta gggggaaagt tacagcacaa ttctgtgcat tctacctgtg aagagctcca    4920
cacttcatct tcttcttcat ttagttggtg cactgtacta acacactctt gcagtttaa    4980 atataaagaa ttaagctttt tcattttttc ctcatttccc cctttgtcag gatgaaattc    5040
tttgcatttg ctaaggtatt ttgttctcat tagtggtaaa tttccccagc aggtcatatc    5100
aagacccagc agctgcataa gttcttttgc ttcatttctg gacaaagttt tatccatttt    5160
gccttcttta gcctcaaggc gcctcagcaa ggccctctgc ttttagttca aaaaggtgag    5220
gcttttttag                                                          5229

<210> SEQ ID NO 7
<211> LENGTH: 250
<212> TYPE: DNA
<213> ORGANISM: Polyomaviridae WU

<400> SEQUENCE: 7
tgttacaaat agctgcaggt caacctgtag acatttctga aggtgtatca agaggcacag     60
ctactatttc aaatgctgta gaagctgtaa gagatgcaac tcaaagacta tcacaagcaa    120
```

```
cctacaactt tgtttatgat gcttctaccc ttccaaggga tggctttaat gcacttagtg    180
atggagttca cagactaggc cagtggattt caatgcctgg ggctacaggg ggtactcccc    240
attatgcagc                                                          250

<210> SEQ ID NO 8
<211> LENGTH: 250
<212> TYPE: DNA
<213> ORGANISM: Polyomaviridae WU Strain B16

<400> SEQUENCE: 8
tgttacaaat agctgcaggt caacctgtag acatttctga aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca caggctaggc cagtggattt caatgcctgg ggctacaggg ggtactcccc    240
attatgcagc                                                          250

<210> SEQ ID NO 9
<211> LENGTH: 250
<212> TYPE: DNA
<213> ORGANISM: Polyomaviridae WU Strain B12

<400> SEQUENCE: 9
tgttacaaat agctgcaggt caacctgtag acatttctga aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca cagactaggc cagtggattt caatgcctgg ggctacaggg ggtactcccc    240
attatgcagc                                                          250

<210> SEQ ID NO 10
<211> LENGTH: 250
<212> TYPE: DNA
<213> ORGANISM: Polyomaviridae WU Strain B3

<400> SEQUENCE: 10
tgttacaaat agctgcaggt caacctgtag acatttctca aggtgtatca acaggcagag     60
ctactatttc aaatgctgta caagctgtaa gagatgcaac tgaaagacta tcacaagcaa    120
cctacaactt tgtttatgat gcttctaccc ttccaaggga tggctttaat gcacttagtg    180
atggagttca cagactaggc cagtggattt caatgcctgg ggctacaggg ggtactcccc    240
attatgcagc                                                          250

<210> SEQ ID NO 11
<211> LENGTH: 250
<212> TYPE: DNA
<213> ORGANISM: Polyomaviridae WU Strain B4

<400> SEQUENCE: 11
tgttacaaat agctgcaggt caacctgtag acatttctga aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca caggctaggc cagtggattt caatgcctgg ggctacaggg ggtactcccc    240
attatgcagc                                                          250

<210> SEQ ID NO 12
```

```
<211> LENGTH: 250
<212> TYPE: DNA
<213> ORGANISM: Polyomaviridae WU Strain B13

<400> SEQUENCE: 12
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca caggctaggc cagtggattt caatgcctgg ggctacaggg ggtactcccc   240
attatgcagc                                                          250

<210> SEQ ID NO 13
<211> LENGTH: 250
<212> TYPE: DNA
<213> ORGANISM: Polyomaviridae WU Strain B20

<400> SEQUENCE: 13
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca cagactaggc cagtggattt caatgcctgg ggctacaggg ggtactcccc   240
attatgcagc                                                          250

<210> SEQ ID NO 14
<211> LENGTH: 250
<212> TYPE: DNA
<213> ORGANISM: Polyomaviridae WU Strain B14

<400> SEQUENCE: 14
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca cagactaggc cagtggattt caatgcctgg ggctacaggg ggtactcccc   240
attatgcagc                                                          250

<210> SEQ ID NO 15
<211> LENGTH: 250
<212> TYPE: DNA
<213> ORGANISM: Polyomaviridae WU Strain B5

<400> SEQUENCE: 15
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca caggctaggc cagtggattt caatgcctgg ggctacaggg ggtactcccc   240
attatgcagc                                                          250

<210> SEQ ID NO 16
<211> LENGTH: 250
<212> TYPE: DNA
<213> ORGANISM: Polyomaviridae WU Strain B11

<400> SEQUENCE: 16
tgttacaaat agctgcaggt caacctgtag acatttctga aggtgtatca agaggcacag    60
```

```
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca caggctaggc cagtggattt caatgcctgg ggctacaggg ggtactcccc    240
attatgcagc                                                          250

<210> SEQ ID NO 17
<211> LENGTH: 250
<212> TYPE: DNA
<213> ORGANISM: Polyomaviridae WU Strain B25

<400> SEQUENCE: 17
tgttacaaat agctgcaggt caacctgtag acatttctga aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca caggctaggc cagtggattt caatgcctgg ggctacaggg ggtactcccc    240
attatgcagc                                                          250

<210> SEQ ID NO 18
<211> LENGTH: 250
<212> TYPE: DNA
<213> ORGANISM: Polyomaviridae WU Strain B15

<400> SEQUENCE: 18
tgttacaaat agctgcaggt caacctgtag acatttctga aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca caggctaggc cagtggattt caatgcctgg ggctacaggg ggtactcccc    240
attatgcagc                                                          250

<210> SEQ ID NO 19
<211> LENGTH: 250
<212> TYPE: DNA
<213> ORGANISM: Polyomaviridae WU Strain B26

<400> SEQUENCE: 19
tgttacaaat agctgcaggt caacctgtag acatttctca aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca cagactaggc cagtggattt caatgcctgg ggctacaggg ggtactcccc    240
attatgcagc                                                          250

<210> SEQ ID NO 20
<211> LENGTH: 250
<212> TYPE: DNA
<213> ORGANISM: Polyomaviridae WU Strain B30

<400> SEQUENCE: 20
tgttacaaat agctgcaggt caacctgtag acatttctga aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca caggctaggc cagtggattt caatgcctgg ggctacaggg ggtactcccc    240
attatgcagc                                                          250
```

```
<210> SEQ ID NO 21
<211> LENGTH: 250
<212> TYPE: DNA
<213> ORGANISM: Polyomaviridae WU Strain B27

<400> SEQUENCE: 21
tgttacaaat agctgcaggt caacctgtag acatttctca aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca cagactaggc cagtggattt caatgcctgg ggctacaggg ggtactcccc    240
attatgcagc                                                          250

<210> SEQ ID NO 22
<211> LENGTH: 250
<212> TYPE: DNA
<213> ORGANISM: Polyomaviridae WU Strain B33

<400> SEQUENCE: 22
tgttacaaat agctgcaggt caacctgtag acatttctga aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca caggctaggc cagtggattt caatgcctgg ggctacaggg ggtactcccc    240
attatgcagc                                                          250

<210> SEQ ID NO 23
<211> LENGTH: 250
<212> TYPE: DNA
<213> ORGANISM: Polyomaviridae WU Strain B32

<400> SEQUENCE: 23
tgttacaaat agctgcaggt caacctgtag acatttctga aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca caggctaggc cagtggattt caatgcctgg ggctacaggg ggtactcccc    240
attatgcagc                                                          250

<210> SEQ ID NO 24
<211> LENGTH: 250
<212> TYPE: DNA
<213> ORGANISM: Polyomaviridae WU Strain B34

<400> SEQUENCE: 24
tgttacaaat agctgcaggt caacctgtag acatttctga aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca cagactaggc cagtggattt caatgcctgg ggctacaggg ggtactcccc    240
attatgcagc                                                          250

<210> SEQ ID NO 25
<211> LENGTH: 250
<212> TYPE: DNA
<213> ORGANISM: Polyomaviridae WU Strain B31

<400> SEQUENCE: 25
```

-continued

```
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca caggctaggc cagtggattt caatgcctgg ggctacaggg ggtactcccc   240
attatgcagc                                                         250
```

<210> SEQ ID NO 26
<211> LENGTH: 250
<212> TYPE: DNA
<213> ORGANISM: Polyomaviridae WU Strain B23

<400> SEQUENCE: 26

```
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca caggctaggc cagtggattt caatgcctgg ggctacaggg ggtactcccc   240
attatgcagc                                                         250
```

<210> SEQ ID NO 27
<211> LENGTH: 250
<212> TYPE: DNA
<213> ORGANISM: Polyomaviridae WU Strain B19

<400> SEQUENCE: 27

```
tgttacaaat agctgcaggt caacctgtag acatttctga aggtgtatca agaggcacag    60
ctactatttc aaatgctgta gaagctgtaa gagatggaac tcaaagacta tcacaagcaa   120
cctacaactt tgtttatgat gcttctaccc ttccaaggga tggctttaat gcacttagtg   180
atggagttca caggctaggc cagtggattt caatgcctgg ggctacaggg ggtactcccc   240
attatgcagc                                                         250
```

<210> SEQ ID NO 28
<211> LENGTH: 250
<212> TYPE: DNA
<213> ORGANISM: Polyomaviridae WU Strain B29

<400> SEQUENCE: 28

```
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca caggctaggc cagtggattt caatgcctgg ggctacaggg ggtactcccc   240
attatgcagc                                                         250
```

<210> SEQ ID NO 29
<211> LENGTH: 250
<212> TYPE: DNA
<213> ORGANISM: Polyomaviridae WU Strain B36

<400> SEQUENCE: 29

```
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca caggctaggc cagtggattt caatgcctgg ggctacaggg ggtactcccc   240
```
attatgcagc 250

<210> SEQ ID NO 30
<211> LENGTH: 250
<212> TYPE: DNA
<213> ORGANISM: Polyomaviridae WU Strain B6

<400> SEQUENCE: 30
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca caggctaggc cagtggattt caatgcctgg ggctacaggg ggtactcccc   240
attatgcagc                                                         250

<210> SEQ ID NO 31
<211> LENGTH: 249
<212> TYPE: DNA
<213> ORGANISM: Polyomaviridae WU Strain B8

<400> SEQUENCE: 31
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatatg cttctaccct tccaagggat ggctttaatg cacttagtga   180
tggagttcac aggctaggcc agtggatttc aatgcctggg gctacagggg gtactcccca   240
ttatgcagc                                                          249

<210> SEQ ID NO 32
<211> LENGTH: 250
<212> TYPE: DNA
<213> ORGANISM: Polyomaviridae WU Strain B7

<400> SEQUENCE: 32
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca caggctaggc cagtggattt caatgcctgg ggctacaggg ggtactcccc   240
attatgcagc                                                         250

<210> SEQ ID NO 33
<211> LENGTH: 250
<212> TYPE: DNA
<213> ORGANISM: Polyomaviridae WU Strain B18

<400> SEQUENCE: 33
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca caggctaggc cagtggattt caatgcctgg ggctacaggg ggtactcccc   240
attatgcagc                                                         250

<210> SEQ ID NO 34
<211> LENGTH: 250
<212> TYPE: DNA
<213> ORGANISM: Polyomaviridae WU Strain B17

```
<400> SEQUENCE: 34
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca caggctaggc cagtggattt caatgcctgg ggctacaggg ggtactcccc   240
attatgcagc                                                         250

<210> SEQ ID NO 35
<211> LENGTH: 250
<212> TYPE: DNA
<213> ORGANISM: Polyomaviridae WU Strain B1

<400> SEQUENCE: 35
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca caggctaggc cagtggattt caatgcctgg ggctacaggg ggtactcccc   240
attatgcagc                                                         250

<210> SEQ ID NO 36
<211> LENGTH: 250
<212> TYPE: DNA
<213> ORGANISM: Polyomaviridae WU Strain B10

<400> SEQUENCE: 36
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca caggctaggc cagtggattt caatgcctgg ggctacaggg ggtactcccc   240
attatgcagc                                                         250

<210> SEQ ID NO 37
<211> LENGTH: 250
<212> TYPE: DNA
<213> ORGANISM: Polyomaviridae WU Strain B21

<400> SEQUENCE: 37
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
atggagttca cagactaggc cagtggattt caatgcctgg ggctacaggg ggtactcccc   240
attatgcagc                                                         250

<210> SEQ ID NO 38
<211> LENGTH: 250
<212> TYPE: DNA
<213> ORGANISM: Polyomaviridae WU Strain B35

<400> SEQUENCE: 38
tgttacaaat agctgcaggt caacctgtag acatttctga aggtgtatca agaggcacag    60
ctactatttc aaatgctgta gaagctgtaa gagatgcaac tcaaagacta tcacaagcaa   120
cctacaactt tgtttatgat gcttctaccc ttccaaggga tggctttaat gcacttagtg   180
```

```
atggagttca caggctaggc cagtggattt caatgcctgg ggctacaggg ggtactcccc    240
attatgcagc                                                           250

<210> SEQ ID NO 39
<211> LENGTH: 250
<212> TYPE: DNA
<213> ORGANISM: Polyomaviridae WU Strain B24

<400> SEQUENCE: 39
tgttacaaat agctgcaggt caacctgtag acatttctga aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca caggctaggc cagtggattt caatgcctgg ggctacaggg ggtactcccc    240
attatgcagc                                                           250

<210> SEQ ID NO 40
<211> LENGTH: 250
<212> TYPE: DNA
<213> ORGANISM: Polyomaviridae WU Strain B22

<400> SEQUENCE: 40
tgttacaaat agctgcaggt caacctgtag acatttctga aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca caggctaggc cagtggattt caatgcctgg ggctacaggg ggtactcccc    240
attatgcagc                                                           250

<210> SEQ ID NO 41
<211> LENGTH: 250
<212> TYPE: DNA
<213> ORGANISM: Polyomaviridae WU Strain B37

<400> SEQUENCE: 41
tgttacaaat agctgcaggt caacctgtag acatttctga aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca caggctaggc cagtggattt caatgcctgg ggctacaggg ggtactcccc    240
attatgcagc                                                           250

<210> SEQ ID NO 42
<211> LENGTH: 250
<212> TYPE: DNA
<213> ORGANISM: Polyomaviridae WU Strain B28

<400> SEQUENCE: 42
tgttacaaat agctgcaggt caacctgtag acatttctga aggtgtatca agaggcacag     60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca caggctaggc cagtggattt caatgcctgg ggctacaggg ggtactcccc    240
attatgcagc                                                           250

<210> SEQ ID NO 43
<211> LENGTH: 238
<212> TYPE: DNA
```

<213> ORGANISM: Polyomaviridae WU Strain B2

<400> SEQUENCE: 43

| tgttacaaat agctgcaggt caacctgtag atgtatcaag aggcacagct actatttcaa | 60 |
| atgctgtaca agctgtaaga gatgcaactg aaagactatc acaagcaacc tacaactttg | 120 |
| tttatgatgc ttctacccct tccaagggatg gctttaatgc acttagtgat ggagttcaca | 180 |
| gactaggcca gtggatttca atgcctgggg ctacagggggg tactccccat tatgcagc | 238 |

<210> SEQ ID NO 44
<211> LENGTH: 250
<212> TYPE: DNA
<213> ORGANISM: Polyomaviridae WU Strain B9

<400> SEQUENCE: 44

| tgttacaaat agctgcaggt caacctgtag acatttctga aggtgtatca agaggcacag | 60 |
| ctactatttc aaatgctgta gaagctgtaa gagatgcaac tcaaagacta tcacaagcaa | 120 |
| cctacaactt tgtttatgat gcttctaccc ttccaaggga tggctttaat gcacttagtg | 180 |
| atggagttca caggctaggc cagtggattt caatgcctgg ggctacaggg ggtactcccc | 240 |
| attatgcagc | 250 |

<210> SEQ ID NO 45
<211> LENGTH: 250
<212> TYPE: DNA
<213> ORGANISM: Polyomaviridae WU Strain S1

<400> SEQUENCE: 45

| tgttacaaat agctgcaggt caacctgtag acatttctga aggtgtatca agaggcacag | 60 |
| ctactatttc aaatgctgta gaagctgtaa gagatgcaac tcaaagacta tcacaagcaa | 120 |
| cctacaactt tgtttatgat gcttctaccc ttccaaggga tggctttaat gcacttagtg | 180 |
| atggagttca caggctaggc cagtggattt caatgcctgg ggctacaggg ggtactcccc | 240 |
| attatgcagc | 250 |

<210> SEQ ID NO 46
<211> LENGTH: 249
<212> TYPE: DNA
<213> ORGANISM: Polyomaviridae WU Strain S2

<400> SEQUENCE: 46

| tgttacaaat agctgcaggt caacctgtag acatttctga aggtgtatca agaggcacag | 60 |
| ctactatttc aaatgctgta gaagctgtaa gagatgcaac tcaaagacta tcacaagcaa | 120 |
| cctacaactt tgtttatatg cttctaccct tccaagggat ggctttaatg cacttagtga | 180 |
| tggagttcac aggctaggcc agtggatttc aatgcctggg gctacagggg gtactcccca | 240 |
| ttatgcagc | 249 |

<210> SEQ ID NO 47
<211> LENGTH: 250
<212> TYPE: DNA
<213> ORGANISM: Polyomaviridae WU Strain S3

<400> SEQUENCE: 47

| tgttacaaat agctgcaggt caacctgtag acatttctga aggtgtatca agaggcacag | 60 |
| ctactatttc aaatgctgta gaagctgtaa gagatgcaac tcaaagacta tcacaagcaa | 120 |
| cctacaactt tgtttatgat gcttctaccc ttccaaggga tggctttaat gcacttagtg | 180 |

-continued

```
atggagttca caggctaggc cagtggattt caatgcctgg ggctacaggg ggtactcccc    240
attatgcagc                                                           250
```

<210> SEQ ID NO 48
<211> LENGTH: 250
<212> TYPE: DNA
<213> ORGANISM: Polyomaviridae WU Strain S4

<400> SEQUENCE: 48

```
tgttacaaat agctgcaggt caacctgtag acatttctga aggtgtatca agaggcacag    60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca caggctaggc cagtggattt caatgcctgg ggctacaggg ggtactcccc    240
attatgcagc                                                           250
```

<210> SEQ ID NO 49
<211> LENGTH: 250
<212> TYPE: DNA
<213> ORGANISM: Polyomaviridae WU Strain S5

<400> SEQUENCE: 49

```
tgttacaaat agctgcaggt caacctgtag acatttctga aggtgtatca agaggcacag    60
ctactatttc aaatgctgta gaagctgtaa gacatgcaac tcaaagacta tcacaagcaa    120
cctacaactt tgtttatgat gcttctaccc ttccaaggga tggctttaat gcacttagtg    180
atggagttca cagactaggc cagtggattt caatgcctgg ggctacaggg ggtactcccc    240
attatgcagc                                                           250
```

<210> SEQ ID NO 50
<211> LENGTH: 250
<212> TYPE: DNA
<213> ORGANISM: Polyomaviridae WU Strain S6

<400> SEQUENCE: 50

```
tgttacaaat agctgcaggt caacctgtag acatttctga aggtgtatca agaggcacag    60
ctactatttc aaatgctgta gaagctgtaa gagatgcaac tcaaagacta tcacaagcaa    120
cctacaactt tgtttatgat gcttctaccc ttccaaggga tggctttaat gcacttagtg    180
atggagttca caggctaggc cagtggattt caatgcctgg ggctacaggg ggtactcccc    240
attatgcagc                                                           250
```

<210> SEQ ID NO 51
<211> LENGTH: 369
<212> TYPE: PRT
<213> ORGANISM: Polyomaviridae WU VP1
<220> FEATURE:
<221> NAME/KEY: PEPTIDE
<222> LOCATION: (1)...(368)

<400> SEQUENCE: 51

```
Met Ala Cys Thr Ala Lys Pro Ala Cys Thr Ala Lys Pro Gly Arg Ser
 1               5                  10                  15

Pro Arg Ser Gln Pro Thr Arg Val Gln Ser Leu Pro Lys Gln Val Arg
                20                  25                  30

Lys Gly Gly Val Asp Val Leu Ala Ala Val Pro Leu Ser Glu Glu Thr
            35                  40                  45

Glu Phe Lys Val Glu Leu Phe Val Lys Pro Val Ile Gly Asn Ala Glu
        50                  55                  60
```

Gly Thr Thr Pro His Tyr Trp Ser Ile Ser Pro Leu Lys Thr Ala
65                  70                  75                  80

Glu Ala Ala Asn Val Thr Pro Asp Ala Asp Thr Thr Val Cys Tyr Ser
            85                  90                  95

Leu Ser Gln Val Ala Pro Pro Asp Ile Pro Asn Gln Val Ser Glu Cys
            100                 105                 110

Asp Met Leu Ile Trp Glu Leu Tyr Arg Met Glu Thr Glu Val Leu Val
        115                 120                 125

Leu Pro Val Leu Asn Ala Gly Ile Leu Thr Thr Gly Val Gly Gly
        130                 135                 140

Ile Ala Gly Pro Gln Leu Tyr Phe Trp Ala Val Gly Gly Gln Pro Leu
145                 150                 155                 160

Asp Val Leu Gly Leu Ala Pro Thr Glu Lys Tyr Lys Gly Pro Ala Gln
            165                 170                 175

Tyr Thr Val Asn Pro Lys Thr Asn Gly Thr Val Pro His Val Tyr Ser
            180                 185                 190

Ser Ser Glu Thr Pro Arg Ala Arg Val Thr Asn Glu Lys Tyr Ser Ile
        195                 200                 205

Glu Ser Trp Val Ala Asp Pro Ser Arg Asn Asp Asn Cys Arg Tyr Phe
        210                 215                 220

Gly Arg Met Val Gly Gly Ala Ala Thr Pro Pro Val Val Ser Phe Ser
225                 230                 235                 240

Asn Asn Ser Thr Ile Pro Leu Leu Asp Glu Asn Gly Ile Gly Ile Leu
            245                 250                 255

Cys Leu Gln Gly Arg Leu Tyr Ile Thr Cys Ala Asp Leu Leu Gly Val
            260                 265                 270

Asn Lys Asn Arg Val His Thr Gly Leu Ser Arg Phe Phe Arg Leu His
        275                 280                 285

Phe Arg Gln Arg Arg Val Arg Asn Pro Tyr Thr Ile Asn Leu Leu Tyr
        290                 295                 300

Lys Gln Val Phe Asn Lys Pro Ala Asp Asp Ile Ser Gly Gln Leu Gln
305                 310                 315                 320

Val Thr Glu Val Thr Met Thr Glu Val Thr Gly Pro Leu Pro Pro Thr
            325                 330                 335

Val Glu Gly Asn Val Gly Val Pro Thr Thr Ser Asn Leu Ser His Leu
            340                 345                 350

Pro Ala Thr Val Thr Leu Gln Ala Thr Gly Pro Ile Leu Asn Thr Gln
            355                 360                 365

Gly

<210> SEQ ID NO 52
<211> LENGTH: 415
<212> TYPE: PRT
<213> ORGANISM: Polyomaviridae WU VP2
<220> FEATURE:
<221> NAME/KEY: PEPTIDE
<222> LOCATION: (1)...(415)

<400> SEQUENCE: 52

Met Gly Ile Leu Leu Ala Val Pro Glu Ile Ile Ala Ala Ser Val Ala
1               5                   10                  15

Gly Gly Ala Glu Ala Leu Ser Ile Ala Gly Ser Gly Ala Ala Ile Ala
            20                  25                  30

Thr Gly Glu Gly Leu Ala Ala Leu Gly Gly Leu Thr Glu Ser Ala Ala
        35                  40                  45

Leu Leu Gly Glu Thr Val Glu Ile Ser Glu Ala Ala Ala Thr Val Leu
 50                  55                  60

Thr Lys Val Pro Glu Leu Val Thr Val Thr Gln Gly Val Thr Ala Ala
 65                  70                  75                  80

Val Gln Gly Gly Ala Gly Leu Val Gly Gly Ile Tyr Thr Ala Leu Ala
                 85                  90                  95

Ala Asp Arg Pro Gly Asp Leu Pro Ala Ser Thr Pro Thr Gly Ser Pro
                100                 105                 110

Ser Gly Leu His Pro Pro Ala Gly Tyr Asn Pro Gln Gly Gly Gly Leu
                115                 120                 125

Asn Ile Gln Ser Ile His Lys Pro Leu His Ala Pro Tyr Pro Gly Met
130                 135                 140

Ala Leu Ala Pro Ile Pro Glu Tyr Asn Leu Glu Thr Gly Ile Pro Gly
145                 150                 155                 160

Val Pro Asp Trp Val Phe Asn Phe Ile Ala Ser His Leu Pro Glu Leu
                165                 170                 175

Pro Ser Leu Gln Asp Val Phe Asn Arg Ile Ala Tyr Gly Ile Trp Thr
                180                 185                 190

Ser Tyr Tyr Asn Thr Gly Arg Thr Val Val Asn Arg Ala Val Ser Glu
                195                 200                 205

Glu Leu Gln Arg Leu Leu Gly Asp Leu Glu Tyr Gly Phe Arg Thr Ala
210                 215                 220

Leu Ala Thr Ile Gly Glu Ser Asp Pro Val Asn Ala Ile Val Glu Gln
225                 230                 235                 240

Val Arg Ser Phe Val Ser Gly Gly Arg Glu Arg Glu Leu Leu Gln Ile
                245                 250                 255

Ala Ala Gly Gln Pro Val Asp Ile Ser Glu Gly Val Ser Arg Gly Thr
                260                 265                 270

Ala Thr Ile Ser Asn Ala Val Glu Ala Val Arg Asp Ala Thr Gln Arg
                275                 280                 285

Leu Ser Gln Ala Thr Tyr Asn Phe Val Tyr Asp Ala Ser Thr Leu Pro
290                 295                 300

Arg Asp Gly Phe Asn Ala Leu Ser Asp Gly Val His Arg Leu Gly Gln
305                 310                 315                 320

Trp Ile Ser Met Pro Gly Ala Thr Gly Gly Thr Pro His Tyr Ala Ala
                325                 330                 335

Pro Asp Trp Ile Leu Tyr Val Leu Glu Glu Leu Asn Ser Asp Ile Ser
                340                 345                 350

Lys Ile Pro Thr Gln Gly Ile Lys Arg Lys Leu Gln Gln Asn Gly Leu
                355                 360                 365

His Ser Lys Ala Ser Leu His Ser Lys Thr Arg Lys Val Thr Lys Lys
370                 375                 380

Ser Thr His Lys Ser Ala Lys Pro Ser Lys Ser Gln Lys Arg Arg
385                 390                 395                 400

Gly Arg Arg Ala Gly Arg Arg Thr Thr Val Arg Arg Asn Arg Val
                405                 410                 415

<210> SEQ ID NO 53
<211> LENGTH: 272
<212> TYPE: PRT
<213> ORGANISM: Polyomaviridae WU VP3
<220> FEATURE:
<221> NAME/KEY: PEPTIDE
<222> LOCATION: (1)...(272)

<400> SEQUENCE: 53

-continued

```
Met Ala Leu Ala Pro Ile Pro Glu Tyr Asn Leu Glu Thr Gly Ile Pro
  1               5                  10                  15

Gly Val Pro Asp Trp Val Phe Asn Phe Ile Ala Ser His Leu Pro Glu
             20                  25                  30

Leu Pro Ser Leu Gln Asp Val Phe Asn Arg Ile Ala Tyr Gly Ile Trp
         35                  40                  45

Thr Ser Tyr Tyr Asn Thr Gly Arg Thr Val Val Asn Arg Ala Val Ser
     50                  55                  60

Glu Glu Leu Gln Arg Leu Leu Gly Asp Leu Glu Tyr Gly Phe Arg Thr
 65                  70                  75                  80

Ala Leu Ala Thr Ile Gly Glu Ser Asp Pro Val Asn Ala Ile Val Glu
                 85                  90                  95

Gln Val Arg Ser Phe Val Ser Gly Gly Arg Glu Arg Glu Leu Leu Gln
            100                 105                 110

Ile Ala Ala Gly Gln Pro Val Asp Ile Ser Glu Gly Val Ser Arg Gly
        115                 120                 125

Thr Ala Thr Ile Ser Asn Ala Val Glu Ala Val Arg Asp Ala Thr Gln
    130                 135                 140

Arg Leu Ser Gln Ala Thr Tyr Asn Phe Val Tyr Asp Ala Ser Thr Leu
145                 150                 155                 160

Pro Arg Asp Gly Phe Asn Ala Leu Ser Asp Gly Val His Arg Leu Gly
                165                 170                 175

Gln Trp Ile Ser Met Pro Gly Ala Thr Gly Gly Thr Pro His Tyr Ala
            180                 185                 190

Ala Pro Asp Trp Ile Leu Tyr Val Leu Glu Glu Leu Asn Ser Asp Ile
        195                 200                 205

Ser Lys Ile Pro Thr Gln Gly Ile Lys Arg Lys Leu Gln Gln Asn Gly
    210                 215                 220

Leu His Ser Lys Ala Ser Leu His Ser Lys Thr Arg Lys Val Thr Lys
225                 230                 235                 240

Lys Ser Thr His Lys Ser Ala Lys Pro Ser Lys Thr Ser Gln Lys Arg
                245                 250                 255

Arg Gly Arg Arg Ala Gly Arg Arg Thr Thr Val Arg Arg Asn Arg Val
            260                 265                 270

<210> SEQ ID NO 54
<211> LENGTH: 648
<212> TYPE: PRT
<213> ORGANISM: Polyomaviridae WU
<220> FEATURE:
<221> NAME/KEY: PEPTIDE
<222> LOCATION: (1)...(648)
<223> OTHER INFORMATION: large T antigen

<400> SEQUENCE: 54

Met Asp Lys Thr Leu Ser Arg Asn Glu Ala Lys Glu Leu Met Gln Leu
  1               5                  10                  15

Leu Gly Leu Asp Met Thr Cys Trp Gly Asn Leu Pro Leu Met Arg Thr
             20                  25                  30

Lys Tyr Leu Ser Lys Cys Lys Glu Phe His Pro Asp Lys Gly Gly Asn
         35                  40                  45

Glu Glu Lys Met Lys Lys Leu Asn Ser Leu Tyr Leu Lys Leu Gln Glu
     50                  55                  60

Cys Val Ser Thr Val His Gln Leu Asn Glu Glu Asp Glu Val Trp
 65                  70                  75                  80

Ser Ser Ser Gln Ile Pro Thr Tyr Gly Thr Pro Asp Trp Asp Tyr Trp
                 85                  90                  95
```

```
Trp Ser Gln Phe Asn Ser Tyr Trp Glu Glu Leu Arg Cys Asn Glu
            100                 105                 110

Glu Met Pro Lys Ser Pro Gly Glu Thr Pro Lys Arg Thr Arg Glu
            115                 120                 125

Asp Asp Glu Glu Pro Gln Cys Ser Gln Ala Thr Pro Pro Lys Lys Lys
            130                 135                 140

Lys Asp Asn Ala Thr Asp Ala Ser Leu Ser Phe Pro Lys Glu Leu Glu
145                 150                 155                 160

Glu Phe Val Ser Gln Ala Val Phe Ser Asn Arg Thr Leu Thr Ala Phe
            165                 170                 175

Val Ile His Thr Thr Lys Glu Lys Ala Glu Thr Leu Tyr Lys Lys Leu
            180                 185                 190

Leu Ser Lys Phe Lys Cys Asn Phe Ala Ser Arg His Ser Tyr Tyr Asn
            195                 200                 205

Thr Ala Leu Val Phe Ile Leu Thr Pro Phe Arg His Arg Val Ser Ala
            210                 215                 220

Val Asn Asn Phe Cys Lys Gly Tyr Cys Thr Ile Ser Phe Leu Phe Cys
225                 230                 235                 240

Lys Gly Val Asn Asn Ala Tyr Gly Leu Tyr Ser Arg Met Thr Arg Asp
            245                 250                 255

Pro Phe Thr Leu Cys Glu Glu Asn Ile Pro Gly Gly Leu Lys Glu Asn
            260                 265                 270

Asp Phe Lys Ala Glu Asp Leu Tyr Gly Glu Phe Lys Asp Gln Leu Asn
            275                 280                 285

Trp Lys Ala Leu Ser Glu Phe Ala Leu Glu Leu Gly Ile Asp Asp Val
            290                 295                 300

Tyr Leu Leu Leu Gly Leu Tyr Leu Gln Leu Ser Ile Lys Val Glu Glu
305                 310                 315                 320

Cys Glu Lys Cys Asn Ser Asn Glu Asp Ala Thr His Asn Arg Leu His
            325                 330                 335

Met Glu His Gln Lys Asn Ala Leu Leu Phe Ser Asp Ser Lys Ser Gln
            340                 345                 350

Lys Asn Val Cys Gln Gln Ala Ile Asp Val Val Ile Ala Lys Arg Arg
            355                 360                 365

Val Asp Ser Leu Asn Met Ser Arg Glu Asp Leu Leu Ala Arg Arg Phe
            370                 375                 380

Glu Lys Ile Leu Asp Lys Met Asp Lys Thr Ile Lys Gly Glu Gln Asp
385                 390                 395                 400

Val Leu Leu Tyr Met Ala Gly Val Ala Trp Tyr Leu Gly Leu Asn Gly
            405                 410                 415

Lys Ile Gly Glu Leu Val Tyr Arg Tyr Leu Lys Val Ile Val Glu Asn
            420                 425                 430

Val Pro Lys Lys Arg Tyr Trp Val Phe Lys Gly Pro Ile Asn Ser Gly
            435                 440                 445

Lys Thr Thr Val Ala Ala Ala Leu Leu Asp Leu Cys Gly Gly Lys Ala
            450                 455                 460

Leu Asn Ile Asn Ile Pro Ala Asp Arg Leu Asn Phe Glu Leu Gly Val
465                 470                 475                 480

Ala Ile Asp Gln Phe Thr Val Val Phe Glu Asp Val Lys Gly Gln Val
            485                 490                 495

Gly Asp Asn Lys Leu Leu Pro Ser Gly Asn Gly Met Ser Asn Leu Asp
            500                 505                 510

Asn Leu Arg Asp Tyr Leu Asp Gly Ser Val Lys Val Asn Leu Glu Lys
```

-continued

```
              515                 520                 525
Lys His Leu Asn Lys Arg Ser Gln Ile Phe Pro Pro Gly Ile Val Thr
        530                 535                 540

Met Asn Glu Tyr Leu Val Pro Ala Thr Leu Ala Pro Arg Phe His Lys
545                 550                 555                 560

Thr Val Leu Phe Thr Pro Lys Arg His Leu Lys Glu Ser Leu Asp Lys
                565                 570                 575

Thr Pro Glu Leu Met Val Lys Arg Val Leu Gln Ser Gly Met Cys Ile
            580                 585                 590

Leu Ile Met Leu Ile Trp Cys Arg Pro Val Ser Asp Phe His Pro Cys
        595                 600                 605

Ile Gln Ala Lys Val Val Tyr Trp Lys Glu Leu Leu Asp Lys Tyr Ile
610                 615                 620

Gly Leu Thr Glu Phe Ala Asp Met Gln Met Asn Val Thr Asn Gly Cys
625                 630                 635                 640

Asn Ile Leu Glu Lys His Asn Ala
                645
```

<210> SEQ ID NO 55
<211> LENGTH: 194
<212> TYPE: PRT
<213> ORGANISM: Polyomaviridae WU
<220> FEATURE:
<221> NAME/KEY: PEPTIDE
<222> LOCATION: (1)...(192)
<223> OTHER INFORMATION: small T antigen

<400> SEQUENCE: 55

```
Met Asp Lys Thr Leu Ser Arg Asn Glu Ala Lys Glu Leu Met Gln Leu
  1               5                  10                  15

Leu Gly Leu Asp Met Thr Cys Trp Gly Asn Leu Pro Leu Met Arg Thr
             20                  25                  30

Lys Tyr Leu Ser Lys Cys Lys Glu Phe His Pro Asp Lys Gly Gly Asn
         35                  40                  45

Glu Glu Lys Met Lys Lys Leu Asn Ser Leu Tyr Leu Lys Leu Gln Glu
     50                  55                  60

Cys Val Ser Thr Val His Gln Leu Asn Glu Glu Glu Asp Glu Val Trp
 65                  70                  75                  80

Ser Ser Ser Gln Val Glu Cys Thr Glu Leu Cys Cys Asn Phe Pro Pro
                 85                  90                  95

Arg Lys Tyr Arg Leu Val Gly Val Tyr Gly Asp Val Phe Glu Glu
             100                 105                 110

Tyr Ile Leu Lys Asp Trp Asp Ile Cys Leu Lys Gly Phe Tyr Tyr Leu
         115                 120                 125

Cys Asn Cys Phe Tyr Cys Phe Leu Asp Lys Arg His Lys Gln Lys Tyr
    130                 135                 140

Lys Ile Phe Arg Lys Pro Pro Met Trp Ile Glu Cys Tyr Cys Tyr Arg
145                 150                 155                 160

Cys Tyr Arg Glu Trp Phe Gly Phe Glu Ile Ser Ala Glu Thr Phe Phe
                165                 170                 175

Tyr Trp Lys Lys Ile Ile Phe Leu Thr Thr Met Gln Gly Val Gly Leu
            180                 185                 190

Thr Arg
```

<210> SEQ ID NO 56
<211> LENGTH: 654
<212> TYPE: DNA

```
<213> ORGANISM: Polyomaviridae WU
<220> FEATURE:
<221> NAME/KEY: misc_feature
<222> LOCATION: (0)...(0)
<223> OTHER INFORMATION: small T antigen spliced

<400> SEQUENCE: 56
atggataaaa ctttgtccag aaatgaagca aagaactta tgcagctgct gggtcttgat       60
atgacctgct ggggaaattt accactaatg agaacaaaat accttagcaa atgcaaagaa      120
tttcatcctg acaaggggg aaatgaggaa aaatgaaaa agcttaattc tttatattta       180
aaactgcaag agtgtgttag tacagtgcac caactaaatg aagaagaaga tgaagtgtgg      240
agctcttcac aggtagaatg cacagaattg tgctgtaact ttccccctag aaagtacagg      300
cttgttggag aagtttatgg tgatgttttt gaagagtata ttttaaaaga ctgggacata      360
tgcttaaagg ggttttatta tttgtgtaat tgttttttact gcttttaga caagcgccac      420
aagcaaaaat ataaaatatt tagaaaacct ccaatgtgga tagagtgtta ctgctacagg      480
tgctatagag agtggtttgg ctttgaaatt agtgcagaaa cattttttta ctggaaaaag      540
attatatttc ttacaaccat gcaagggggtt ggcttaacca gatacccaca tatggtaccc      600
cagactggga ttactggtgg tctcagttta attcctactg gaagaagaa ctaa             654

<210> SEQ ID NO 57
<211> LENGTH: 217
<212> TYPE: PRT
<213> ORGANISM: Polyomaviridae WU
<220> FEATURE:
<221> NAME/KEY: VARIANT
<222> LOCATION: (0)...(0)
<223> OTHER INFORMATION: small T antigen spliced

<400> SEQUENCE: 57

Met Asp Lys Thr Leu Ser Arg Asn Glu Ala Lys Glu Leu Met Gln Leu
 1               5                  10                  15

Leu Gly Leu Asp Met Thr Cys Trp Gly Asn Leu Pro Leu Met Arg Thr
                20                  25                  30

Lys Tyr Leu Ser Lys Cys Lys Glu Phe His Pro Asp Lys Gly Gly Asn
        35                  40                  45

Glu Glu Lys Met Lys Lys Leu Asn Ser Leu Tyr Leu Lys Leu Gln Glu
    50                  55                  60

Cys Val Ser Thr Val His Gln Leu Asn Glu Glu Glu Asp Glu Val Trp
65                  70                  75                  80

Ser Ser Ser Gln Val Glu Cys Thr Glu Leu Cys Cys Asn Phe Pro Pro
                85                  90                  95

Arg Lys Tyr Arg Leu Val Gly Glu Val Tyr Gly Asp Val Phe Glu Glu
            100                 105                 110

Tyr Ile Leu Lys Asp Trp Asp Ile Cys Leu Lys Gly Phe Tyr Tyr Leu
        115                 120                 125

Cys Asn Cys Phe Tyr Cys Phe Leu Asp Lys Arg His Lys Gln Lys Tyr
    130                 135                 140

Lys Ile Phe Arg Lys Pro Pro Met Trp Ile Glu Cys Tyr Cys Tyr Arg
145                 150                 155                 160

Cys Tyr Arg Glu Trp Phe Gly Phe Glu Ile Ser Ala Glu Thr Phe Phe
                165                 170                 175

Tyr Trp Lys Lys Ile Ile Phe Leu Thr Thr Met Gln Gly Val Gly Leu
            180                 185                 190

Thr Arg Tyr Pro His Met Val Pro Gln Thr Gly Ile Thr Gly Gly Leu
        195                 200                 205
```

```
Ser Leu Ile Pro Thr Gly Lys Lys Asn
    210                 215
```

<210> SEQ ID NO 58
<211> LENGTH: 19
<212> TYPE: DNA
<213> ORGANISM: Artificial Sequence
<220> FEATURE:
<223> OTHER INFORMATION: Primer

<400> SEQUENCE: 58
gccagcatta agcacagga                           19

<210> SEQ ID NO 59
<211> LENGTH: 16
<212> TYPE: DNA
<213> ORGANISM: Artificial Sequence
<220> FEATURE:
<223> OTHER INFORMATION: Primer

<400> SEQUENCE: 59
gtaaaacgac ggccag                              16

<210> SEQ ID NO 60
<211> LENGTH: 22
<212> TYPE: DNA
<213> ORGANISM: Artificial Sequence
<220> FEATURE:
<223> OTHER INFORMATION: Primer

<400> SEQUENCE: 60
gcttgagaca caaattcttc ca                       22

<210> SEQ ID NO 61
<211> LENGTH: 17
<212> TYPE: DNA
<213> ORGANISM: Artificial Sequence
<220> FEATURE:
<223> OTHER INFORMATION: Primer

<400> SEQUENCE: 61
caggaaacag ctatgac                             17

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
tgcattctac ctgtgaagag c                        21

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
gcatttactg ggtcagattc c                        21

<210> SEQ ID NO 64
<211> LENGTH: 19
<212> TYPE: DNA

```
<213> ORGANISM: Artificial Sequence
<220> FEATURE:
<223> OTHER INFORMATION: Primer

<400> SEQUENCE: 64
tcctgtgctt aatgctggc                                               19

<210> SEQ ID NO 65
<211> LENGTH: 16
<212> TYPE: DNA
<213> ORGANISM: Artificial Sequence
<220> FEATURE:
<223> OTHER INFORMATION: Primer

<400> SEQUENCE: 65
gtaaaacgac ggccag                                                  16

<210> SEQ ID NO 66
<211> LENGTH: 22
<212> TYPE: DNA
<213> ORGANISM: Artificial Sequence
<220> FEATURE:
<223> OTHER INFORMATION: Primer

<400> SEQUENCE: 66
tggaagaatt tgtgtctcaa gc                                           22

<210> SEQ ID NO 67
<211> LENGTH: 17
<212> TYPE: DNA
<213> ORGANISM: Artificial Sequence
<220> FEATURE:
<223> OTHER INFORMATION: Primer

<400> SEQUENCE: 67
caggaaacag ctatgac                                                 17

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
tgcatgtcag caaattcagt                                              20

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
ttatgtgcag gaatgtgcag                                              20

<210> SEQ ID NO 70
<211> LENGTH: 16
<212> TYPE: DNA
<213> ORGANISM: Artificial Sequence
<220> FEATURE:
<223> OTHER INFORMATION: Primer

<400> SEQUENCE: 70
gtaaaacgac ggccag                                                  16
```

```
<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
ctctactgtg ggaggcaagg                                               20

<210> SEQ ID NO 72
<211> LENGTH: 17
<212> TYPE: DNA
<213> ORGANISM: Artificial Sequence
<220> FEATURE:
<223> OTHER INFORMATION: Primer

<400> SEQUENCE: 72
caggaaacag ctatgac                                                  17

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
caggatacaa tccccaagga                                               20

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
accttcctgg ttttgctgtg                                               20

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
ctgcacattc ctgcacataa                                               20

<210> SEQ ID NO 76
<211> LENGTH: 16
<212> TYPE: DNA
<213> ORGANISM: Artificial Sequence
<220> FEATURE:
<223> OTHER INFORMATION: Primer

<400> SEQUENCE: 76
gtaaaacgac ggccag                                                   16

<210> SEQ ID NO 77
<211> LENGTH: 20
<212> TYPE: DNA
<213> ORGANISM: Artificial Sequence
<220> FEATURE:
<223> OTHER INFORMATION: Primer
```

-continued

```
<400> SEQUENCE: 77
ccttgcctcc cacagtagag                                              20

<210> SEQ ID NO 78
<211> LENGTH: 17
<212> TYPE: DNA
<213> ORGANISM: Artificial Sequence
<220> FEATURE:
<223> OTHER INFORMATION: Primer

<400> SEQUENCE: 78
caggaaacag ctatgac                                                 17

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
accaggctac accagccata                                              20

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
atgcaagggg ttggcttaac                                              20

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
tagcagccac aaggtggagc                                              20

<210> SEQ ID NO 82
<211> LENGTH: 16
<212> TYPE: DNA
<213> ORGANISM: Artificial Sequence
<220> FEATURE:
<223> OTHER INFORMATION: Primer

<400> SEQUENCE: 82
gtaaaacgac ggccag                                                  16

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
aagggccctg tttcttcagt                                              20

<210> SEQ ID NO 84
<211> LENGTH: 17
<212> TYPE: DNA
```

```
<213> ORGANISM: Artificial Sequence
<220> FEATURE:
<223> OTHER INFORMATION: Primer

<400> SEQUENCE: 84
caggaaacag ctatgac                                          17

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
atgggcatat tgcttgctgt                                       20

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
ttcattgcat cccacctgcc                                       20

<210> SEQ ID NO 87
<211> LENGTH: 20
<212> TYPE: DNA
<213> ORGANISM: Artificial Sequence
<220> FEATURE:
<223> OTHER INFORMATION: Primer

<400> SEQUENCE: 87
atgcagcccc tgactggatt                                       20

<210> SEQ ID NO 88
<211> LENGTH: 21
<212> TYPE: DNA
<213> ORGANISM: Artificial Sequence
<220> FEATURE:
<223> OTHER INFORMATION: Primer

<400> SEQUENCE: 88
gctggcatac tttactacag g                                     21

<210> SEQ ID NO 89
<211> LENGTH: 20
<212> TYPE: DNA
<213> ORGANISM: Artificial Sequence
<220> FEATURE:
<223> OTHER INFORMATION: Primer

<400> SEQUENCE: 89
gctccacctt gtggctgcta                                       20

<210> SEQ ID NO 90
<211> LENGTH: 16
<212> TYPE: DNA
<213> ORGANISM: Artificial Sequence
<220> FEATURE:
<223> OTHER INFORMATION: Primer

<400> SEQUENCE: 90
gtaaaacgac ggccag                                           16
```

```
<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
actgaagaaa cagggccctt                                              20

<210> SEQ ID NO 92
<211> LENGTH: 17
<212> TYPE: DNA
<213> ORGANISM: Artificial Sequence
<220> FEATURE:
<223> OTHER INFORMATION: Primer

<400> SEQUENCE: 92
caggaaacag ctatgac                                                 17

<210> SEQ ID NO 93
<211> LENGTH: 20
<212> TYPE: DNA
<213> ORGANISM: Artificial Sequence
<220> FEATURE:
<223> OTHER INFORMATION: Primer

<400> SEQUENCE: 93
tgttacaata cctggaggaa                                              20

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
ccacatcaat agcctgttga                                              20

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
gctaatagta cagtatccct                                              20

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
caaagccaaa ccactctcta                                              20

<210> SEQ ID NO 97
<211> LENGTH: 23
<212> TYPE: DNA
<213> ORGANISM: Artificial Sequence
<220> FEATURE:
<223> OTHER INFORMATION: Primer
```

```
<400> SEQUENCE: 97
tgttacaaat agctgcaggt caa                                          23

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
gctgcataat ggggagtacc                                              20

<210> SEQ ID NO 99
<211> LENGTH: 23
<212> TYPE: DNA
<213> ORGANISM: Artificial Sequence
<220> FEATURE:
<223> OTHER INFORMATION: Primer

<400> SEQUENCE: 99 tgttttttcaa gtatgttgca tcc                                         23

<210> SEQ ID NO 100
<211> LENGTH: 24
<212> TYPE: DNA
<213> ORGANISM: Artificial Sequence
<220> FEATURE:
<223> OTHER INFORMATION: Primer

<400> SEQUENCE: 100
cacccaaaag acacttaaaa gaaa                                         24

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
agtctttagg gtcttctacc                                              20

<210> SEQ ID NO 102
<211> LENGTH: 20
<212> TYPE: DNA
<213> ORGANISM: Artificial Sequence
<220> FEATURE:
<223> OTHER INFORMATION: Primer

<400> SEQUENCE: 102
ggtgccaacc tatggaacag                                              20

<210> SEQ ID NO 103
<211> LENGTH: 357
<212> TYPE: DNA
<213> ORGANISM: Artificial Sequence
<220> FEATURE:
<223> OTHER INFORMATION: Synthetic construct

<400> SEQUENCE: 103
gcacttatag cagtaacact ctatccacat tggaggtttt ctaaatattt tatattttg    60 cttgtggcgc ttgtctaaaa agcagtaaaa acaattacac aaataataaa accccttaa   120 ccatatgtcc cagtctttta aaatatactc ttcaaaaaca tcaccataaa cttctccaac  180
```

| aagcctgtac tttctagggg gaaagttaca gcacaattct gtgcattcta cctgtgaaga | 240 |
| actccacact tcatcttctt cttcatttag ttggtgcact gtactaacac actcttgcag | 300 |
| ttttaaatat aaagaattaa gcttttcat tttttcctca tttccccctt tgtcagg | 357 |

<210> SEQ ID NO 104
<211> LENGTH: 357
<212> TYPE: DNA
<213> ORGANISM: Artificial Sequence
<220> FEATURE:
<223> OTHER INFORMATION: Synthetic construct

<400> SEQUENCE: 104

| gcagctgtag cagtaacact ctatccacat tggaggtttt ctaaatattt tatattttg | 60 |
| cttgtggcgc ttgtctaaaa agcagtaaaa acaattacac aaataataaa accccttaa | 120 |
| gcatatgtcc cagtctttta aaatatagtc ttcaaaaaca tcaccataaa cttctccaac | 180 |
| aagcctgtac tttctagggg gaaagttaca gcacaattct gtgcattcta cctgtgaaga | 240 |
| gctccacact tcatcttctt cttcatttag ttggtgcact gtactaacac actcttgcag | 300 |
| ttttaaatat aaagaattaa gcttttcat tttttcctca tttccccctt tgtcagg | 357 |

<210> SEQ ID NO 105
<211> LENGTH: 410
<212> TYPE: DNA
<213> ORGANISM: Artificial Sequence
<220> FEATURE:
<223> OTHER INFORMATION: Synthetic construct

<400> SEQUENCE: 105

| tggcttatta aacacctgct tataaagcaa atttatagta tatgggtttc taacccttct | 60 |
| ttgtctaaag tgtagcctaa aaaatctgga aagccctgta tgtactctat ttttgttaac | 120 |
| tcccaaaagg tcagcacaag ttatgtacaa tctaccttgc aagcaaagaa tgccaatgcc | 180 |
| attttcatcc aacagtggaa ttgtgctatt attactaaat gacacgactg gtggagttgc | 240 |
| agcccctcca accattctgc caaagtatct gcagttatca ttgcggctag gtctgccac | 300 |
| ccatgattca atgctgtact tttcattagt gacccttgcc ctgggtgttt cagaactgga | 360 |
| ataaacatga ggcacagtac cattggtttt aggatttaca gtatactgag | 410 |

<210> SEQ ID NO 106
<211> LENGTH: 649
<212> TYPE: DNA
<213> ORGANISM: Artificial Sequence
<220> FEATURE:
<223> OTHER INFORMATION: Synthetic construct

<400> SEQUENCE: 106

| gttgacacac attttttga cttttactgt ctgaaaatag taaagcattt ttttgatgtt | 60 |
| ccatatgaag tctattatga gttgcatctt cattactatt gcattttca cactcttcta | 120 |
| ccttaataga tagttgtaaa tataatccaa gtaataagta cacatcatca attcctaatt | 180 |
| ctaaagcaaa ttctgacaaa gccttccaat ttaattgatc tttaaactcc ccatataaat | 240 |
| cctcagcttt aaaatcattt tctttaagc caccaggaat attttcttca cataaagtaa | 300 |
| atggatctct agtcattcta ctatataaac catatgcatt attaacacct ttacaaaata | 360 |
| aaaagctaat agtacagtat cccttacaaa agttattaac agcactaact ctatgtctaa | 420 |
| aaggtgttaa aataaacaca agtgcagtat tataataaga atgtctactt gcaaaattac | 480 |
| atttaaactt acttaaaagt tttttatata gggtttctgc cttttctttg gtggtatgta | 540 |

-continued

| | |
|---|---|
| ttacaaatgc agttaaagtt ctattactaa atacagcttg agacacaaat tcttccaatt | 600 |
| ctttaggaaa tgataaagat gcatctgtag cattgtcctt tttttttt | 649 |

<210> SEQ ID NO 107
<211> LENGTH: 731
<212> TYPE: DNA
<213> ORGANISM: Artificial Sequence
<220> FEATURE:
<223> OTHER INFORMATION: Synthetic construct

<400> SEQUENCE: 107

| | |
|---|---|
| ttctaaccct tctttgtcta aagtgtagcc taaaaaatct ggaaagccct gtatgtaccc | 60 |
| tatttttgtt aactcccaaa aggtcagcac aagttatgta caatctacct tgcaagcaaa | 120 |
| gaatgccaat gccattttca tccaacagtg gaattgtgct attattacta aatgacacca | 180 |
| ctggtggagt tgcagcccct ccaaccattc tgccaaacta tctgcagtta tcattgcggc | 240 |
| tagggtctgc cacccatgat tcaatgctgt acttttcatt agtgacccct gccctgggtg | 300 |
| tttcagaact ggaataaaca tgaggcacag taccattggt tttaggattt acagtatact | 360 |
| gagcaggccc cttgtatttt tcagtgggag caagtcctag cacatccaag ggctgtcctc | 420 |
| caactgccca aaataaagt tggggaccag caatacctcc tacacccct gtagtaagta | 480 |
| tgccagcatt aagcacagga agcaccaaaa cttctgtttc cattctatac agctcccata | 540 |
| taagcatgtc acattcacta acctgattag gaatatcagg gggagcaacc tgtgacaagc | 600 |
| tgtagcacac agtagtatcg gcatcaggag taacatagca gcttcagcag ttttaagtgg | 660 |
| gctactaata gaccaataat gtgggggtagt cccctctgca tttccaataa caggtttaac | 720 |
| aaacaattca a | 731 |

<210> SEQ ID NO 108
<211> LENGTH: 507
<212> TYPE: DNA
<213> ORGANISM: Artificial Sequence
<220> FEATURE:
<223> OTHER INFORMATION: Synthetic construct

<400> SEQUENCE: 108

| | |
|---|---|
| tccccctgat attcctaatc aggttagtga atgtgacatg cttatatggg agctgtatag | 60 |
| aatggaaaca gaagttttgg tgcttcctgt gcttaatgct ggcatactta ctacaggggg | 120 |
| tgtaggaggt attgctggtc cccaacttta ttttgggca gttggaggac agcccttgga | 180 |
| tgtgctagga cttgctccca ctgaaaaata caaggggcct gctcagtata ctgtaaatcc | 240 |
| taaaaccaat ggtactgtgc ctcatgttta ttccagttct gaaacaccca gggcaagggt | 300 |
| cactaatgaa aagtacagca ttgaatcatg ggtggcagac cctagccgca atgataactg | 360 |
| cagatacttt ggcagaatgg ttggagggggc tgcaactcca ccagtggtgt catttagtaa | 420 |
| taatagcaca attccactgt tggatgaaaa tggcattggc attctttgct tgcaaggtag | 480 |
| attgtacata acttgtgctg acctttt | 507 |

<210> SEQ ID NO 109
<211> LENGTH: 357
<212> TYPE: DNA
<213> ORGANISM: Artificial Sequence
<220> FEATURE:
<223> OTHER INFORMATION: Synthetic construct

<400> SEQUENCE: 109

| | |
|---|---|
| gcacttatag cagtaacact ctatccacat tggaggtttt ctaaatattt tatattttg | 60 |

```
cttgtggcgc ttgtctaaaa agcagtaaaa acaattacac aaataataaa accccttaa      120 gcatatgtcc cagtcttta aaatatactc ttcaaaaaca tcaccataaa cttctccaac      180
aagcctgtac tttctagggg gaaagttaca gcacaattct gtgcattcta cctgtgaaga    240
actccacact tcatcttctt cttcatttag ttggtgcact gtactaacac actcttgcag    300
ttttaaatat aaagaattaa gcttttcat ttttcctca tttcccccctt tgtcagg       357
```

<210> SEQ ID NO 110
<211> LENGTH: 649
<212> TYPE: DNA
<213> ORGANISM: Artificial Sequence
<220> FEATURE:
<223> OTHER INFORMATION: Synthetic construct

<400> SEQUENCE: 110

```
gttgacacac attttttga cttttactgt ctgaaaatag taaagcattt ttttgatgtt     60
ccatatgaag tctattatga gttgcatctt cattactatt gcattttca cactcttcta    120 ccttaataga tagttgtaaa tataatccaa gtaataagta cacatcatca attcctaatt    180
ctaaagcaaa ttctgacaaa gccttccaat ttaattgatc tttaaactcc ccatataaat    240
cctcagcttt aaaatcattt tcttttaagc caccaggaat attttcttca cataaactaa    300
atggatctct agtcattcta ctatataaac catatgcatt attaacaccct ttacaaaata    360 aaaagctaat agtacagtat cccttacaaa agttattaac agcactaact ctatgtctaa    420
aaggtgttaa ataaacaca agtgcagtat tataataaga atgtctactt gcaaaattac    480
atttaaactt acttaaaagt ttttatata gggttctgc cttttctttg gtggtatgta    540
ttacaaatgc agttaaagtt ctattactaa atacagcttg agacacaaat tcttccaatt    600
ctttaggaaa tgataaagat gcatctgtag cattgtcctt tttttttt                 649
```

<210> SEQ ID NO 111
<211> LENGTH: 780
<212> TYPE: DNA
<213> ORGANISM: Artificial Sequence
<220> FEATURE:
<223> OTHER INFORMATION: Synthetic construct

<400> SEQUENCE: 111

```
tggcttatta aacacctgct tataaagcaa atttatagta tatgggttc taaccccttct    60 ttgtctaaaa gtgtagccta aaaaatctgg aaagccctgt atgtacccta ttttgttaa    120 ctcccaaaag gtcagcacaa gttatgtaca atctaccttg caagcaaaga atgccaatgc    180
cattttcatc caacagtgga attgtgctat tattactaaa tgacaccact ggtggagttg    240 cagccctcc aaccattctg ccaaagtatc tgcagttatc attgcggcta gggtctgcca    300
cccatgattc aatgctgtac ttttcattag tgaccttgc cctgggtgtt tcagaactgg    360
aataaacatg aggcacagta ccattggttt taggattac agtatactga gcaggccct    420 tgtatttttc agtgggagca agtcctagca catccaaggg ctgtcctcca actgcccaaa    480 aataagttg gggaccagca atacctccta cacccctgt agtaagtatg ccagcattaa    540
gcacaggaag caccaaaact tctgtttcca ttctatacag ctcccatata agcatgtcac    600
attcactaac ctgattagga atatcagggg gagcaacctg tgacaagctg tagcacacag    660
tagtatcggc atcaggagta acattagcag cttcagcagt tttaagtggg ctactaatag    720
accaataatg tgggtagtc ccctctgcat ttccaataac aggttttaaca aacaattcaa    780
```

<210> SEQ ID NO 112

```
<211> LENGTH: 106
<212> TYPE: DNA
<213> ORGANISM: Polyomaviridae primate SV40

<400> SEQUENCE: 112
gctcagaggc agaggcggcc tcggcctctg cataaataaa aaaaattagt cagcgagtct      60
ccgtctccgc cggagccgga gacgtattta ttttttttaa tcagtc                    106

<210> SEQ ID NO 113
<211> LENGTH: 106
<212> TYPE: DNA
<213> ORGANISM: Polyomaviridae WU

<400> SEQUENCE: 113
aagttgaggc ttttaggcc tcaggcctcc ttattataat aaaaaaaagc taattcaact       60
ccgaaaaatc cggagtccgg aggaataata ttatttttt tcgatt                     106

<210> SEQ ID NO 114
<211> LENGTH: 20
<212> TYPE: DNA
<213> ORGANISM: Artificial Sequence
<220> FEATURE:
<223> OTHER INFORMATION: Baboon polyomavirus large T consensus splice
      donor site

<400> SEQUENCE: 114
tagctctgag gttggttctg                                                  20

<210> SEQ ID NO 115
<211> LENGTH: 20
<212> TYPE: DNA
<213> ORGANISM: Artificial Sequence
<220> FEATURE:
<223> OTHER INFORMATION: SV40 polyomavirus large T consensus splice
      donor site

<400> SEQUENCE: 115
tgcaactgag gtatttgctt                                                  20

<210> SEQ ID NO 116
<211> LENGTH: 20
<212> TYPE: DNA
<213> ORGANISM: Artificial Sequence
<220> FEATURE:
<223> OTHER INFORMATION: JC polyomavirus large T consensus splice donor
      site

<400> SEQUENCE: 116
tagttcagag gttggttgtg                                                  20

<210> SEQ ID NO 117
<211> LENGTH: 20
<212> TYPE: DNA
<213> ORGANISM: Artificial Sequence
<220> FEATURE:
<223> OTHER INFORMATION: BK polyomavirus large T consensus splice donor
      site

<400> SEQUENCE: 117
tagctcagag gtatgtgctg                                                  20

<210> SEQ ID NO 118
<211> LENGTH: 20
<212> TYPE: DNA
<213> ORGANISM: Artificial Sequence
<220> FEATURE:
```

-continued

<223> OTHER INFORMATION: WU polyomavirus large T consensus splice donor
      site

<400> SEQUENCE: 118
ctcttcacag gtagaatgca                                              20

<210> SEQ ID NO 119
<211> LENGTH: 20
<212> TYPE: DNA
<213> ORGANISM: Artificial Sequence
<220> FEATURE:
<223> OTHER INFORMATION: Baboon polyomavirus large T consensus splice
      acceptor site

<400> SEQUENCE: 119
gtttttacag gtgccaacct                                              20

<210> SEQ ID NO 120
<211> LENGTH: 20
<212> TYPE: DNA
<213> ORGANISM: Artificial Sequence
<220> FEATURE:
<223> OTHER INFORMATION: SV40 polyomavirus large T consensus splice
      acceptor site

<400> SEQUENCE: 120
tgtattttag attccaacct                                              20

<210> SEQ ID NO 121
<211> LENGTH: 20
<212> TYPE: DNA
<213> ORGANISM: Artificial Sequence
<220> FEATURE:
<223> OTHER INFORMATION: JC polyomavirus large T consensus splice
      acceptor site

<400> SEQUENCE: 121 tttttttag gtgccaacct                                               20

<210> SEQ ID NO 122
<211> LENGTH: 20
<212> TYPE: DNA
<213> ORGANISM: Artificial Sequence
<220> FEATURE:
<223> OTHER INFORMATION: BK polyomavirus large T consensus splice
      acceptor site

<400> SEQUENCE: 122 tttttatag gtgccaacct                                               20

<210> SEQ ID NO 123
<211> LENGTH: 20
<212> TYPE: DNA
<213> ORGANISM: Artificial Sequence
<220> FEATURE:
<223> OTHER INFORMATION: WU polyomavirus large T consensus splice
      acceptor site

<400> SEQUENCE: 123
tttattatag atacccacat                                              20

<210> SEQ ID NO 124
<211> LENGTH: 20
<212> TYPE: DNA
<213> ORGANISM: Artificial Sequence
<220> FEATURE:
<223> OTHER INFORMATION: Baboon polyomavirus small T consensus splice
      donor site

<400> SEQUENCE: 124
aaactctaag gtaactaagt                                                20

<210> SEQ ID NO 125
<211> LENGTH: 20
<212> TYPE: DNA
<213> ORGANISM: Artificial Sequence
<220> FEATURE:
<223> OTHER INFORMATION: SV40 polyomavirus small T consensus splice
      donor site

<400> SEQUENCE: 125
aagctctaag gtaaatataa                                                20

<210> SEQ ID NO 126
<211> LENGTH: 20
<212> TYPE: DNA
<213> ORGANISM: Artificial Sequence
<220> FEATURE:
<223> OTHER INFORMATION: JC polyomavirus small T consensus splice donor
      site

<400> SEQUENCE: 126
aagctttaag gtaaaccact                                                20

<210> SEQ ID NO 127
<211> LENGTH: 20
<212> TYPE: DNA
<213> ORGANISM: Artificial Sequence
<220> FEATURE:
<223> OTHER INFORMATION: BK polyomavirus small T consensus splice donor
      site

<400> SEQUENCE: 127
aagctttaag gtaactaact                                                20

<210> SEQ ID NO 128
<211> LENGTH: 20
<212> TYPE: DNA
<213> ORGANISM: Artificial Sequence
<220> FEATURE:
<223> OTHER INFORMATION: WU polyomavirus small T consensus splice donor
      site

<400> SEQUENCE: 128
gcttaaccag gtaagcatgt                                                20

<210> SEQ ID NO 129
<211> LENGTH: 20
<212> TYPE: DNA
<213> ORGANISM: Artificial Sequence
<220> FEATURE:
<223> OTHER INFORMATION: Baboon polyomavirus small T consensus splice
      acceptor site

<400> SEQUENCE: 129
gtttttacag gtgccaacct                                                20

<210> SEQ ID NO 130
<211> LENGTH: 20
<212> TYPE: DNA
<213> ORGANISM: Artificial Sequence
<220> FEATURE:
<223> OTHER INFORMATION: SV40 polyomavirus small T consensus splice
      acceptor site

<400> SEQUENCE: 130
tgtattttag attccaacct                                              20

<210> SEQ ID NO 131
<211> LENGTH: 20
<212> TYPE: DNA
<213> ORGANISM: Artificial Sequence
<220> FEATURE:
<223> OTHER INFORMATION: JC polyomavirus small T consensus splice
      acceptor site

<400> SEQUENCE: 131
ttttttttag gtgccaacct                                              20

<210> SEQ ID NO 132
<211> LENGTH: 20
<212> TYPE: DNA
<213> ORGANISM: Artificial Sequence
<220> FEATURE:
<223> OTHER INFORMATION: BK polyomavirus small T consensus splice
      acceptor site

<400> SEQUENCE: 132 tttttttatag gtgccaacct                                             20

<210> SEQ ID NO 133
<211> LENGTH: 20
<212> TYPE: DNA
<213> ORGANISM: Artificial Sequence
<220> FEATURE:
<223> OTHER INFORMATION: WU polyomavirus small T consensus splice
      acceptor site

<400> SEQUENCE: 133
tttattatag atacccacat                                              20

<210> SEQ ID NO 134
<211> LENGTH: 69
<212> TYPE: PRT
<213> ORGANISM: Polyomaviridae AGMPV

<400> SEQUENCE: 134

Arg Ile Leu Asn Ser Gly Tyr Thr Ile Leu Val Leu Leu Trp Tyr
 1               5                  10                  15

Asn Pro Val Asp Ser Phe Thr Pro Lys Val Gln Glu Lys Val Gln
                20                  25                  30

Trp Lys Glu Thr Leu Glu Lys Tyr Val Ser Ile Thr Gln Phe Gly Asn
         35                  40                  45

Ile Gln Gln Asn Ile Ile Asp Gly Lys Asp Pro Leu His Gly Ile Val
     50                  55                  60

Ile Glu Glu Gln Met
 65

<210> SEQ ID NO 135
<211> LENGTH: 63
<212> TYPE: PRT
<213> ORGANISM: Polyomaviridae hamster

<400> SEQUENCE: 135

Arg Val Cys Gln Ser Pro Leu Thr Met Leu Ile Ala Leu Leu Trp Asn
 1               5                  10                  15

Val Pro Thr Glu Asn Phe Asp Lys Ser Leu Lys Glu Lys Val Glu Thr
                20                  25                  30

Glu Lys Lys Val Leu Ser Asp Met Cys Asn Phe Thr Thr Phe Ala Glu

-continued

```
                    35                  40                  45

Met Cys Leu Asn Ile Gln Arg Gly Ala Asp Pro Leu Glu Ala Leu
            50                  55                  60

<210> SEQ ID NO 136
<211> LENGTH: 72
<212> TYPE: PRT
<213> ORGANISM: Polyomaviridae murine

<400> SEQUENCE: 136

Arg Ile Ile Gln Ser Gly Asp Thr Leu Ala Leu Leu Ile Trp Asn
  1               5                  10                  15

Phe Thr Ser Asp Val Phe Asp Pro Asp Ile Gln Gly Leu Val Lys Glu
                 20                  25                  30

Val Arg Asp Gln Phe Ala Ser Glu Cys Ser Tyr Ser Leu Phe Cys Asp
             35                  40                  45

Ile Leu Cys Asn Val Gln Glu Gly Asp Pro Leu Lys Asp Ile Cys
        50                  55                  60

Asp Ile Ala Glu Tyr Thr Val Tyr
 65                  70

<210> SEQ ID NO 137
<211> LENGTH: 163
<212> TYPE: PRT
<213> ORGANISM: Polyomaviridae baboon

<400> SEQUENCE: 137

Arg Ile Leu Gln Ser Gly Met Thr Leu Leu Leu Leu Ile Trp Phe
  1               5                  10                  15

Arg Pro Val Ala Asp Phe Ala Ser Asp Ile Gln His Arg Ile Val Gln
                 20                  25                  30

Trp Lys Glu Arg Leu Asp Ser Glu Ile Ser Met Tyr Thr Phe Ser Arg
             35                  40                  45

Met Lys Tyr Asn Ile Cys Met Gly Lys Cys Ile Leu Asp Trp Ala Arg
         50                  55                  60

Glu Glu Glu Ser Glu Thr Glu Asp Ser Gly His Gly Ser Ser Thr Glu
 65                  70                  75                  80

Ser Gln Ser Gln Cys Phe Ser Gln Ala Ser Asp Thr Ser Gly Ser Ala
                 85                  90                  95

Asp Ala Pro Ala Ser Gln Thr Pro Asp Pro Tyr Asp His Asp Asn Pro
            100                 105                 110

Tyr His Ile Cys Lys Gly Phe Val Cys Phe Lys Arg Pro Lys Thr Pro
            115                 120                 125

Pro Pro Lys Cys Phe Arg Gln Trp Phe Gly Leu Asp Leu Asn Glu Glu
        130                 135                 140

Ala Leu Leu Trp Trp Ser His Ile Ile Gly Glu Thr Pro Phe Arg Asp
145                 150                 155                 160

Leu Lys Leu

<210> SEQ ID NO 138
<211> LENGTH: 127
<212> TYPE: PRT
<213> ORGANISM: Polyomaviridae BK

<400> SEQUENCE: 138

Arg Ile Leu Gln Ser Gly Met Thr Leu Leu Leu Leu Ile Trp Phe
  1               5                  10                  15

Arg Pro Val Ala Asp Phe Ala Thr Asp Ile Gln Ser Arg Ile Val Glu
```

```
                    20                  25                  30

Trp Lys Glu Arg Leu Asp Ser Glu Ile Ser Met Tyr Thr Phe Ser Arg
        35                  40                  45

Met Lys Tyr Asn Ile Cys Met Gly Lys Cys Ile Leu Asp Ile Thr Arg
    50                  55                  60

Glu Glu Asp Ser Glu Thr Glu Asp Ser Gly His Gly Ser Ser Thr Glu
65                  70                  75                  80

Ser Gln Ser Gln Cys Ser Ser Gln Val Ser Asp Thr Ser Ala Pro Ala
                85                  90                  95

Glu Asp Ser Gln Arg Ser Asp Pro His Ser Gln Glu Leu His Leu Cys
            100                 105                 110

Lys Gly Phe Gln Cys Phe Lys Arg Pro Lys Thr Pro Pro Pro Lys
        115                 120                 125

<210> SEQ ID NO 139
<211> LENGTH: 121
<212> TYPE: PRT
<213> ORGANISM: Polyomaviridae JC

<400> SEQUENCE: 139

Arg Ile Leu Gln Ser Gly Met Thr Leu Leu Leu Leu Ile Trp Phe
1               5                   10                  15

Arg Pro Val Ala Asp Phe Ala Ala Ala Ile His Glu Arg Ile Val Gln
                20                  25                  30

Trp Lys Glu Arg Leu Asp Leu Glu Ile Ser Met Tyr Thr Phe Ser Thr
        35                  40                  45

Met Lys Ala Asn Val Gly Met Gly Arg Pro Ile Leu Asp Phe Pro Arg
    50                  55                  60

Glu Glu Asp Ser Glu Ala Glu Asp Ser Gly His Gly Ser Ser Thr Glu
65                  70                  75                  80

Ser Gln Ser Gln Cys Phe Ser Gln Val Ser Glu Ala Ser Gly Ala Asp
                85                  90                  95

Thr Gln Glu Asn Cys Thr Phe His Ile Cys Lys Gly Phe Gln Cys Phe
            100                 105                 110

Lys Lys Pro Lys Thr Pro Pro Pro Lys
        115                 120

<210> SEQ ID NO 140
<211> LENGTH: 142
<212> TYPE: PRT
<213> ORGANISM: Polyomaviridae SV40

<400> SEQUENCE: 140

Arg Ile Ile Gln Ser Gly Ile Ala Leu Leu Leu Met Leu Ile Trp Tyr
1               5                   10                  15

Arg Pro Val Ala Glu Phe Ala Gln Ser Ile Gln Ser Arg Ile Val Glu
                20                  25                  30

Trp Lys Glu Arg Leu Asp Lys Glu Phe Ser Leu Ser Val Tyr Gln Lys
        35                  40                  45

Met Lys Phe Asn Val Ala Met Gly Ile Gly Val Leu Asp Trp Leu Arg
    50                  55                  60

Asn Ser Asp Asp Asp Glu Asp Ser Gln Glu Asn Ala Asp Lys Asn
65                  70                  75                  80

Glu Asp Gly Gly Glu Lys Asn Met Glu Asp Ser Gly His Glu Thr Gly
                85                  90                  95

Ile Asp Ser Gln Ser Gln Gly Ser Phe Gln Ala Pro Gln Ser Ser Gln
            100                 105                 110
```

```
Ser Val His Asp His Asn Gln Pro Tyr His Ile Cys Arg Gly Phe Thr
            115                 120                 125

Cys Phe Lys Lys Pro Pro Thr Pro Pro Glu Pro Glu Thr
    130                 135                 140
```

<210> SEQ ID NO 141
<211> LENGTH: 65
<212> TYPE: PRT
<213> ORGANISM: Polyomaviridae WU

<400> SEQUENCE: 141

```
Arg Val Leu Gln Ser Gly Met Cys Ile Leu Ile Met Leu Ile Trp Cys
  1               5                  10                  15

Arg Pro Val Ser Asp Phe His Pro Cys Ile Gln Ala Lys Val Val Tyr
             20                  25                  30

Trp Lys Glu Leu Leu Asp Lys Tyr Ile Gly Leu Thr Glu Phe Ala Asp
         35                  40                  45

Met Gln Met Asn Val Thr Asn Gly Cys Asn Ile Leu Glu Lys His Asn
     50                  55                  60

Ala
 65
```

<210> SEQ ID NO 142
<211> LENGTH: 62
<212> TYPE: PRT
<213> ORGANISM: Polyomaviridae bovine

<400> SEQUENCE: 142

```
Arg Tyr Leu Gln Ser Gly Ile Thr Trp Leu Leu Leu Leu Ile Tyr Phe
  1               5                  10                  15

Arg Ser Val Asp Asp Phe Thr Glu Lys Leu Gln Glu Cys Val Val Lys
             20                  25                  30

Trp Lys Glu Arg Ile Glu Thr Glu Val Gly Asp Met Trp Leu Leu Thr
         35                  40                  45

Met Lys Glu Asn Ile Glu Gln Gly Lys Asn Ile Leu Glu Lys
     50                  55                  60
```

<210> SEQ ID NO 143
<211> LENGTH: 71
<212> TYPE: PRT
<213> ORGANISM: Polyomaviridae MPPV

<400> SEQUENCE: 143

```
Arg Ile Leu Gln Asn Gly Cys Thr Leu Leu Leu Leu Ile Tyr His
  1               5                  10                  15

Cys Asp Leu Asp Asp Phe Ala Glu Ser Ile Gln Gly Lys Val Arg Ala
             20                  25                  30

Trp Lys Glu Arg Val Asn Ser Glu Ile Ser Val Ser Thr Tyr Leu Glu
         35                  40                  45

Met Arg Gln Cys Cys Leu Glu Gly Arg Tyr Ser Val Cys Thr Lys Tyr
     50                  55                  60

Ser Asn Ala Asn Thr Ala Gln
 65                  70
```

<210> SEQ ID NO 144
<211> LENGTH: 61
<212> TYPE: PRT
<213> ORGANISM: Polyomaviridae BFPV

<400> SEQUENCE: 144

Arg Ile Leu Thr Lys Pro Glu Thr Leu Leu Ala Tyr Leu Leu Ile Arg
1               5                   10                  15

Pro Glu Ser Glu Lys Glu Ile Ser Ala Asp Leu Arg Ala Glu Phe Leu
            20                  25                  30

Thr Val Ile Glu Asn Leu Lys Phe Glu Val Asp Glu Arg Phe Phe Gln
        35                  40                  45

Tyr Asn Asn Arg Leu His Glu Gly Leu Cys Val His Glu
    50                  55                  60

<210> SEQ ID NO 145
<211> LENGTH: 63
<212> TYPE: PRT
<213> ORGANISM: Polyomaviridae finch

<400> SEQUENCE: 145

Arg Ile Leu Thr Lys Ala Glu Thr Leu Leu Ala Leu Leu Leu Ile Asn
1               5                   10                  15

Arg Glu Ser Glu Glu Arg Leu Ser Lys Gln Val Arg Leu Asp Phe Val
            20                  25                  30

Thr Thr Ile Asp Cys Leu Lys Phe Glu Val Glu Gln Arg Ile Trp Lys
        35                  40                  45

Tyr Leu Tyr Asn Leu His Ala Gly Leu Pro Tyr Asp His Glu Asp
    50                  55                  60

<210> SEQ ID NO 146
<211> LENGTH: 60
<212> TYPE: PRT
<213> ORGANISM: Polyomaviridae crow

<400> SEQUENCE: 146

Arg Leu Leu Thr Arg Pro Glu Val Leu Leu Gly Leu Ile Leu Ala
1               5                   10                  15

Asp Thr Glu Val Ile Asp Ile Ser Cys Lys Ser Ala Thr Cys Val Glu
            20                  25                  30

Cys Leu Lys Phe Glu Phe Asp Glu Arg Trp Arg Tyr Tyr Gly Lys Leu
        35                  40                  45

Tyr Glu Gly Glu Ser Cys Phe Glu Gln Thr Asp Thr
    50                  55                  60

<210> SEQ ID NO 147
<211> LENGTH: 66
<212> TYPE: PRT
<213> ORGANISM: Polyomaviridae goose

<400> SEQUENCE: 147

Arg Trp Leu Thr Lys Ala Glu Thr Leu Leu Ala Met Leu Phe Thr Thr
1               5                   10                  15

Pro Lys Ser Phe Arg Asp Glu Ile Thr Gly Lys Cys Ala Asn Val Leu
            20                  25                  30

Asp Ile Leu Lys Ile Glu Phe Asp Ser Arg Ile Leu Asn Tyr Met Phe
        35                  40                  45

Arg Ile His Asn Gly Glu Ser Cys Phe Tyr Glu Pro Glu Asn Thr Gly
    50                  55                  60

Asp Ile
 65

<210> SEQ ID NO 148
<211> LENGTH: 18
<212> TYPE: PRT

```
<213> ORGANISM: Artificial Sequence
<220> FEATURE:
<223> OTHER INFORMATION: Conserved cysteine rich peptide motif
<220> FEATURE:
<221> NAME/KEY: VARIANT
<222> LOCATION: 2
<223> OTHER INFORMATION: Xaa = any amino acid present 5 times
<220> FEATURE:
<221> NAME/KEY: VARIANT
<222> LOCATION: 4
<223> OTHER INFORMATION: Xaa = any amino acid present 7-8 times
<220> FEATURE:
<221> NAME/KEY: VARIANT
<222> LOCATION: 6
<223> OTHER INFORMATION: Xaa = any amino acid
<220> FEATURE:
<221> NAME/KEY: VARIANT
<222> LOCATION: 8, 14
<223> OTHER INFORMATION: Xaa = any amino acid present 2 times
<220> FEATURE:
<221> NAME/KEY: VARIANT
<222> LOCATION: 10
<223> OTHER INFORMATION: Xaa = any amino acid present 21-22 times
<220> FEATURE:
<221> NAME/KEY: VARIANT
<222> LOCATION: 16
<223> OTHER INFORMATION: Xaa = any amino acid present 3 times

<400> SEQUENCE: 148

Cys Xaa Cys Xaa Cys Xaa Cys Xaa Cys Xaa Cys Ser Cys Xaa Cys Xaa
 1               5                  10                  15

Trp Phe

<210> SEQ ID NO 149
<211> LENGTH: 6
<212> TYPE: PRT
<213> ORGANISM: Artificial Sequence
<220> FEATURE:
<223> OTHER INFORMATION: Conserved hexapeptide motif

<400> SEQUENCE: 149

His Pro Asp Lys Gly Gly
 1               5

<210> SEQ ID NO 150
<211> LENGTH: 8
<212> TYPE: PRT
<213> ORGANISM: Artificial Sequence
<220> FEATURE:
<223> OTHER INFORMATION: Conserved peptide motif
<220> FEATURE:
<221> NAME/KEY: VARIANT
<222> LOCATION: 3-5
<223> OTHER INFORMATION: Xaa = any amino acid

<400> SEQUENCE: 150

Gly Pro Xaa Xaa Xaa Gly Lys Thr
 1               5

<210> SEQ ID NO 151
<211> LENGTH: 8
<212> TYPE: PRT
<213> ORGANISM: Artificial Sequence
<220> FEATURE:
<223> OTHER INFORMATION: Conserved peptide motif
<220> FEATURE:
<221> NAME/KEY: VARIANT
<222> LOCATION: 2-4
<223> OTHER INFORMATION: Xaa = any amino acid
```

<400> SEQUENCE: 151

Gly Xaa Xaa Xaa Val Asn Leu Glu
 1               5

The invention claimed is:

1. An isolated nucleic acid molecule comprising the nucleotide sequence of WU Virus (SEQ ID NO:1), WU-Strain_S1 (SEQ ID NO:2), WU-Strain_S2 (SEQ ID NO:3), WU-Strain_S3 (SEQ ID NO:4), WU-Strain_S4 (SEQ ID NO:5), or WU-Strain_S5 (SEQ ID NO:6), or a complement to the entire sequence thereof.

2. A vector comprising the nucleotide sequence of WU Virus (SEQ ID NO:1), WU-Strain_S1 (SEQ ID NO:2), WU-Strain_S2 (SEQ ID NO:3), WU-Strain_S3 (SEQ ID NO:4), WU-Strain_S4 (SEQ ID NO:5), or WU-Strain_S5 (SEQ ID NO:6), or a complement to the entire sequence thereof.

3. An isolated cell comprising the vector of claim 2.

* * * * *